United States Patent
Hoekman et al.

(10) Patent No.: US 10,537,692 B2
(45) Date of Patent: Jan. 21, 2020

(54) MEDICAL UNIT DOSE CONTAINER

(71) Applicant: Impel NeuroPharma Inc., Seattle, WA (US)

(72) Inventors: John D. Hoekman, Seattle, WA (US); Alan Brunelle, Woodinville, WA (US); Craig Kohring, Seattle, WA (US); Christopher Fuller, Seattle, WA (US)

(73) Assignee: Impel Neuropharma, Inc., Seattle, WA (US)

( * ) Notice: Subject to any disclaimer, the term of this patent is extended or adjusted under 35 U.S.C. 154(b) by 748 days.

(21) Appl. No.: 14/787,455

(22) PCT Filed: Apr. 28, 2014

(86) PCT No.: PCT/US2014/035711
§ 371 (c)(1),
(2) Date: Oct. 27, 2015

(87) PCT Pub. No.: WO2014/179228
PCT Pub. Date: Nov. 6, 2014

(65) Prior Publication Data
US 2016/0101245 A1    Apr. 14, 2016

Related U.S. Application Data

(60) Provisional application No. 61/816,799, filed on Apr. 28, 2013.

(51) Int. Cl.
*A61M 15/00* (2006.01)
*A61M 11/00* (2006.01)
(Continued)

(52) U.S. Cl.
CPC ...... *A61M 15/0028* (2013.01); *A61M 11/006* (2014.02); *A61M 11/02* (2013.01);
(Continued)

(58) Field of Classification Search
CPC .... A61M 11/00; A61M 11/02; A61M 11/006; A61M 11/08; A61M 15/00;
(Continued)

(56) References Cited

U.S. PATENT DOCUMENTS

| 3,425,414 A | 2/1969 | Laroche |
| 3,888,253 A | 6/1975 | Wall et al. |

(Continued)

FOREIGN PATENT DOCUMENTS

| DE | 19518580 A1 | 11/1996 |
| DE | 102013100473 A1 | 7/2014 |

(Continued)

OTHER PUBLICATIONS

Appasaheb, et al., "Review on Intranasal Drug Delilvery System", Journal of Advanced Pharmacy Education and Research, vol. 3, Issue 4, Oct. 2013, 14 pages.

(Continued)

*Primary Examiner* — Colin W Stuart
(74) *Attorney, Agent, or Firm* — Fenwick & West LLP

(57) ABSTRACT

A unit dose container for the containment of an intranasal formulation for use with the POD device.

20 Claims, 47 Drawing Sheets

(51) Int. Cl.
*A61M 15/08* (2006.01)
*A61M 11/02* (2006.01)

(52) U.S. Cl.
CPC ...... *A61M 15/0001* (2014.02); *A61M 15/003* (2014.02); *A61M 15/004* (2014.02); *A61M 15/009* (2013.01); *A61M 15/0033* (2014.02); *A61M 15/0035* (2014.02); *A61M 15/0036* (2014.02); *A61M 15/08* (2013.01); *A61M 2207/00* (2013.01); *A61M 2210/0618* (2013.01)

(58) Field of Classification Search
CPC .......... A61M 15/0001; A61M 15/0028; A61M 15/003; A61M 15/0033; A61M 15/0035; A61M 15/0036; A61M 15/0038; A61M 15/004; A61M 15/0041; A61M 15/0061; A61M 15/009; A61M 15/08
USPC ........................................ 128/200.14, 200.23
See application file for complete search history.

(56) References Cited

U.S. PATENT DOCUMENTS

| | | |
|---|---|---|
| 3,906,950 A | 9/1975 | Cocozza |
| 3,908,654 A | 9/1975 | Lhoest et al. |
| 3,921,637 A | 11/1975 | Bennie et al. |
| 3,971,377 A | 7/1976 | Damani |
| 3,998,226 A | 12/1976 | Harris |
| 4,095,596 A | 6/1978 | Grayson |
| 4,187,985 A | 2/1980 | Goth |
| 4,227,522 A | 10/1980 | Carris |
| 4,338,931 A | 7/1982 | Cavazza |
| 4,353,365 A | 10/1982 | Hallworth et al. |
| 4,412,573 A | 11/1983 | Zdeb |
| 4,446,990 A | 5/1984 | Stevenson et al. |
| 4,620,670 A | 11/1986 | Hughes |
| 4,702,415 A | 10/1987 | Hughes |
| 4,896,832 A | 1/1990 | Howlett |
| 4,995,385 A | 2/1991 | Valentini et al. |
| 5,224,471 A | 7/1993 | Marelli et al. |
| 5,307,953 A | 5/1994 | Regan |
| 5,331,954 A | 7/1994 | Rex et al. |
| 5,349,947 A | 9/1994 | Newhouse et al. |
| 5,382,236 A | 1/1995 | Otto et al. |
| 5,398,850 A | 3/1995 | Sancoff et al. |
| 5,435,282 A | 7/1995 | Haber et al. |
| 5,505,193 A | 4/1996 | Ballini et al. |
| 5,516,006 A | 5/1996 | Meshberg |
| 5,531,683 A * | 7/1996 | Kriesel ............... A61M 5/2429 604/416 |
| 5,711,488 A | 1/1998 | Lund |
| 5,715,811 A | 2/1998 | Ohki et al. |
| 5,797,390 A | 8/1998 | McSoley |
| 5,814,020 A | 9/1998 | Gross |
| 5,819,730 A | 10/1998 | Stone et al. |
| 5,823,183 A | 10/1998 | Casper et al. |
| 5,875,776 A | 3/1999 | Vaghefi |
| 5,881,719 A | 3/1999 | Gottenauer et al. |
| 5,901,703 A | 5/1999 | Ohki et al. |
| 5,906,198 A | 5/1999 | Flickinger |
| 5,910,301 A | 6/1999 | Farr et al. |
| 5,954,696 A | 9/1999 | Ryan |
| 6,062,213 A | 5/2000 | Fuisz et al. |
| 6,092,522 A | 7/2000 | Calvert et al. |
| 6,145,703 A | 11/2000 | Opperman |
| 6,158,676 A | 12/2000 | Hughes |
| 6,180,603 B1 | 1/2001 | Frey, II |
| 6,186,141 B1 | 2/2001 | Pike et al. |
| 6,189,739 B1 | 2/2001 | von Schuckmann |
| 6,294,153 B1 | 9/2001 | Modi |
| 6,302,101 B1 | 10/2001 | Py |
| 6,313,093 B1 | 11/2001 | Frey, II |
| 6,347,789 B1 | 2/2002 | Rock |
| 6,367,471 B1 | 4/2002 | Genosar et al. |
| 6,367,473 B1 | 4/2002 | Kafer |
| 6,382,465 B1 | 5/2002 | Greiner-Perth |
| 6,410,046 B1 | 6/2002 | Lerner |
| 6,491,940 B1 | 12/2002 | Levin |
| 6,540,983 B1 | 4/2003 | Adjei et al. |
| 6,569,463 B2 | 5/2003 | Patel et al. |
| 6,585,172 B2 | 7/2003 | Arghyris |
| 6,585,957 B1 | 7/2003 | Adjei et al. |
| 6,585,958 B1 | 7/2003 | Keller et al. |
| 6,595,202 B2 | 7/2003 | Ganan-Calvo |
| 6,622,721 B2 | 9/2003 | Vedrine et al. |
| 6,644,305 B2 | 11/2003 | MacRae et al. |
| 6,644,309 B2 | 11/2003 | Casper et al. |
| 6,647,980 B1 | 11/2003 | Gizurarson |
| 6,681,767 B1 | 1/2004 | Patton et al. |
| 6,684,879 B1 | 2/2004 | Coffee et al. |
| 6,701,916 B2 | 3/2004 | Mezzoli |
| 6,715,485 B1 | 4/2004 | Djupesland |
| 6,734,162 B2 | 5/2004 | Van Antwerp et al. |
| 6,810,872 B1 | 11/2004 | Ohki et al. |
| 6,923,988 B2 | 8/2005 | Patel et al. |
| 6,991,785 B2 | 1/2006 | Frey, II |
| 7,033,598 B2 | 4/2006 | Lerner |
| 7,051,734 B2 | 5/2006 | Casper et al. |
| 7,163,013 B2 | 1/2007 | Harrison |
| 7,182,277 B2 | 2/2007 | Vedrine et al. |
| 7,200,432 B2 | 4/2007 | Lerner et al. |
| 7,214,209 B2 | 5/2007 | Mazzoni |
| 7,231,919 B2 | 6/2007 | Giroux |
| 7,258,119 B2 | 8/2007 | Mazzoni |
| 7,296,566 B2 | 11/2007 | Alchas |
| 7,347,201 B2 | 3/2008 | Djupesland |
| 7,377,901 B2 | 5/2008 | Djupesland et al. |
| 7,476,689 B2 | 1/2009 | Santus et al. |
| 7,481,218 B2 | 1/2009 | Djupesland |
| 7,543,581 B2 | 6/2009 | Djupesland |
| 7,655,619 B2 | 2/2010 | During et al. |
| 7,740,014 B2 | 6/2010 | Djupesland |
| 7,784,460 B2 | 8/2010 | Djupesland et al. |
| 7,799,337 B2 | 9/2010 | Levin |
| 7,832,394 B2 | 11/2010 | Schechter et al. |
| 7,841,337 B2 | 11/2010 | Djupesland |
| 7,841,338 B2 | 11/2010 | Dunne et al. |
| 7,854,227 B2 | 12/2010 | Djupesland |
| 7,866,316 B2 | 1/2011 | Giroux |
| 7,905,229 B2 | 3/2011 | Giroux et al. |
| 7,934,503 B2 | 5/2011 | Djupesland et al. |
| 7,975,690 B2 | 7/2011 | Djupesland |
| 7,994,197 B2 | 8/2011 | Cook et al. |
| 8,001,963 B2 | 8/2011 | Giroux |
| 8,047,202 B2 | 11/2011 | Djupesland |
| 8,119,639 B2 | 2/2012 | Cook et al. |
| 8,122,881 B2 | 2/2012 | Giroux |
| 8,146,589 B2 | 4/2012 | Djupesland |
| 8,171,929 B2 | 5/2012 | Djupesland et al. |
| 8,327,844 B2 | 12/2012 | Djupesland |
| 8,408,427 B2 | 4/2013 | Wong |
| 8,448,637 B2 | 5/2013 | Giroux |
| 8,511,303 B2 | 8/2013 | Djupesland |
| 8,517,026 B2 | 8/2013 | Amon |
| 8,522,778 B2 | 9/2013 | Djupesland |
| 8,550,073 B2 | 10/2013 | Djupesland |
| 8,555,877 B2 | 10/2013 | Djupesland |
| 8,555,878 B2 | 10/2013 | Djupesland |
| 8,596,278 B2 | 12/2013 | Djupesland |
| 8,683,995 B2 | 4/2014 | Sullivan et al. |
| 8,733,342 B2 | 5/2014 | Giroux et al. |
| 8,757,146 B2 | 6/2014 | Hoekman et al. |
| 8,800,555 B2 | 8/2014 | Djupesland |
| 8,839,790 B2 | 9/2014 | Beck Arnon |
| 8,875,794 B2 | 11/2014 | Carlsen et al. |
| 8,899,229 B2 | 12/2014 | Djupesland et al. |
| 8,899,230 B2 | 12/2014 | Immel |
| 8,910,629 B2 | 12/2014 | Djupesland et al. |
| 8,925,544 B2 | 1/2015 | Flickinger |
| 8,978,647 B2 | 3/2015 | Djupesland et al. |
| 8,987,199 B2 | 3/2015 | Abdel Maksoud et al. |
| 9,010,325 B2 | 4/2015 | Djupesland et al. |

(56) References Cited

U.S. PATENT DOCUMENTS

| | | | |
|---|---|---|---|
| 9,038,630 B2 | 5/2015 | Djupesland et al. | |
| 9,067,034 B2 | 6/2015 | Djupesland et al. | |
| 9,072,857 B2 | 7/2015 | Djupesland | |
| 9,101,539 B2 | 8/2015 | Nagata et al. | |
| 9,119,932 B2 | 9/2015 | Djupesland | |
| 9,180,264 B2 | 11/2015 | Young et al. | |
| 9,248,076 B2 | 2/2016 | Sullivan et al. | |
| 9,272,104 B2 | 3/2016 | Djupesland | |
| 9,446,207 B2 | 9/2016 | Jung | |
| 9,550,036 B2 * | 1/2017 | Hoekman | A61M 11/02 |
| 2002/0017294 A1 | 2/2002 | Py | |
| 2002/0054856 A1 | 5/2002 | Jones | |
| 2002/0092520 A1 | 7/2002 | Casper et al. | |
| 2002/0092521 A1 * | 7/2002 | Sullivan | A61M 15/0028 128/200.24 |
| 2003/0017119 A1 | 1/2003 | Rabinowitz et al. | |
| 2003/0158527 A1 | 8/2003 | Mezzoli | |
| 2003/0217748 A1 | 11/2003 | Giroux | |
| 2004/0068222 A1 | 4/2004 | Brian | |
| 2004/0238574 A1 | 12/2004 | Merk et al. | |
| 2005/0023376 A1 | 2/2005 | Anderson | |
| 2005/0028812 A1 | 2/2005 | Djupesland | |
| 2005/0036985 A1 | 2/2005 | Ensoli | |
| 2005/0098172 A1 | 5/2005 | Anderson | |
| 2005/0142072 A1 | 6/2005 | Birch et al. | |
| 2005/0274378 A1 | 12/2005 | Bonney et al. | |
| 2006/0107957 A1 | 5/2006 | Djupesland | |
| 2006/0219813 A1 | 10/2006 | Morrison | |
| 2006/0240092 A1 | 10/2006 | Breitenkamp et al. | |
| 2006/0260608 A1 | 11/2006 | Armstrong et al. | |
| 2007/0056585 A1 | 3/2007 | Davies et al. | |
| 2007/0068514 A1 | 3/2007 | Giroux | |
| 2007/0074722 A1 | 4/2007 | Giroux et al. | |
| 2007/0119451 A1 | 5/2007 | Wang et al. | |
| 2007/0131224 A1 | 6/2007 | Giroux | |
| 2007/0172517 A1 | 7/2007 | Ben-Sasson et al. | |
| 2007/0202051 A1 | 8/2007 | Schuschnig | |
| 2008/0054099 A1 | 3/2008 | Giroux et al. | |
| 2008/0163874 A1 | 7/2008 | Djupesland | |
| 2008/0178871 A1 | 7/2008 | Genova et al. | |
| 2008/0305077 A1 | 12/2008 | Frey, II et al. | |
| 2009/0320832 A1 | 12/2009 | Djupestand | |
| 2010/0074959 A1 | 3/2010 | Hansom et al. | |
| 2010/0108062 A1 * | 5/2010 | Ganem | A61M 15/0028 128/203.21 |
| 2011/0045088 A1 * | 2/2011 | Tsutsui | A61K 9/0043 424/490 |
| 2011/0053859 A1 | 3/2011 | Deadwyler et al. | |
| 2012/0195959 A1 | 8/2012 | Ishii | |
| 2012/0222675 A1 | 9/2012 | Dunne et al. | |
| 2014/0083424 A1 | 3/2014 | Hoekman et al. | |
| 2014/0170220 A1 | 6/2014 | Cartt et al. | |
| 2014/0343494 A1 | 11/2014 | Hoekman et al. | |
| 2015/0057287 A1 | 2/2015 | Cook et al. | |
| 2015/0216823 A1 | 8/2015 | Chatterjee | |
| 2015/0258178 A1 | 9/2015 | Gong | |
| 2016/0228433 A1 | 8/2016 | Haruta et al. | |

FOREIGN PATENT DOCUMENTS

| | | |
|---|---|---|
| EP | 1165044 A2 | 1/2002 |
| GB | 806284 A | 12/1958 |
| GB | 1517642 A | 7/1978 |
| JP | H08322934 A | 12/1996 |
| JP | 2004-526540 | 9/2004 |
| JP | 2010-540147 | 12/2010 |
| WO | WO8601731 A1 | 3/1986 |
| WO | WO9913930 A1 | 3/1999 |
| WO | WO0054887 A1 | 9/2000 |
| WO | WO0136033 A2 | 5/2001 |
| WO | WO0209707 | 2/2002 |
| WO | WO2007/012853 A1 | 2/2007 |
| WO | WO2008/059385 A2 | 5/2008 |
| WO | WO2009100383 A2 | 8/2009 |
| WO | WO 2012/072542 A1 | 6/2012 |
| WO | WO2012119153 | 9/2012 |

OTHER PUBLICATIONS

Baron, "Orally Inhaled Dihydroergotamine; Reviving and Improving a Classic", Future Neurology, May 2011, 11 pages.

Constantino, et al., "Intranasal administration of acetylcholinesterase inhibitors", BMC Neuroscience, Dec. 10, 2008, 3 pages.

The European Office Action dated Nov. 9, 2016 for European patent application No. 14727320.5, a counterpart foreign application of U.S. Appl. No. 14/787,455, 6 pages.

EP Ofice Action for 14727320.5, dated Nov. 9, 2016, 6 pages.

EP Search Report for 09707800.0 dated Jul. 1, 2015, 12 pages.

EP Search Report for 11818832.5 dated Sep. 24, 2014, 6 pages.

Hanson, et al., "Intranasal delivery of growth differentiation factor 5 to the central nervous system", Drug Delivery, 19(3):149-54, Feb. 2012, 7 pages.

Hoekman, J.D., "The Impact of Enhanced Olfactory Deposition and Retention on Direct Nose-to-Brain Drug Delivery", UMI Dissertation Publishing, Apr. 11, 2011, 181 pages.

International Search Report for PCT/US/2009/033468 dated Dec. 2, 2009, 5 pages.

Kumar, et al., "Nasal Drug Delivery: A Potential Route for Brain Targeting" The Pharma Innovation Journal, vol. 2, No. 1, Mar. 2013. 9 pages.

Ozsoy, et al., "Nasal Delivery of High Molecular Weight Drugs", Molecules Journal, Sep. 23, 2009, 26 pages.

Parvathi, "Intranasal Drug Delivery to Brain: An Overview," published in the International Journal of Research in Pharmacy and Chemistry 2012, 2(3), 7 pages.

The PCT Search Report and Written Opinion dated Mar. 27, 2012 for PCT application No. PCT/US11/48435, 14 pages.

Renner, et al., "Intranasal delivery of growth differentiation factor 5 to the central nervous system," Drug Delivery, Feb. 2012, 7 pages.

Stevens, et al., "Systemic and Direct Nose-to-Brain Transport Pharmacokinetic Model for Remoxipride after Intravenous and Intranasal Administration", in "Drug Metabolism and Disposition", The American Society for Pharmacology and Experimental Therapeutics, vol. 39, No. 12, 8 pages.

Talegaonkar, et al., "Intranasal delivery: An approach to bypass the blook brain barrier", Indian J Pharmacol, Jun. 2004, vol. 36, Issue 3, 8 pages.

Westin et al, "Direct Nose to Brain Transfer of Morphine After Nasal Administration to Rats", Pharmaceutical Research, vol. 23, No. 3, Mar. 2006, 8 pgs.

Westin, "Olfactory Tranfser of Analgesic Drugs After Nasal Administration", Digital Comprehensive Summaries of Uppsala Dissertations from the Faculty of Pharmacy 55, May 11, 2007, 66 pages.

Yamada, et al., "Nose-to-brain delivery of TS-002, prostaglandin D2 analogue", Journal of Drug Targeting, Jan. 2007, 9 pages.

Yiman, et al., "Effects of lipid association on lomustine (CCNU) administered intracerebrally to syngeneic 36B-10 rat brain tumors", Cancer Letters 244(2), Dec. 2006, 9 pages.

Ying, "The nose may help the brain: intranasal drug delivery for treating neurological diseases" Future Medecine, 3(1), Jan. 2008, 4 pages.

Zhang, et al, "The brain targeting efficiency following nasally applied MPEG-PLA nanoparticles in rats", Journal of Drug Targeting, Jun. 2006, 11 pages.

The PCT Search Report and Written Opinion dated Aug. 14, 2014 for PCT application No. PCT/US14/35711, 13 pages.

Ding, et al., "Olfactory Mucosa: Composition, Enzymatic Localization, and Metabolism", Handbook of Olfaction and Gustation, 2nd Ed (Doty RL, Ed), 2003, pp. 51-73.

Letrent, et al., "Effects of a Potent and Specific P-Glycoprotein Inhibitor on the Blood-Brain Barrier Distribution and Antinociceptive Effect of Morphine in the Rat", Drug Metab. Dispos., 1991, vol. 27 (7), pp. 827-834.

(56) References Cited

OTHER PUBLICATIONS

Mathison, et al., "Nasal Route for Direct Delivery of Solutes to the Central Nervous System: Fact or Fiction?", J. Drug Target., 1998, vol. 5 (6), pp. 415-441.
Morrison, et al., "Morphology of the Human Olfactory Epithelium", J. Comp. Neurol., 1990, vol. 297 (1), pp. 1-13.
Petroianu, et al., "New K-Oximes (K-27 and K-48) in Comparison with Obidoxime (LuH-6), HI-6, Trimedoxime (TMB-4), and Pralidoxime (2-PAM): Survival in Rats Exposed IP to the Organophosphate Paraoxon", Toxicol. Mech. Methods, 2007, vol. 17 (7), pp. 401-408.
Sakane, et al., "Transport of Cephalexin to the Cerebrospinal Fluid Directly from the Nasal Cavity", J. Pharm. Pharmacol., 1991, vol. 43 (6), pp. 449-451.
Thiermann, et al., "Pharmacokinetics of Obidoxime in Patients Poisoned with Organophosphorus Compounds" Toxicol. Lett., 2010, vol. 197 (3), pp. 236-242.
Zhang, et al., "Preparation of Nimodipine-Loaded Microemulsion for Intranasal Delivery and Evaluation on the Targeting Efficiency to the Brain", Int. J. Pharm., 2004, vol. 275 (1-2), pp. 85-96.
The Second PCT Written Opinion dated Mar. 31, 2015 for PCT application No. PCT/US2014/035711, 8 pages.
Office Action for Japanese Patent Application No. JP 2016-511782, dated Jan. 23, 2018, 12 Pages.

\* cited by examiner

MEDICAL UNIT DOSE CONTAINER

CROSS-REFERENCE TO RELATED APPLICATIONS

This application is a national phase application based on International Application No. PCT/US2014/035711, filed on Apr. 28, 2014, each of which claims priority to U.S. Ser. No. 61/816,799 filed Apr. 28, 2013, the entire contents of which are hereby incorporated by reference herein in their entirety.

BACKGROUND

The central nervous system (CNS) includes the brain, the brain stem, and the spinal cord. The CNS is isolated from the external world by several membranes that both cushion and protect the brain, the brain stem, and the spinal cord. For example, the membranes that form the blood-brain barrier (BBB) protect the brain from certain contents of the blood. The blood-cerebrospinal fluid barrier (BCSFB) protects other portions of the CNS from many chemicals and microbes.

A majority of studies investigating the nose-to-brain delivery route have been performed in rodents. Evidence supports the nose-to-brain delivery route also exits in man. One of the challenges of translating these results into a useful clinical and commercial brain and CNS product is the successful deposition of drug on the olfactory region of the nasal cavity. Delivering drug so that it is deposited on the olfactory region of the nasal cavity is difficult and challenging to accomplish. The complex architecture of the nasal cavity and the turbinate guided air path for inhaled breath through the nose act as natural obstacles to prevent materials from depositing on the olfactory region as a way to protect this entry way into the Central Nervous System.

Traditional methods for delivering compounds to the CNS are typically invasive. For example, a pump implanted in the skull, such as an intracerebroventricular pump, can deliver a variety of compounds to the brain. However, implanting such a pump requires brain surgery, which can entail a variety of serious complications. Certain compounds, for example epidural painkillers, can be injected directly through the protective membrane into the CNS. However, such injection is impractical for most compounds.

Current nasal drop or spray devices are designed to saturate the lower nasal cavity. Drug deposited on the nasal mucosa of the lower nasal cavity is absorbed into the blood stream instead of the CNS. Deposition to the lower nasal cavity eliminates the advantage of using the nasal route for CNS delivery.

Intranasal administration has traditionally focused on the distribution of drug solutions as a mist for topical delivery to the nasal epithelium. Because of the nasal cavity's easily accessed vascular bed, nasal administration of medications has focused the delivery of medications either locally to the nasal cavity or directly to the blood stream.

Much of the current brain research is focused on the enhancement of the drug being delivered to the brain by various formulations. The traditional approaches to improve uptake of compounds to the brain by formulation enhancement include (1) mucoadhesive formulations; 2) penetration enhancers; 3) liposomes; 4) vasoconstrictors; and 5) nanoparticles. Examples of various compounds with have enhanced formulations include various cytokines, for example, tumor necrosis factors, interleukins, and interferons discussed in U.S. Pat. No. 6,991,785 and growth and differentiation factor-5 (GDF-5) and related proteins discussed in US Publication No. 20100074959.

Targeting of drugs to the central nervous system (CNS) is a challenging task. A great number of drugs, including biotechnology products, are candidates for treatment of CNS diseases, but drug delivery is a problem for brain targeting. A limitation in the treatment of brain tumors is that less than 1% of most therapeutic agents administered systemically are able to cross the BBB. The transport of small molecules across the BBB is the exception rather than the rule, and 98% of all small molecules do not cross the BBB (Partridge, NeuroRx. 2005 January; 2(1): 1-2. 2005); approximately 100% of large-molecule drugs or genes do not cross the BBB (Partridge, NeuroRx. 2005 January; 2(1): 1-2. 2005). The BBB allows small (about less than 500 Da), lipophilic molecules from the bloodstream to enter the CNS (Partridge, Arch Neurol. 2002; 59:35-40). Many larger therapeutic agents are prevented from reaching the brain for treating CNS disorders such as but not limited to Parkinson's disease, Alzheimer's disease, depression, stroke, and epilepsy (Partridge, NeuroRx. 2005 January; 2(1): 3-14). Disorders including autism, lysosomal storage disorders, fragile X syndrome, ataxis, and blindness, are serious disorders where there is little effective treatment. In many of these cases, the gene underlying the disease is known, but BBB delivery is the rate-limiting problem in gene therapy or enzyme replacement therapy, and no therapeutics have been developed. Drug delivery of therapeutic compounds, for example proteins, faces several challenges because of their instability, high enzymatic metabolism, low gastrointestinal absorption, rapid renal elimination, and potential immunogenicity.

There is a need for devices that can deliver compounds to the upper nasal cavity for direct nose-to-brain delivery. Certain existing nasal drug delivery devices do not adequately propel the drug from the device. Inconsistent propulsion of drug due to inconsistent user actuation is also far from optimal. Still further, the plume generated by such existing devices is too wide. Even further, some drug products do not readily mix and/or stay suspended with propellants in a MDI type device. Certain existing nasal drug devices rely on circumferential velocity to propel medicaments to the olfactory epithelium. Traditional circumferential devices result in a lower percentage of compound deposited on the olfactory epithelium. A circumferential component in the aerosol plume tends to result in a wider spray plume with a portion of the aerosol particles targeted to the sides of the nasal cavity in the lower part of the nasal cavity.

Better mechanisms for administering desired agents to the CNS (CNS; brain, brain stem, and/or spinal cord) are needed.

SUMMARY

A unit dose container for use with the POD device is described including a canister capable of containing a propellant, a diffuser in communication with the canister, a container cavity, a unit dose container capable of acceptance by the container cavity, the unit dose container in communication with the diffuser, the unit dose container capable of containing a compound, and a nozzle in communication with the unit dose container, wherein the device is capable of delivering the compound to the olfactory region of the nasal cavity.

In one aspect, the device further includes a puncture member.

In one aspect, the device further includes a front puncture member or a rear puncture member.

In one aspect, the puncture member is capable of puncturing an end of the unit dose container.

In one aspect, puncture member has an angle of puncture of 90 degrees, 60 degrees, 45 degrees, 30 degrees or 15 degrees or combinations thereof.

In one aspect, the puncture member further comprises a side orifice.

In one aspect, the compound is an intranasal formulation.

In one aspect, the unit dose container further includes a rubber stopper or a foil seal or combinations thereof.

In one aspect, the end of the unit dose container includes a puncture area.

In one aspect, the puncture area is a dimple.

In one aspect, the puncture member is metal, a polymer, Teflon or combinations thereof.

In one aspect, the unit dose container is made of a polymer or glass.

In one aspect, the polymer is polyethylene, ethyl vinyl alcohol copolymer, low-density polyethylene, high-density polyethylene, or polypropylene.

In one aspect, the unit dose container is substantially cylinder-shaped, cone-shaped, tube-shaped, rectangular-shape, polygonal, hexagonal, or oval-shaped.

In one aspect, the unit dose container is formed by injection molding, blow molding, injection blow molding, or a blow-fill-seal process.

In one aspect, the diffuser is a frit.

The invention will best be understood by reference to the following detailed description, taken in conjunction with the accompanying drawings. The discussion below is descriptive, illustrative and exemplary and is not to be taken as limiting the scope defined by any appended claims.

DESCRIPTION OF THE DRAWINGS

The foregoing aspects and many of the advantages will be more readily appreciated as the same become better understood by reference to the following detailed description, when taken in conjunction with the accompanying drawings, wherein.

FIG. 15 shows an illustration of the invention where the propellant is created by manual air compression.

FIG. 16 A shows an illustration of the device which has a compound chamber within the device body which allows for propellant flow through and around the compound chamber. FIG. 16 B shows a cross section of the device of FIG. 16 A.

FIG. 17 shows a schematic drawing of the device used to administer 2-PAM drug to rats in Example 1.

FIG. 18 demonstrates deposition testing of the POD device in the rat nasal cavity of 2-PAM (dark shading) being deposited on the olfactory region (light circle). Little drug was deposited on either the respiratory region of the nasal cavity and none was found in the trachea or esophagus.

FIG. 19 is a graph demonstrating POD administration of a 2.5 mg dose of 2-PAM that resulted in significantly lower plasma values at every point in the first 60 minutes and overall lower plasma AUC. $*=p<0.05$ FIG. 20 is a graph demonstrating POD administration of a 2.5 mg dose of 2-PAM that resulted in significantly higher brain values at 5 and 120 minutes and an overall higher brain AUC. $*=p<0.05$ FIG. 21 shows the human nasal cavity model which was used in the deposition testing of the model drug fluorescein described in Example 3.

FIG. 22 shows a processed image of human nasal cavity deposition as described in Example 3. Five separate parts, vestibule, turbinates, olfactory base, and esophagus, were analyzed for deposition after a spray of the device. FIG. 22 shows a majority of the spray to be in the olfactory region.

FIG. 23 is a schematic showing the experimental setup for the impaction testing described in Example 4.

FIG. 24 is a schematic of the experimental setup for estimating any temperature changes on a surface that the device is targeting, which is described in Example 5. A laser thermometer was used to measure the surface temperature of a target. The device sprayed either only HFA gas or HFA gas mixed with a liquid dose and any temperature fluctuations were noted.

FIG. 25 illustrates a POD device for a unit dose container.

FIG. 26 illustrates front and rear puncture members and the unit dose container.

FIG. 27 illustrates a cross section of the unit dose container with the front puncture unit and the rear puncture unit inserted.

FIG. 28 illustrates the unit dose container made of glass or a polymer with rubber stoppers FIG. 29 illustrates a side angled view of the rear puncture member.

FIG. 30 illustrates a cross section of the rear puncture member showing the distal opening along the side angle view of FIG. 29.

FIG. 31*a* illustrates a side angle view of the rear puncture member showing an orifice in the rear puncture member.

FIG. 31*b* illustrates a cross section of the rear puncture unit along the side angle view of FIG. 31*a*.

Figure 32:
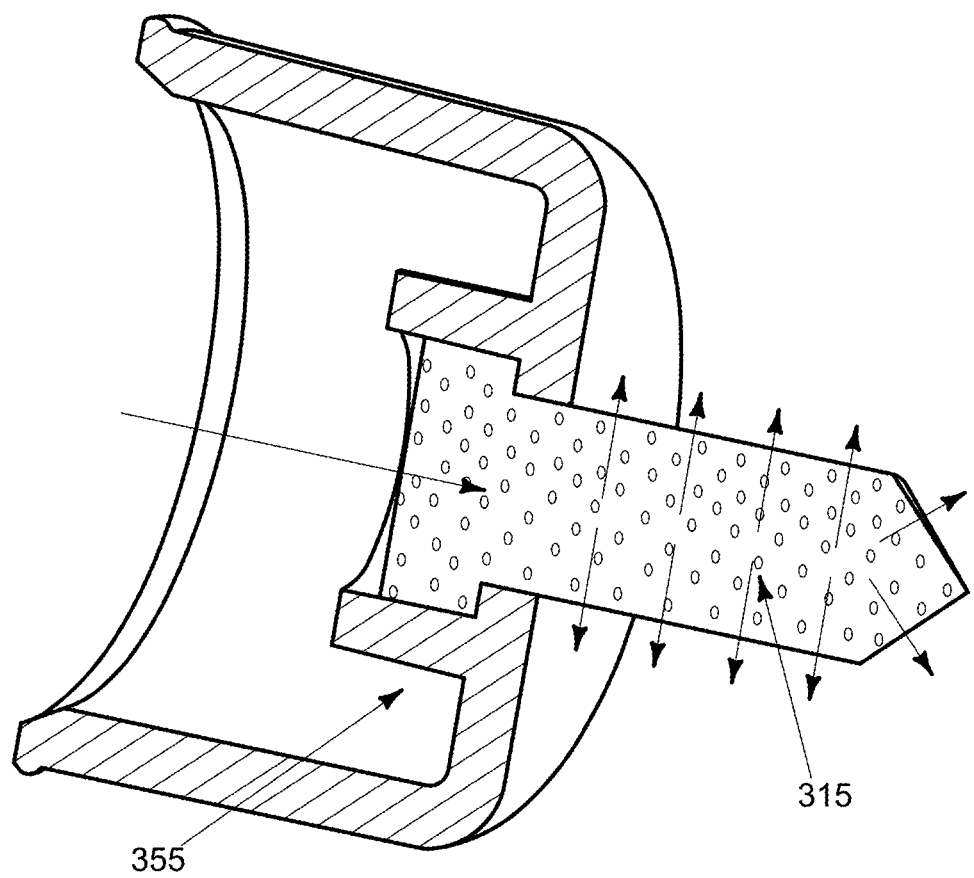

FIG. 32 illustrates a cross section of a side angle view of a porous rear puncture member.

Figure 33:
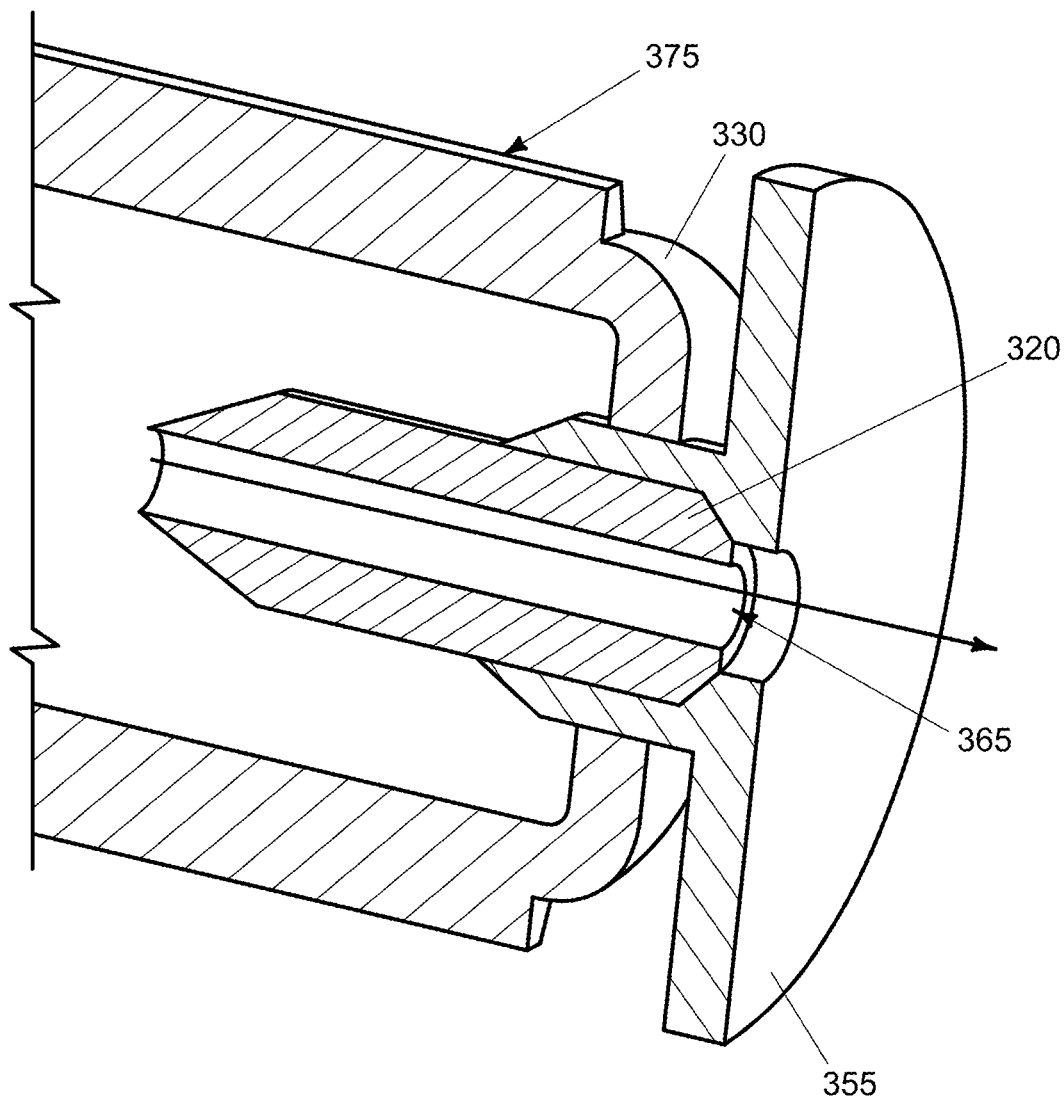

FIG. 33 illustrates a cross section of the front puncture member integral with a nozzle.

Figure 34:
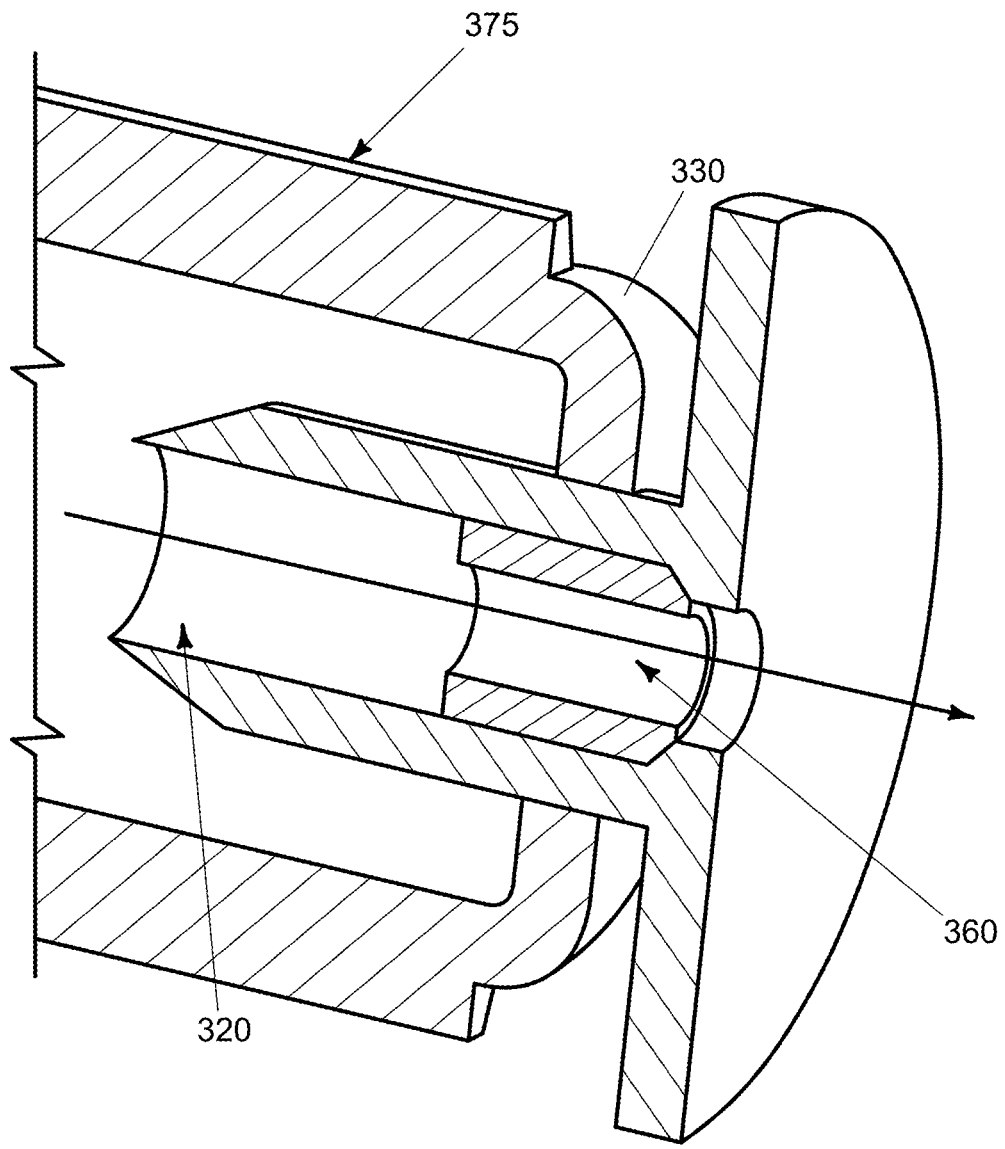

FIG. 34 illustrates a nozzle and front puncture member.

Figure 35:
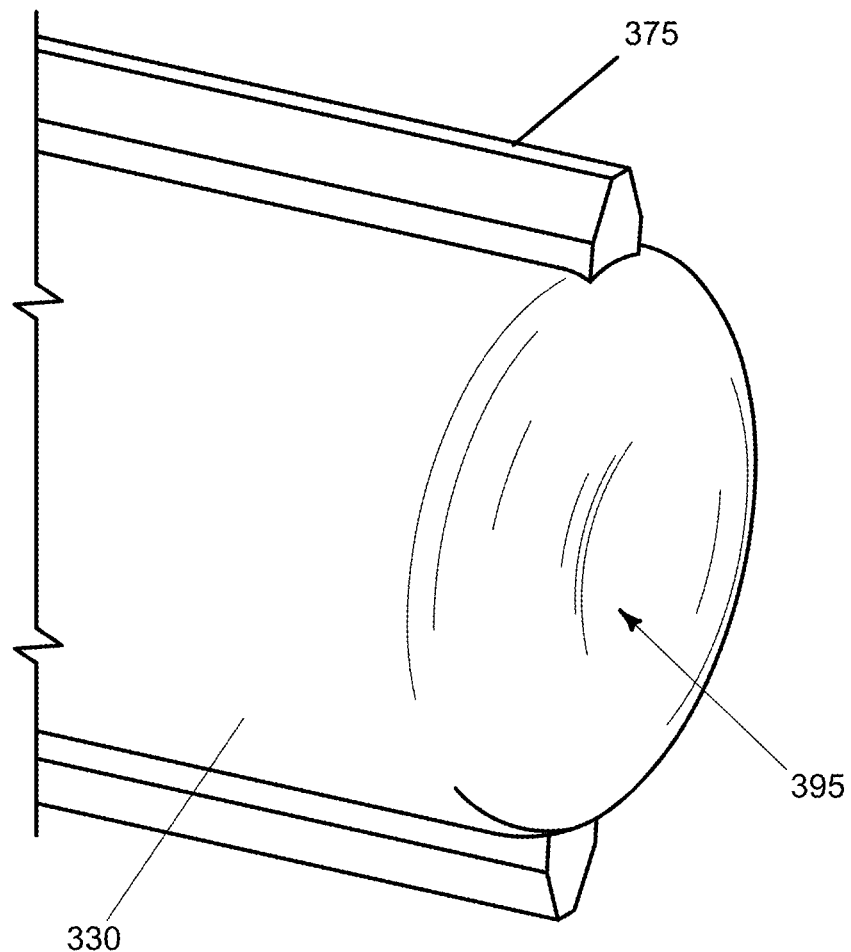

FIG. 35 illustrates a centering dimple on a unit dose container.

Figure 36:
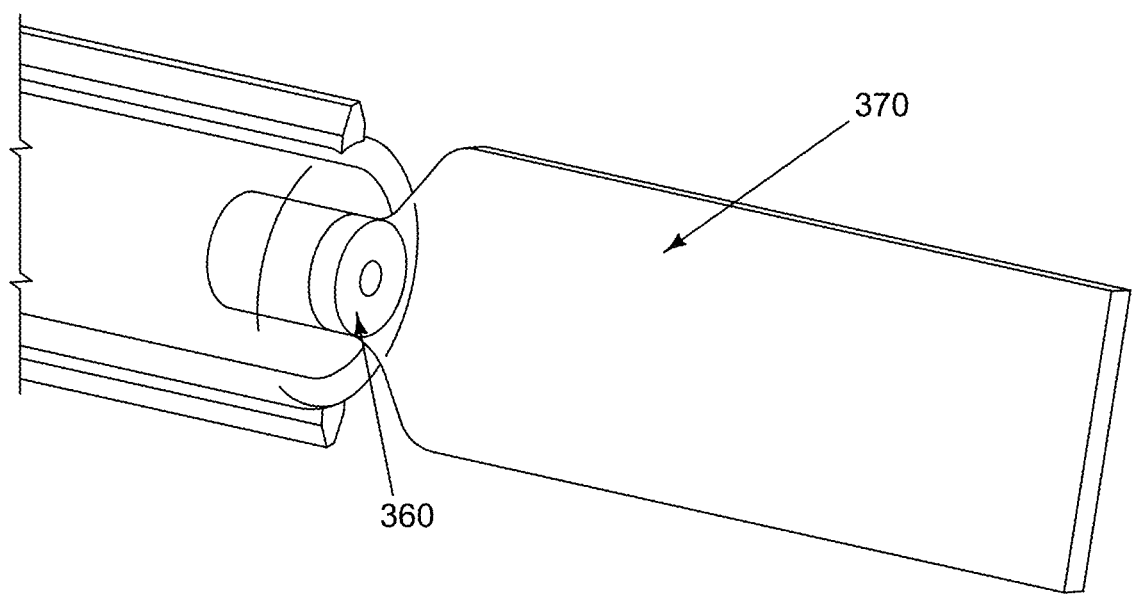

FIG. 36 illustrates a unit dose container with an overmolded nozzle.

Figure 37:
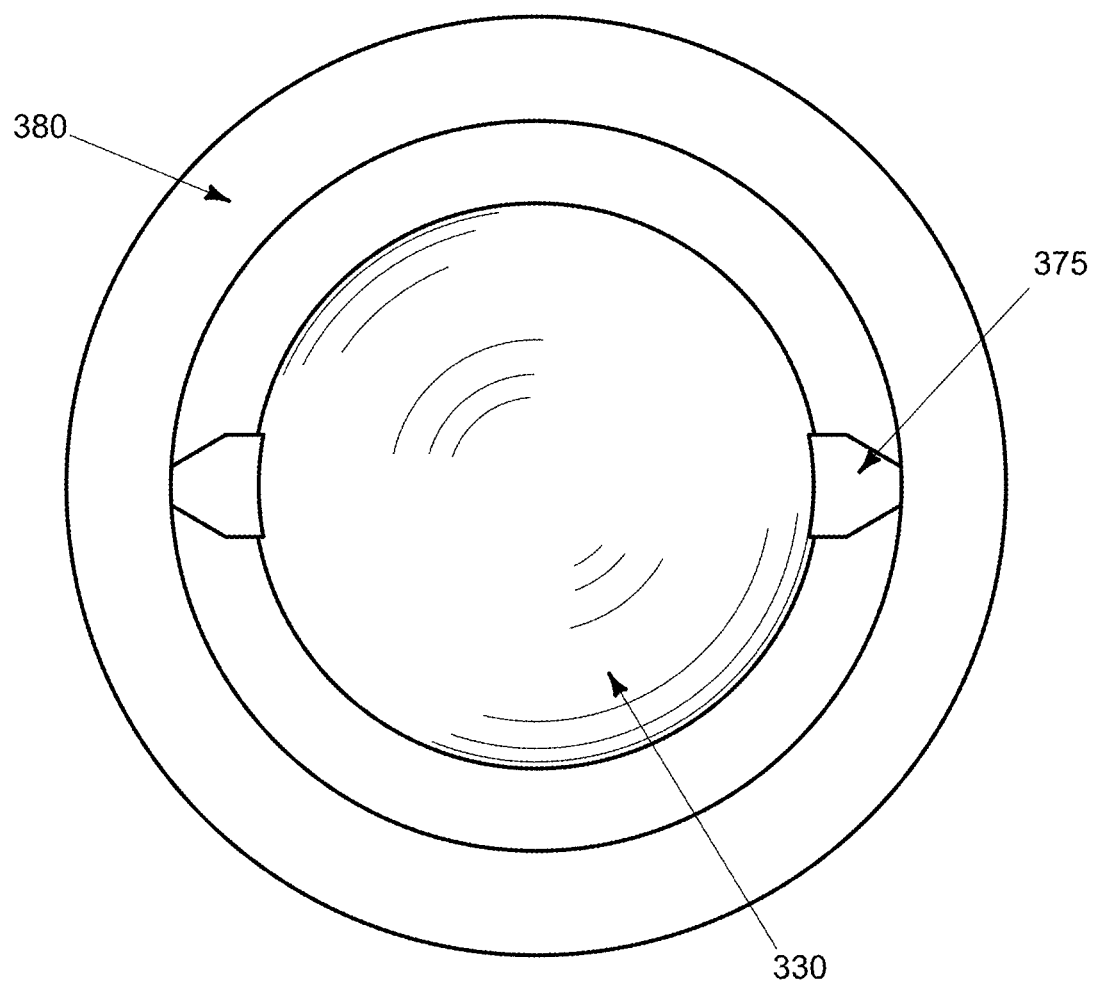

FIG. 37 illustrates an end view of a unit dose capsule including ribs contacting with the POD device.

Figure 38:
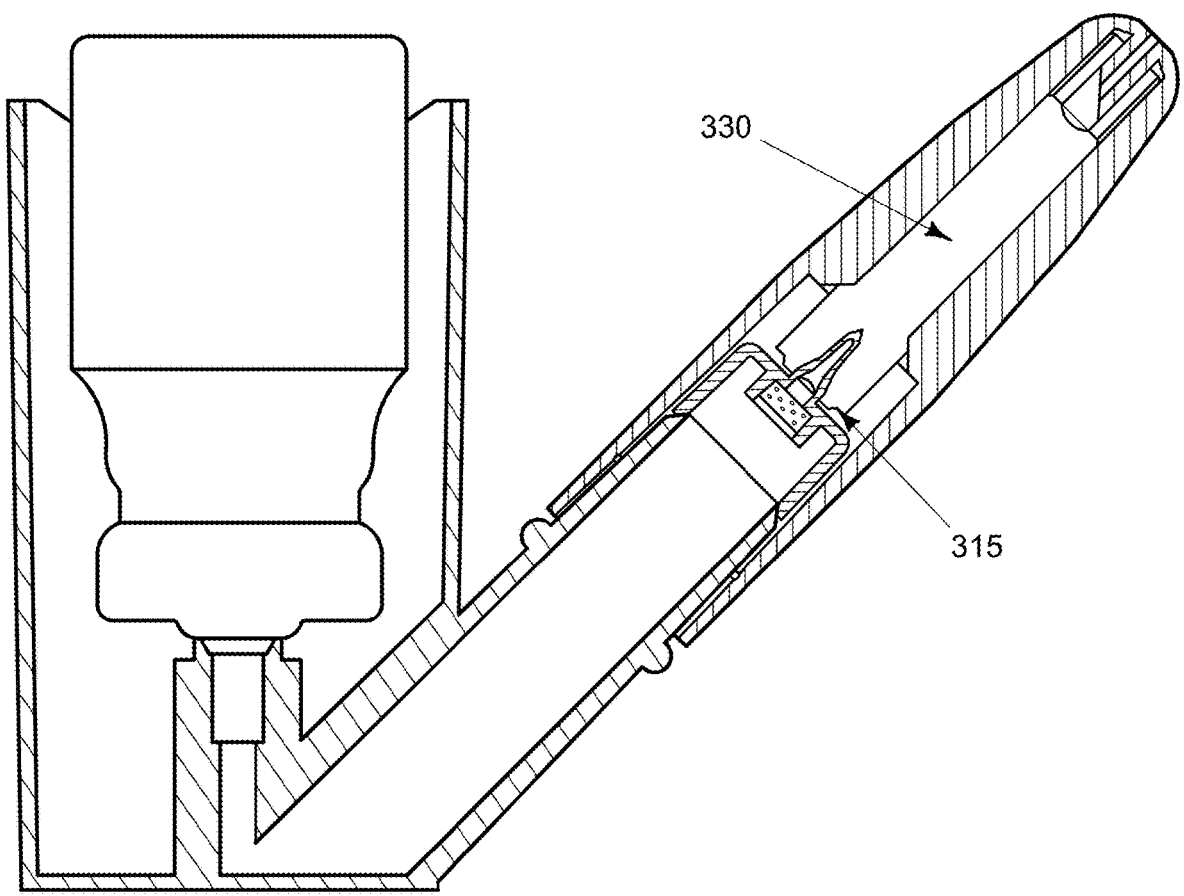

FIG. 38 illustrates a cross section of the POD device having a translational tip, partially operatively assembled, showing the rear puncture unit engaged with the unit dose container and a front puncture member.

Figure 39:
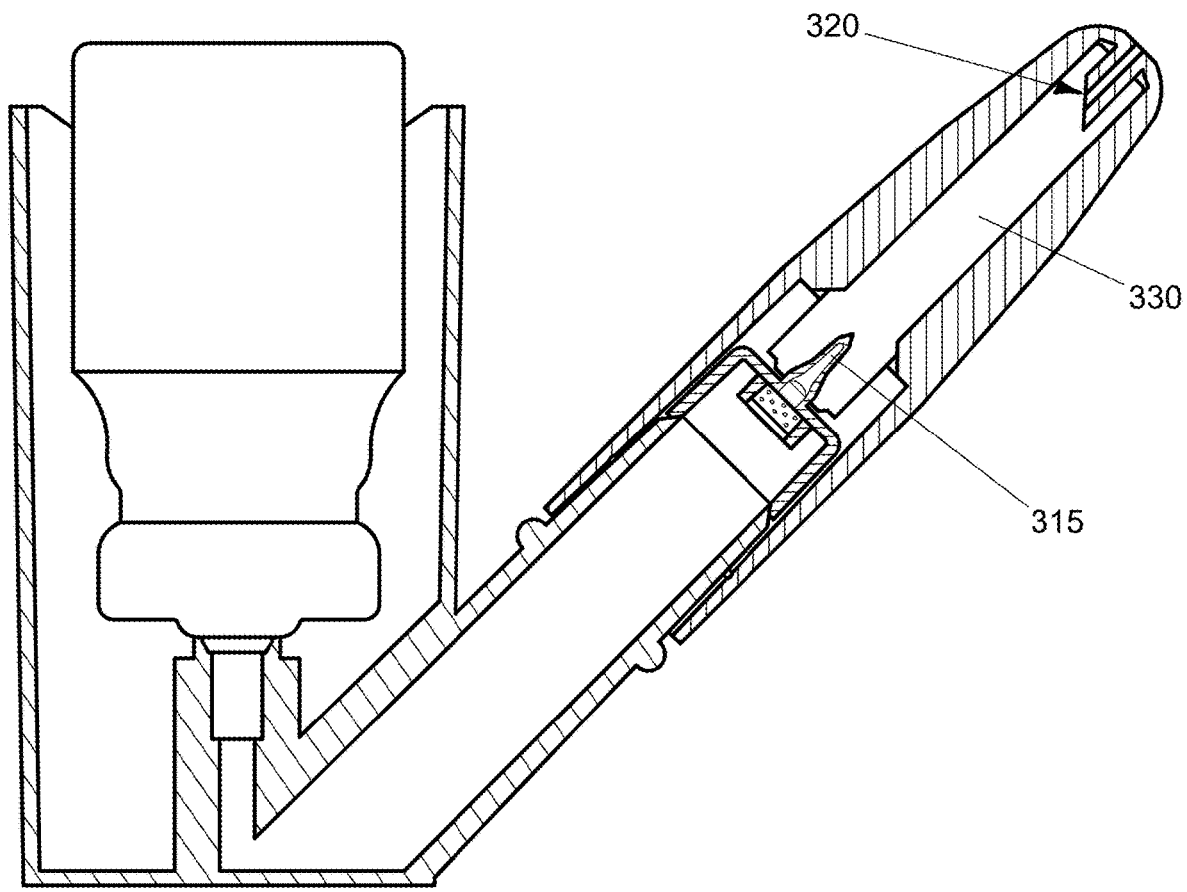

FIG. 39 illustrates a cross section of the POD device having a translational tip fully operatively assembled showing both the rear puncture member and the front puncture member engaged with the unit dose container.

Figure 40:
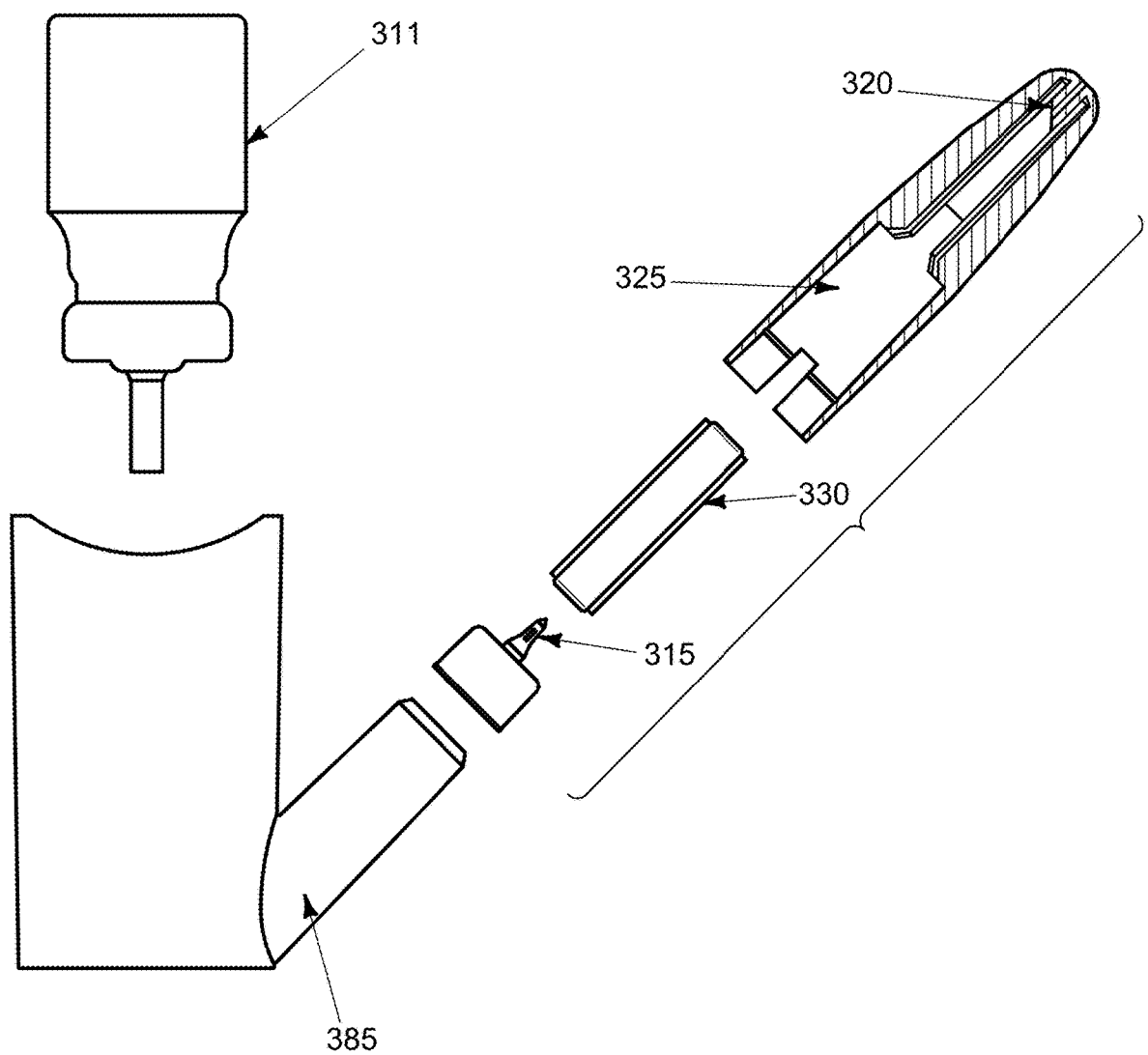

FIG. 40 illustrates an exploded view of a POD device having a translational tip with a front puncture member, a rear puncture member and a unit dose container.

Figure 41:
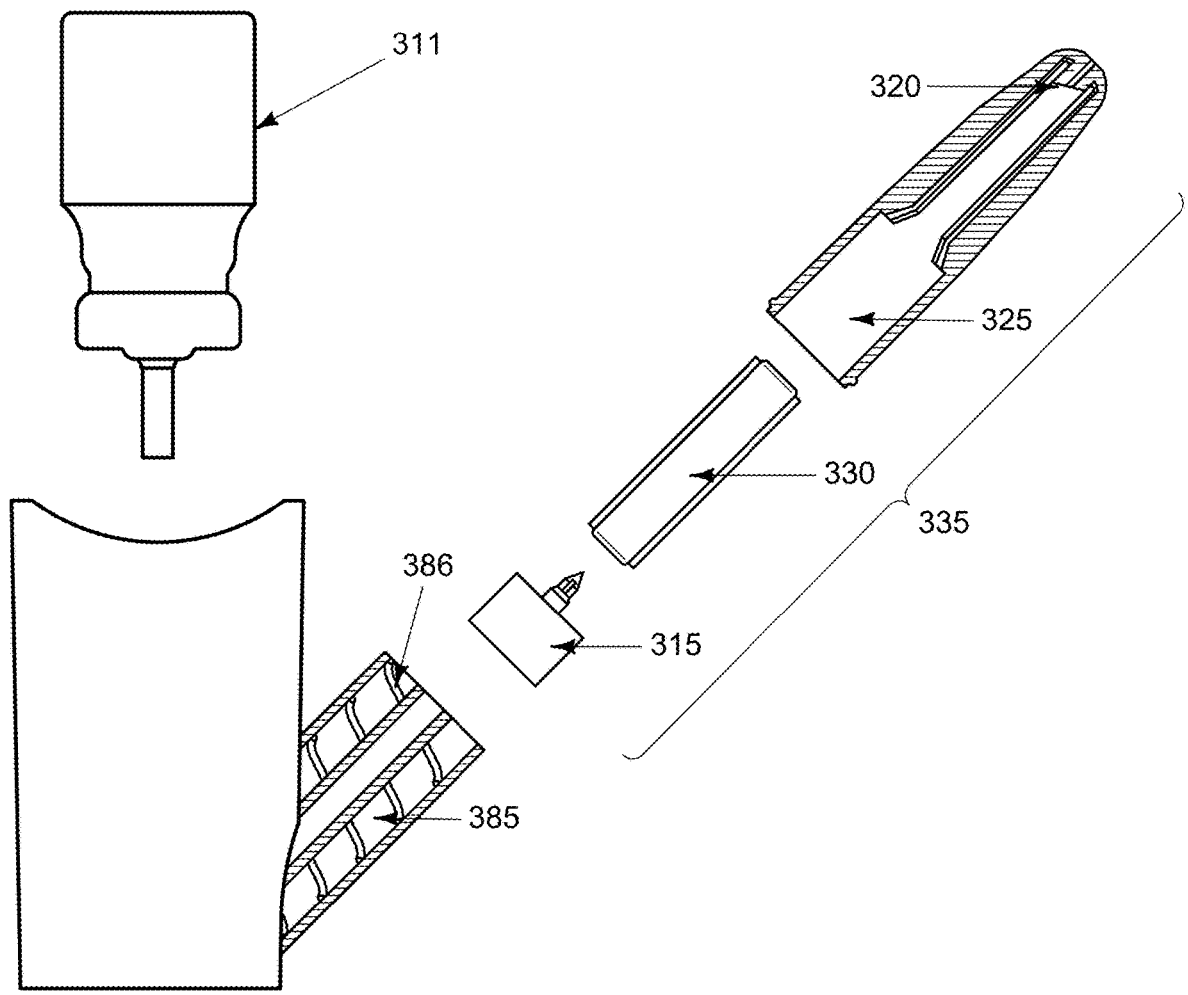

FIG. 41 illustrates an exploded view of a POD device having a rotational threaded tip with a front puncture member, a rear puncture member and a unit dose container.

FIGS. 42a-e illustrate the angle of puncture for the rear puncture member and the front puncture member.

Figure 43:
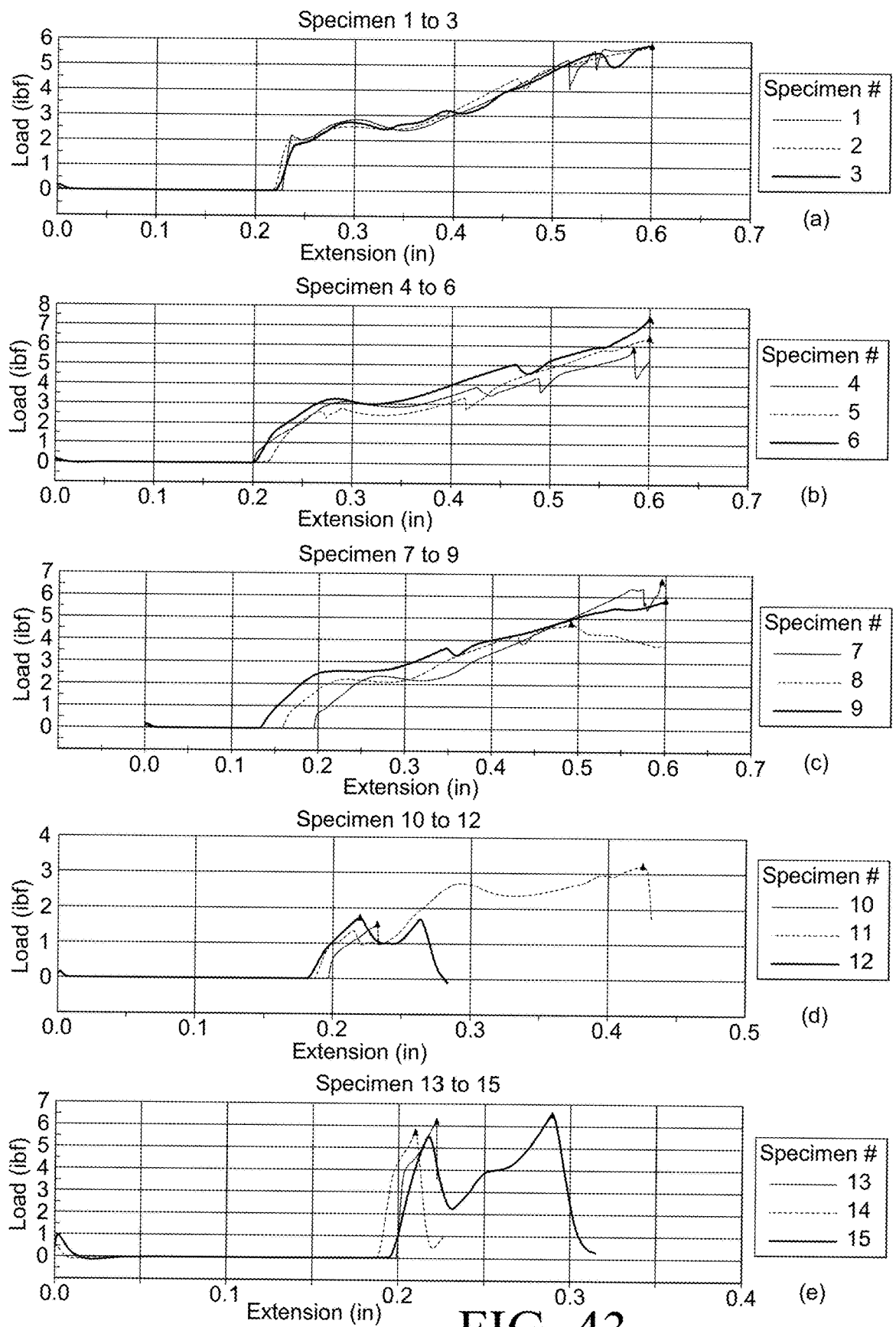

FIG. 43 shows graphs of punctures at various angles described in Example 7.

Figure 44:
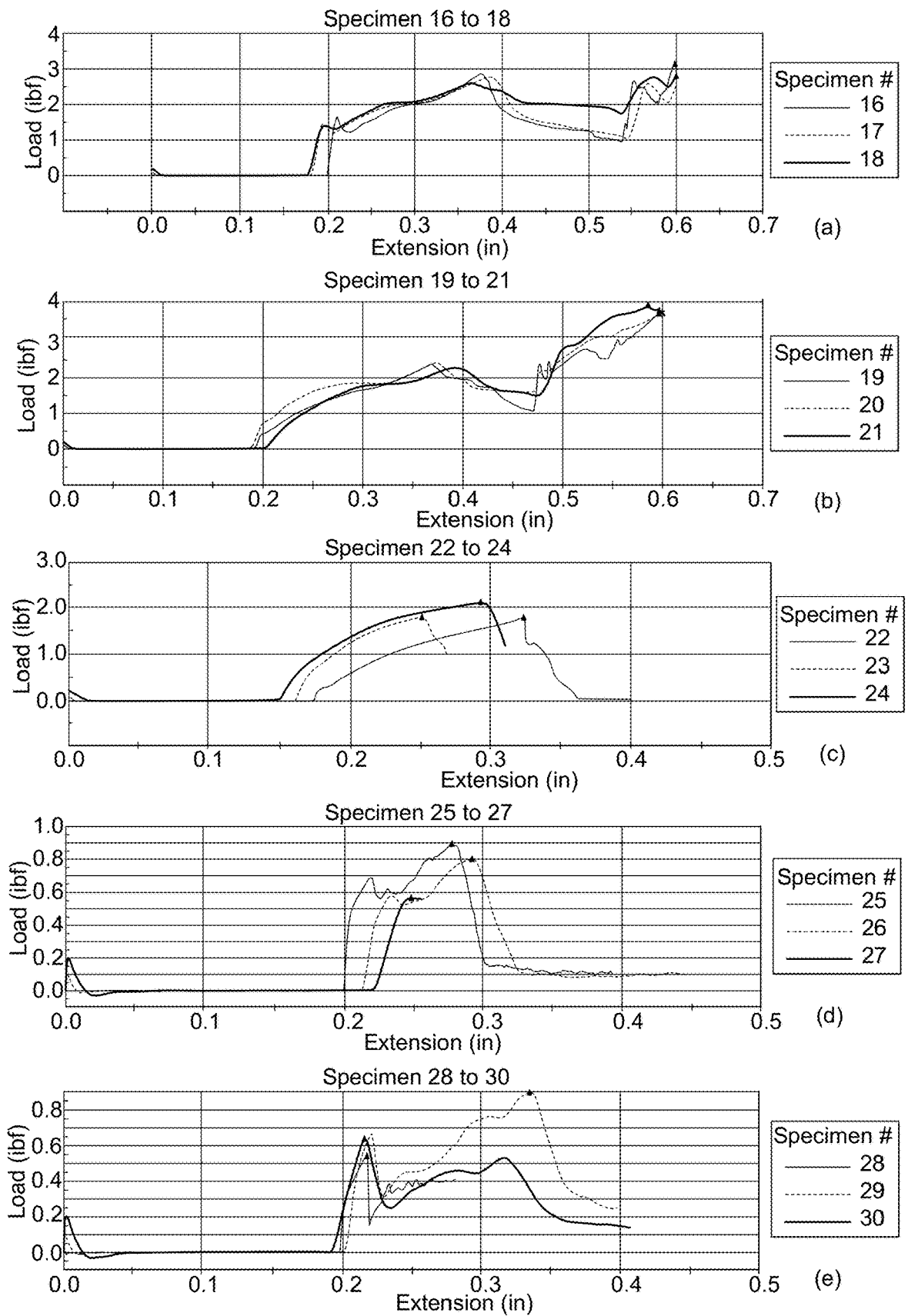

FIG. 44 shows graphs of punctures at various angles described in Example 7.

Figure 45:
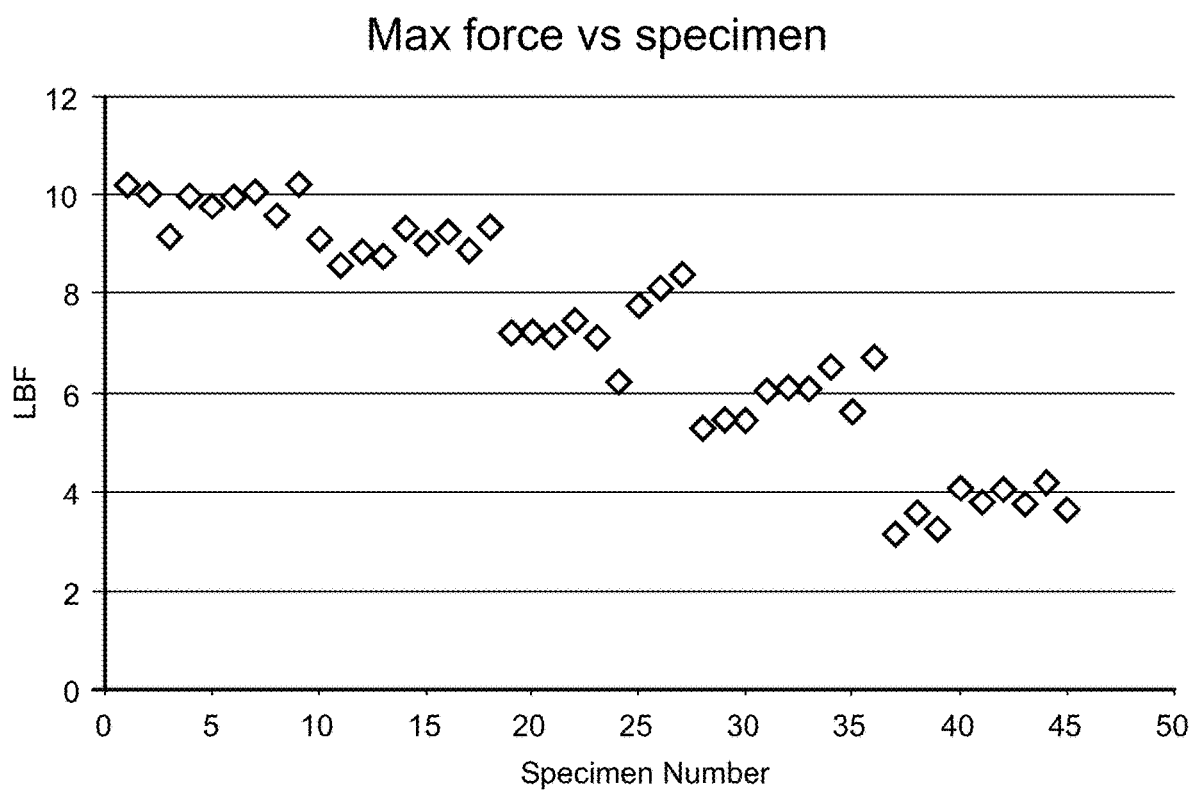

FIG. 45 shows a graph correlating the maximum force per specimen described in Example 7.

Figure 46:
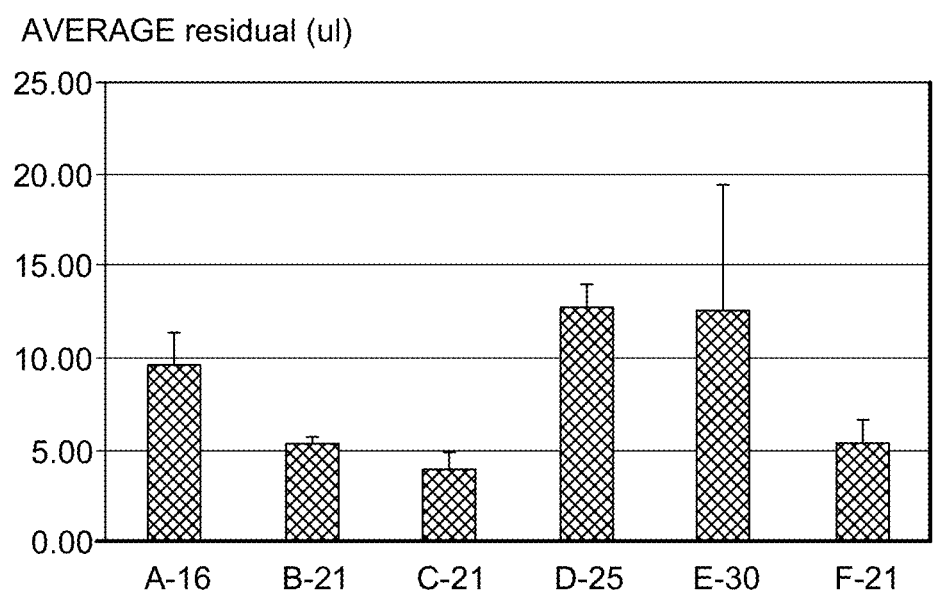

FIG. 46 shows a graph of residual drug from Example 8.

DETAILED DESCRIPTION

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise:

As used herein the specification, "a" or "an" may mean one or more.

A "diagnostic agent" refers to and encompasses an atom, molecule, or compound that is useful in diagnosing a disease. Diagnostic agents include, but are not limited to, radioisotopes, dyes, contrast agents, fluorescent compounds or molecules and enhancing agents (e.g., paramagnetic ions). A non-radioactive diagnostic agent is a contrast agent suitable for magnetic resonance imaging, computed tomography or ultrasound. The diagnostic agent can be used to perform positron emission tomography (PET), MRI, X-ray, CT, ultrasound, operative, intravascular, laparoscopic, or endoscopic procedure.

A "diffuser" refers to and encompasses a device for dispersing or deflecting a compound in various directions.

A "frit" shall refer to and encompass a porous member or filter.

An "imaging agent" refers to and encompasses an atom, molecule or compound that is useful in detecting physical changes or produces images of internal body tissues. In some aspects, the imaging agent may be a diagnostic agent.

A "propellant" shall refer to and encompass a compound that acts as a vehicle for creating propulsion or thrust.

As used herein, the term "puncture" or "puncturing" refers to any form of opening, including piercing, perforating and tearing.

The term "therapeutically effective amount" or "effective dose" refers to and encompasses an amount of a drug effective to treat a disease or disorder in a mammal. In one aspect, the therapeutically effective amount or effective dose refers to a target CNS concentration that has been shown to be effective in, for example, slowing disease progression. Efficacy can be measured in conventional ways, depending on the condition to be treated.

The term "treatment" and "treat", and the like, refers to and encompasses therapeutic or suppressive measures for a disease or disorder leading to any clinically desirable or beneficial effect, including, but not limited to, alleviation or relief of one or more symptoms, regression, slowing or cessation of progression of the disease or disorder. Treatment can be evidenced as a decrease in the severity of a symptom, the number of symptoms, or frequency of relapse.

A "user" or "subject" shall refer to and encompass a human or other animal. For example, the animal may be a primate or a non primate and may include a rabbit, bovine, equine, pig, rat, mouse, dog or cat.

The device may be used in treatment, prevention, palliative care for humans and veterinary purposes. The device may be used in research and industrial uses. For example, the device may be used to deposit compound in agricultural settings.

When trade names are used herein, applicants intend to independently include the trade name product formulation, the generic drug, and the active pharmaceutical ingredient(s) of the trade name product.

For clarity of disclosure, and not by way of limitation, the detailed description is divided into the subsections which follow.

Nasally administered compounds contact the upper olfactory region and molecular transport occurs directly across this tissue and into compartments of the central nervous system. (Henry, R. J., et al., Pediatr Dent, 1998. 20(5): p. 321-6; Sakane, T., et al., J Pharm Pharmacol, 1991. 43(6): p. 449-51; Banks, W. A., et al., J Pharmacol Exp Ther, 2004. 309(2): p. 469-75; Westin, et al., Pharm Res, 2006. 23(3): p. 565-72). The olfactory mucosa is located in the upper nasal cavity, just below the cribriform plate of the skull. It contains olfactory cells which traverse the cribriform plate and extend up into the cranial cavity. When compounds come in contact with this specialized mucosa, they are rapidly transported directly into the brain, they bypass the BBB, and are rapidly transported directly into the central nervous system, often faster than if the compound is given intravenously.

The olfactory mucosa includes the olfactory epithelium. The olfactory epithelium is located at the top of the nose between the superior turbinate and the roof of the nasal cavity, just beneath the cribriform plate of the ethmoid bone. In humans, it covers about 10 to about 20 cm2, or about 8% of the total nasal surface area, and is composed of four main cell types: epithelial cells, olfactory receptor neurons, supporting cells, and basal cells. (Mathison S. et al., (1998) Journal of Drug Targeting 5: 415-441). Although 3% of the nasal cavity is occupied by olfactory epithelium (Morrison and Costanzo, Morphology of the human olfactory epithelium, J Comp Neurol. 1990 Jul. 1; 297(1):1-13), this route is direct, since the olfactory neurons do not have a synapse between the receptive element and the afferent path (Ding X, Dahl A R. Olfactory mucosa: composition, enzymatic localization and metabolism. In: Doty R, editor. Handbook of Olfaction and Gustation. New York: Marcek Dekker; 2003).

The olfactory epithelium is more than twice the depth of the respiratory epithelium, with the olfactory nerve cell bodies typically located in the middle and deeper regions of the epithelium while nuclei of the supporting cells are organized in a single layer closer to the mucosal surface. Tight junctions exist between the supporting cells and between the supporting cells and olfactory nerve cells. Morrison E. E, et al. (1992) Journal of Comparative Neurology 297(1): 1-13.

When a nasal drug formulation is delivered deep and high enough into the nasal cavity, the olfactory mucosa is reached and drug transport into the brain and/or CSF via the olfactory receptor neurons occurs. The transfer of compounds from the nose to the brain is referred to as the nose-brain pathway. The nose-brain pathway has implications when centrally acting medications such as but not limited to sedatives, anti-seizure drugs and opiates are delivered nasally. The present device allows for delivery via the nose-brain pathway allowing for nearly immediate delivery of nasal medications to the central nervous system and brain, by-passing the blood brain barrier.

The current challenge in nose-to-brain drug delivery is also due to the complex architecture of the nose, which is naturally designed to channel drugs into the lower nasal airway toward the lungs making it difficult for drugs to reach the olfactory region. Most of the drug dispensed from traditional nasal devices such as sprayers or pumps is subjected to the natural air movement in the nasal cavity towards the esophagus. The majority of the spray dispensed from traditional devices encounters the natural downward airflow displacement within the nasal cavity. The remaining fraction from traditional devices is found in the respiratory epithelium and cleared by the mucocilliary clearance mechanism or absorbed into the blood stream. While nasal catheter instillation and nose drops are less impacted by this natural downward air movement, it requires subjects to be in a supine position, is often associated with user discomfort, and is not optimal for frequent clinical administration.

Moreover, a reservoir of residual air exists at the top of the nasal cavity that is not removed during normal respiration; thus remaining in the olfactory region and acting as a barrier to deposition. This residual air must be displaced in order to deliver aerosolized drug to the olfactory epithelium in the upper nasal cavity in a consistent manner. The device described herein delivers a majority of the aerosolized drug to the upper part of the nasal cavity to increase exposure of the drug at the olfactory epithelium, a site of nose-to-brain pathway, by both avoiding the natural downward air movement and displacing the residual air of the upper nasal cavity.

The device herein advantageously and consistently deposits a large fraction of dose into the more distal parts of the nasal cavity such as the olfactory region. A drug product (also referred to herein as drug formulation or nasal dosage form) is propelled from the device with a velocity into the nasal cavity.

Figure 1:
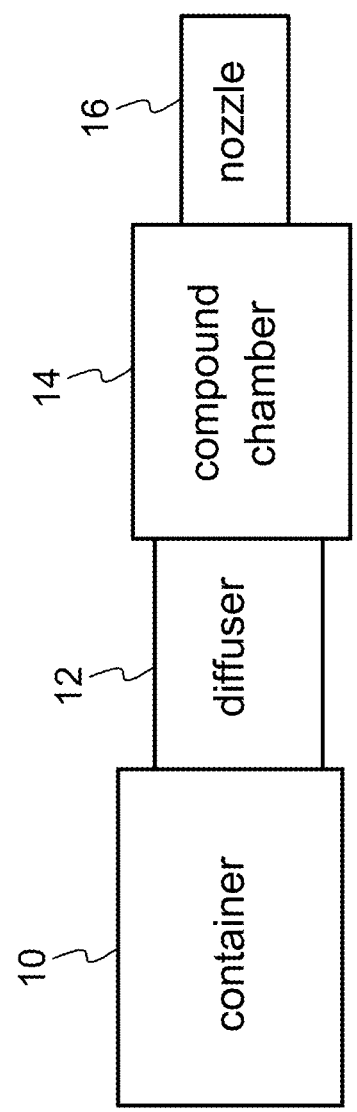
FIG. 1 is a schematic drawing of one embodiment of the invention.

FIG. 1 shows one embodiment of the device where a container 10 contains a propellant. The propellant may be pressurized. The propellant is a fluid, for example, a liquid or gas. In one aspect, the propellant is a liquid. In another aspect, the propellant is a gas. Propellants include pharmaceutically suitable propellants. Some examples of pharmaceutically suitable propellants include hydrofluoroalkane (HFA) including but not limited to HFA, HFA 227, HFA 134a, HFA-FP, HFA-BP and the like HFA's. In one aspect, the propellant is liquid HFA. In another aspect, the propellant is gaseous HFA. Additional examples of suitable propellants include nitrogen or choloroflourocarbons (CFC). Additionally, propellants may be pressurized air (e.g. ambient air). The container 10 may be a conventional metered dose inhaler (MDI) device that includes a pressurized canister, metering valve (including stem) to meter the propellant upon actuation. In certain aspects, the propellant is not metered upon actuation. In one aspect, the container 10 does not contain drug. In another aspect, the container includes a propellant and a drug.

The container 10 is in communication with a diffuser. For example, when the diffuser is in communication with the container 10, "communication" shall refer to and encompass congruousness or fluid communication. The propellant from the container 10 is diffused via the diffuser. In one aspect, a majority of the propellant is diffused via the diffuser. In another aspect, a minority of the propellant is diffused via the diffuser. Majority refers to and encompasses at least 50 percent. Minority refers to and encompasses less than 50 percent. In another aspect, at least about 10%, 15%, 20%, 25%, 30%, 35%, 40%, 45%, 50%, 55%, 60%, 65%, 70%, 75%, 80%, 85%, 90%, 95%, 99% or about 100%, inclusive of endpoints, of the propellant is diffused via the diffuser. The diffuser is in communication with the compound chamber 14. The compound chamber 14 is capable of holding a compound, such as but not limited to a drug or/and a diagnostic agent. In one aspect, the diagnostic agent is an imaging agent. In an example, the imaging agent is fluorodeoxyglucose (FDG) or fluorothymidine (FLT). In another aspect, the compound is a drug. In another aspect, the compound is not an imaging agent. In one aspect, the compound is a liquid. In another aspect, the compound is a powder. In yet another aspect, the compound is an intranasal formulation of a drug in a liquid or powdered state. The intranasal formulation may contain suitable intranasal carriers and excipients known in the art.

The propellant in the container 10 acts as a vehicle to deliver propulsion or thrust to expel from the compound chamber 14 the compound. The compound chamber 14 is in communication with a nozzle 16. The propulsion or thrust from the propellant is capable of expelling the compound from the compound chamber 14 and nozzle 16 when in communication with the compound chamber 14.

In one aspect, when the MDI device is actuated, a discrete amount of pressurized HFA fluid is released. The MDI may contain between about 30 to about 300 actuations, inclusive of endpoints, of HFA propellant. The amount of fluid propellant released upon actuation may be between about 20 and about 200 µl, inclusive of endpoints, of liquid propellant.

Figure 2:
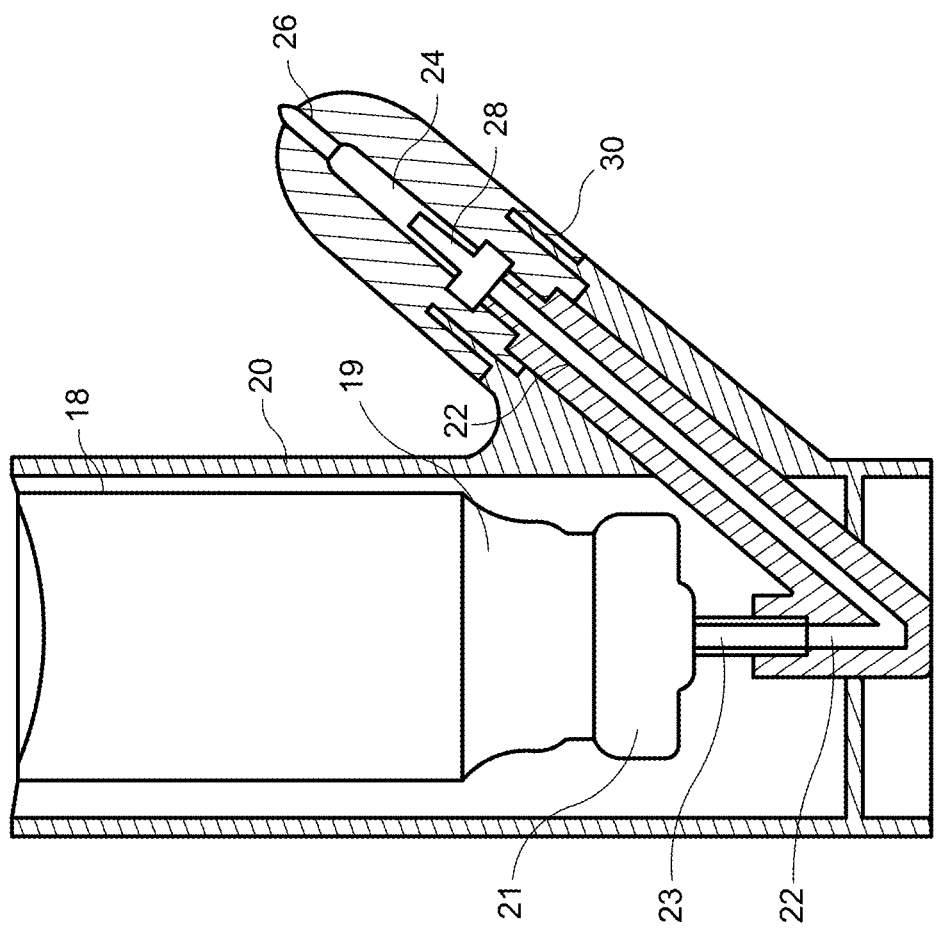
FIG. 2 shows another illustration.

FIG. 2 shows one embodiment of the device. The actuator body 20 houses a container 10, in one aspect the container 10 is a metered dose inhaler that includes a propellant canister 18 having a neck 19 and a metering valve assembly 21. A valve stem 23 is in communication with a connection channel 22. The propellant exiting the valve stem 23 is a fluid. The fluid may be liquid, gas, or a combination. A diffuser 28 is in communication with the propellant exiting the container 10 and the compound chamber 14.

Propellant exiting the container 10 comes into contact with the diffuser 28. The diffuser 28 is capable of converting liquid propellant exiting the container 10 into gaseous propellant. In one aspect, the diffuser 28 is capable of converting all or a majority of the liquid propellant into gaseous propellant. In another aspect, the diffuser is capable of converting a minority of the liquid propellant into gaseous propellant. Majority refers to and encompasses at least 50 percent.

Minority refers to and encompasses less than 50 percent. In another aspect, at least about 10%, 15%, 20%, 25%, 30%, 35%, 40%, 45%, 50%, 55%, 60%, 65%, 70%, 75%, 80%, 85%, 90%, 95%, 99% or about 100%, inclusive of endpoints, of the liquid propellant is converted into gaseous propellant. Following contact with the diffuser 28, the diffused propellant comes into contact with the compound in the compound chamber 14. The diffused propellant and the compound come into contact with each other as the propellant propels the compound in the compound chamber 114. The nozzle 16 is in fluid communication with the compound chamber 14. The compound is propelled by the diffused propellant into communication with the nozzle 16. The propellant propels the compound to be expelled via the distal end of the nozzle 16. Exiting from the nozzle 16 is compound, propellant, or a combination thereof.

In some aspects, the diffuser 28 functions to convert propellant from a liquid to a gas. In other aspects, the diffuser 28 functions to prevent the compound contained in the compound chamber 14 from coming in contact with the container 10. In another aspect, the diffuser acts as a one way check valve. In other aspects, the diffuser 28 functions to convert propellant from a liquid to a gas and to prevent the compound contained in the compound chamber 14 from coming into contact with the container 10. In yet another aspect, the diffuser functions to increase the temperature of the propellant.

An example of a diffuser 28 includes a frit, a plurality of frits, or a diffuser member or combinations thereof. In one aspect, the diffuser is a frit. In another aspect, the diffuser is a plurality of frits. In another aspect, the diffuser is a diffuser member.

In one aspect, the frit(s) are of any suitable size and shape and are formed using any suitable porous material of any suitable density. In one aspect, the frit is made of a hydrophobic material. In one aspect, the frit is made of an inert material to avoid chemically reacting with any of the compounds. The inert material may be metal or non metal. In one aspect, the frit is composed of metal. In another aspect, the frit is composed of a non-metal. In one aspect, the inert material is sintered nickel. As one example, a frit formed using a porous stainless steel having a pore size in the range of approximately 1 micron to approximately 100 microns can be used. In another aspect the pore sizes is in the range of about 1 to about 10, about 10 to about 20, about 20 to about 30, about 30 to about 40, about 40 to about 50, about 50 to about 60, about 60 to about 70, about 70 to about 80, about 80 to about 90, about 90 to about 100 microns, inclusive of endpoints. In another aspect, the frit can be formed using aluminum foam. The number and size of the pores and the overall dimensions (e.g., diameter and thickness) of the frit are set to maximize surface area for vaporization while limiting pressure drops accompanying passage of vaporized propellant through the frit. In certain aspects, the frit may be constructed of Teflon, glass, metal mesh, screen, porous metal, polyether ether ketone or another plastic material. In one aspect, the passage of liquid propellant through the increased surface area of the frit transitions the liquid to gas and increases the temperature of the resulting gas. In another aspect, the passage of gas propellant through the increased surface area of the frit increases the temperature of the gas.

As shown in FIG. 2, in one aspect, the diffuser 28 is disposed on the connection channel 22. In another aspect, the diffuser 28 is disposed within a drug chamber 24 whereby an intranasal dosage form is disposed in the drug chamber 24. A nozzle 26 is in communication with the drug chamber 24. The diffuser 28, drug chamber 24 and nozzle 26 are housed by a drug capsule 30 adjacent the actuator body 20.

The drug capsule body 30 may be of any suitable material to house the components. In one aspect, the drug capsule body 30 may be constructed from plastic. In one aspect, the drug capsule body 30 may taper at the distal end to allow the nozzle 26 to be brought closer to the septum. The taper functions to improve the positioning of the device at a suitable horizontal angle relative to the upper nasal cavity.

Figure 3:
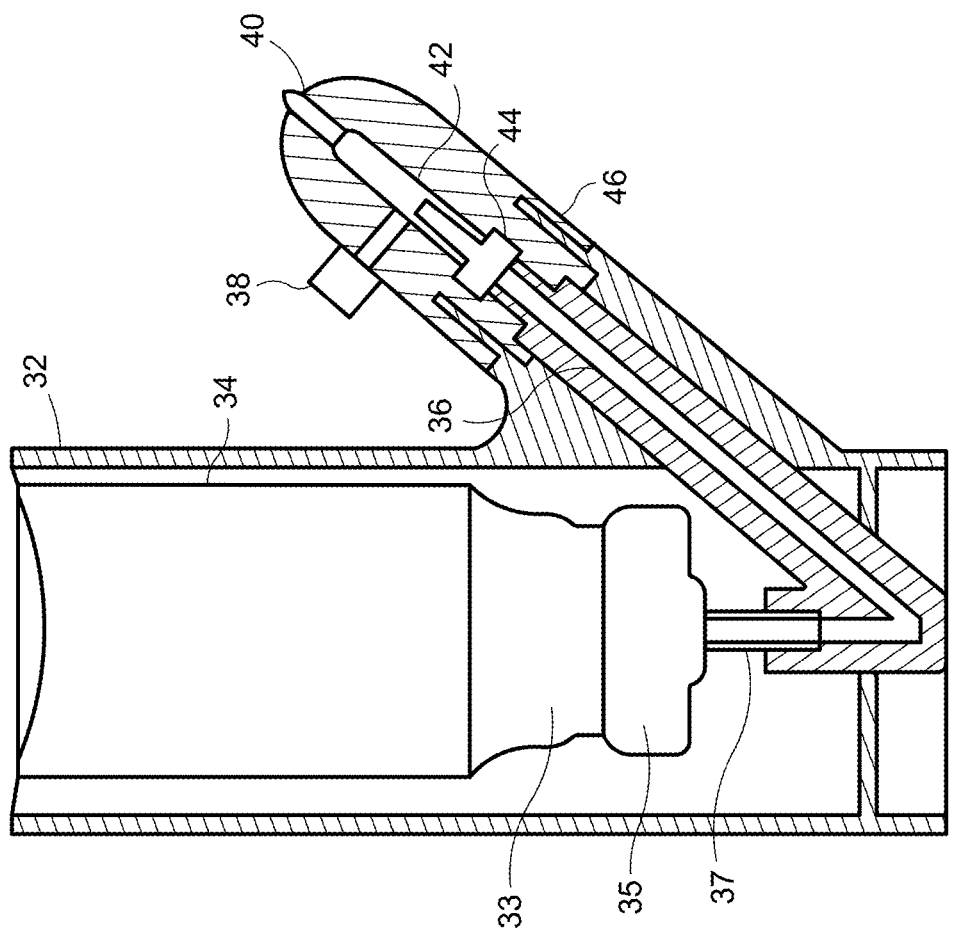
FIG. 3 shows another illustration.

Shown in FIG. 3 is another embodiment of the device. The actuator body 32 (or, housing) houses the propellant canister 34 having a neck 33 and a metering valve assembly 35. A valve stem 37 is disposed within a connection channel 36. The propellant exiting the valve stem 37 is in a liquid form or a mixture of liquid and gaseous form. A diffuser 44 is disposed on the channel 36 and is adapted to convert a majority or all of the liquid propellant into gaseous propellant. The diffuser 44 is disposed within a drug chamber 42, whereby the intranasal dosage form is disposed in the drug chamber 42. A nozzle 40 is in communication with the drug chamber 42. The diffuser 44, drug chamber 42 and nozzle 40 are disposed within a drug capsule 46 adjacent the actuator body 32.

An insertion port 38 is provided for the insertion of a compound into the drug chamber 42. The insertion port 38 may be constructed from silicone or plastic. In one aspect, the needle of a syringe may be inserted through the insertion port 38 so as to inject the compound into the drug chamber 42. In one aspect, the compound is a drug. In another aspect, the compound is a diagnostic agent. In yet another aspect, the compound is not an imaging agent. The drug may be a liquid or a powder.

Figure 4:
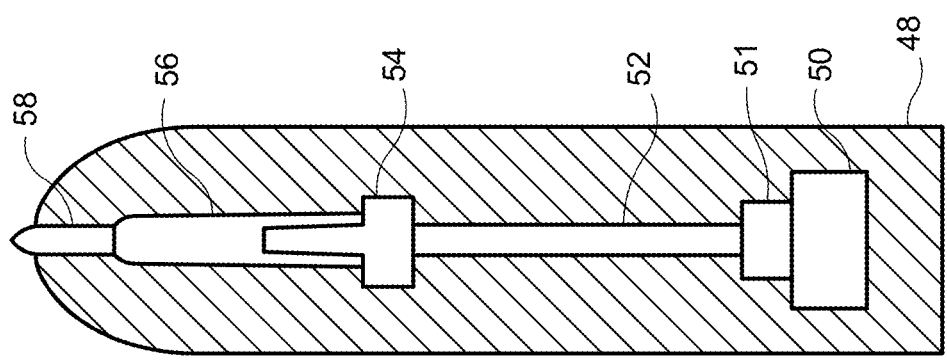
FIG. 4 shows another illustration.

Shown in FIG. 4 is another embodiment of the device. A housing body 48 houses a pressurized propellant container 50, a connection channel 52, a release valve assembly 51, a diffuser 54, a drug chamber 56 and a nozzle 58. The pressurized propellant container 50 contains a liquid propellant and has a release valve assembly 51. A connection channel 52 is congruous with the release valve assembly 51 of the container 50 and a diffuser 54. The diffuser 54 is in communication with a drug chamber 56. In one aspect, the drug chamber contains a drug-containing intranasal dosage form. A nozzle 58 is in communication with the drug chamber 56.

Figure 5:
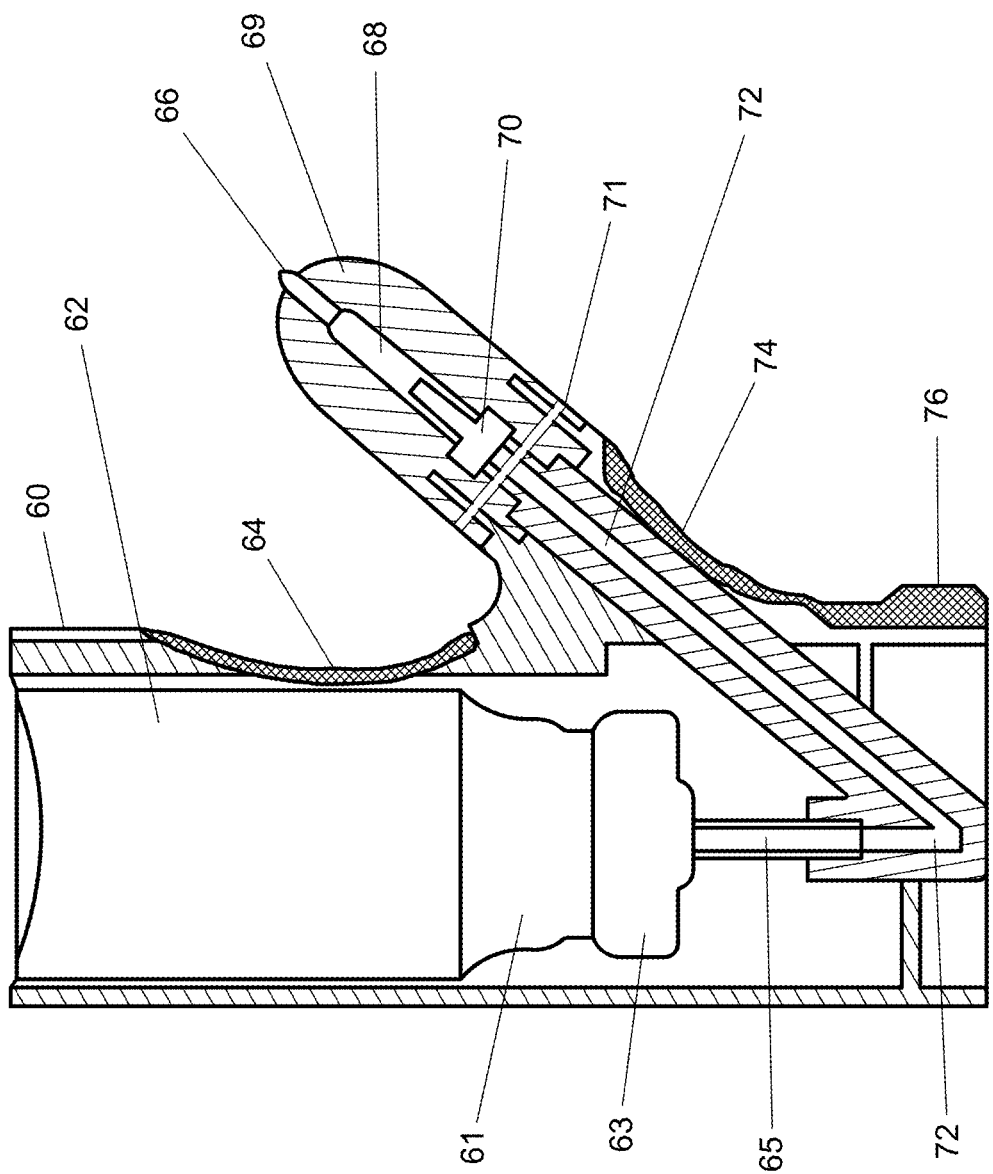
FIG. 5 shows another illustration.

Shown in FIG. 5 is another embodiment of the device. An actuator body 60 houses a propellant container 62 having a neck 61, a metering valve assembly 63 and valve stem 65. A valve stem 65 is disposed within a connection channel 72. The propellant exiting the valve stem 65 is in a liquid form, gaseous form, or a mixture of liquid and gaseous form. A diffuser 70 is disposed on the channel 72 and is adapted to convert the liquid propellant into gaseous propellant. The diffuser 70 is in communication within a drug chamber 68. In one aspect, the drug chamber 68 contains an intranasal dosage form. A nozzle 66 is in communication with the drug chamber 68. The diffuser 70, drug chamber 68 and nozzle 66 are disposed within a drug capsule 69 adjacent to the actuator body 60. The actuator body 60 is shaped allowing or accommodating for an aiming guide. The aiming guide includes one, a plurality, or all of the nose-aiming guide 64, the septum-aiming guide 74, an upper lip aiming guide 76, and a visual indicator 71.

In one aspect, a nose-aiming guide 64 is provided on the actuator body 60. The nose-aiming guide 64 functions to accommodate the user's nose. In another aspect, the nose-aiming guide 64 functions to aim the nozzle 66 at the user's olfactory region.

In another aspect, a septum-aiming guide 74 is provided on the actuator body 60. In one aspect, the septum-aiming guide 74 functions to accommodate contacting the user's septum.

In yet another aspect, an upper lip aiming guide 76 is provided on the actuator body 60. The upper lip aiming guide 76 functions to accommodate contacting the user's upper lip. In one aspect, a visual indicator 71 is provided to alert the user to the length or amount of the capsule's 70 insertion into the user's nasal cavity. In one aspect, the visual indicator 71 is inserted to a specified amount or length into the user's nasal cavity.

Figure 6:
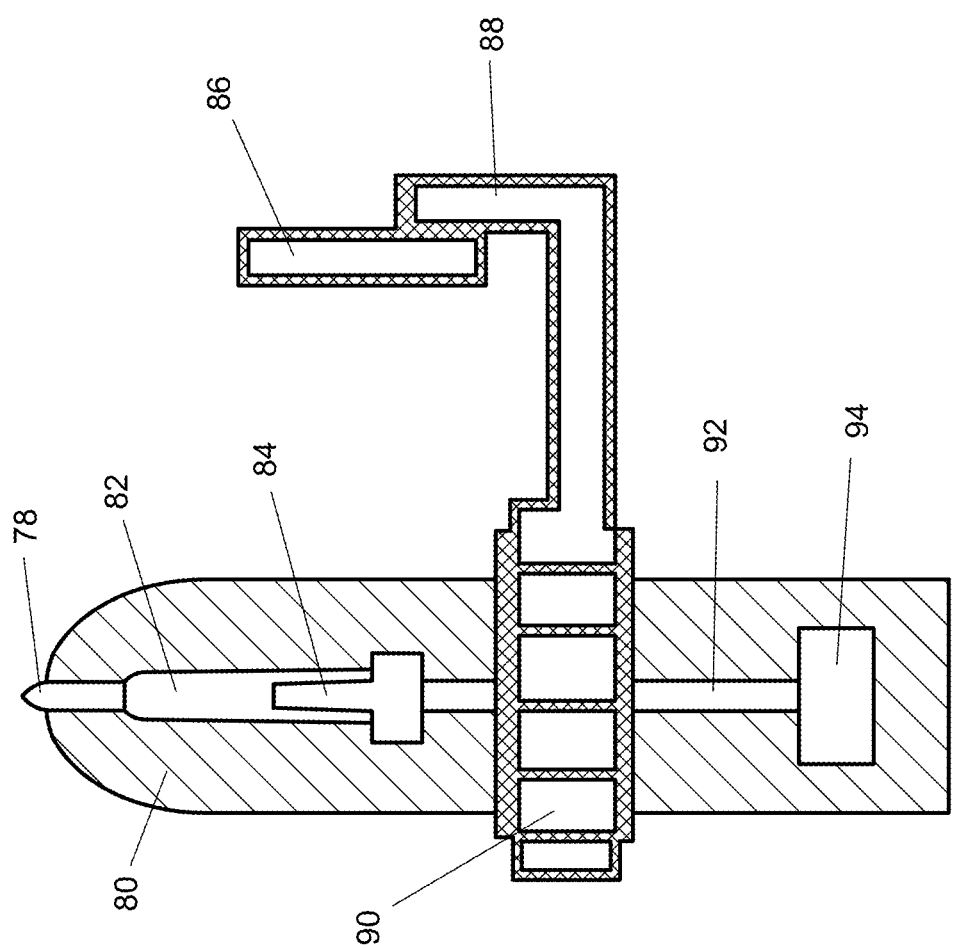
FIG. 6 shows another illustration.

Shown in FIG. 6 is another embodiment of the device. A housing body 80 houses a pressurized propellant container 94, a release valve assembly knot shown), and a connection channel 92. The pressurized propellant container 94 contains the liquid propellant and has the release valve assembly. A connection channel 92 is in 20 communication with the release valve assembly and a diffuser 84. The diffuser 84 is in communication with the drug chamber 82. In one aspect, the drug chamber 82 contains an intranasal dosage. A nozzle 78 is in communication with the drug chamber 82.

In one aspect, a guide function is provided. The guide function includes a guide post 86. The guide post 86 is adjacent to a guide post arm 88. The guide post arm 88 is integral to a rotation arm 90. The rotation arm 90 may be affixed or rotatably connected to the housing body 80 so as to accommodate right or left-handed users. The guide post 86 guides aiming of the nozzle 78 within the user's nasal cavity by entering the opposing naris of the user and by limiting the angle of administration. In one aspect, the guide post arm 88 and rotation arm 90 is constructed of plastic. In yet another aspect, the guide post arm and rotation arm is constructed of structural foam.

Figure 7:
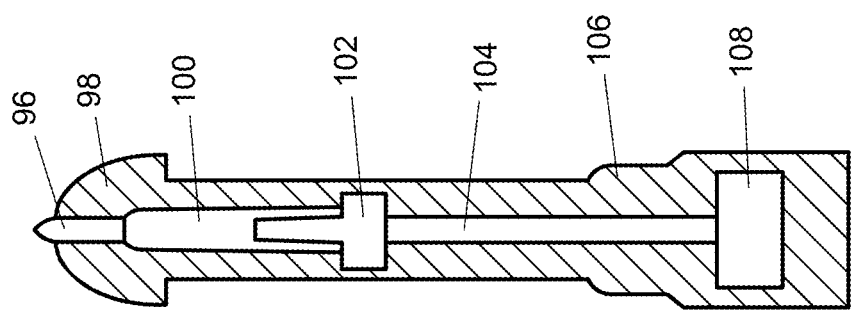
FIG. 7 shows another illustration.

Shown in FIG. 7 is another embodiment of the device. A housing body 98 is provided to assist in placement and to house the various component structures shown. A pressurized propellant container 108 contains propellant and has a release valve assembly 107. A connection channel 104 is disposed between the release valve assembly 107 and a diffuser 102. The diffuser 102 is disposed within a drug chamber 100, whereby the drug-containing intranasal dosage form is disposed within the chamber 100. A nozzle 96 is disposed on the chamber 100.

Figure 8:
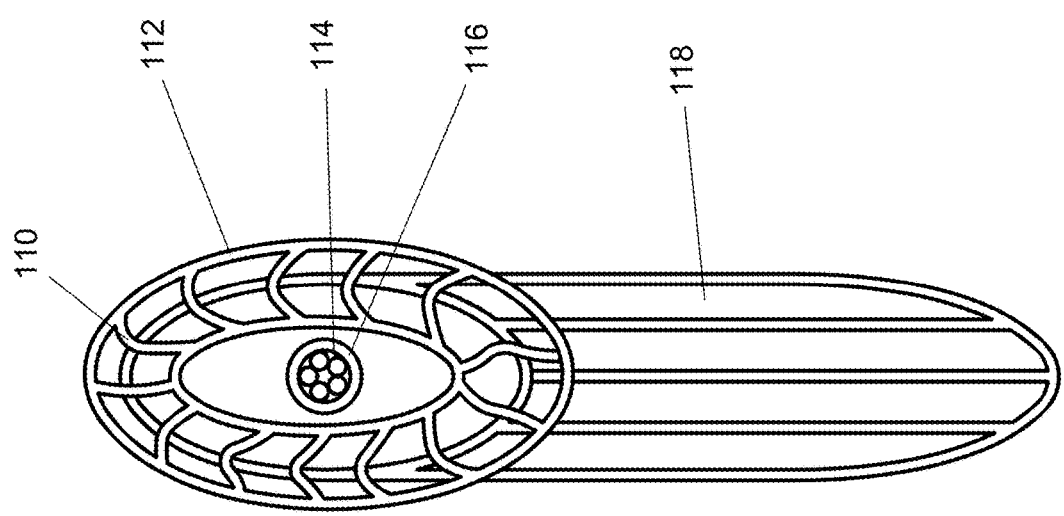
FIG. 8 shows another illustration with a nasal guide attached.

Shown in FIG. 8 is a nasal guide 112 which could be added to the drug chamber 118. The guide would not obstruct the nozzle 116 or the nozzle orifices 114 and would serve to limit the placement/insertion of the device within the nasal cavity to the desired angle of administration.

Figure 9:
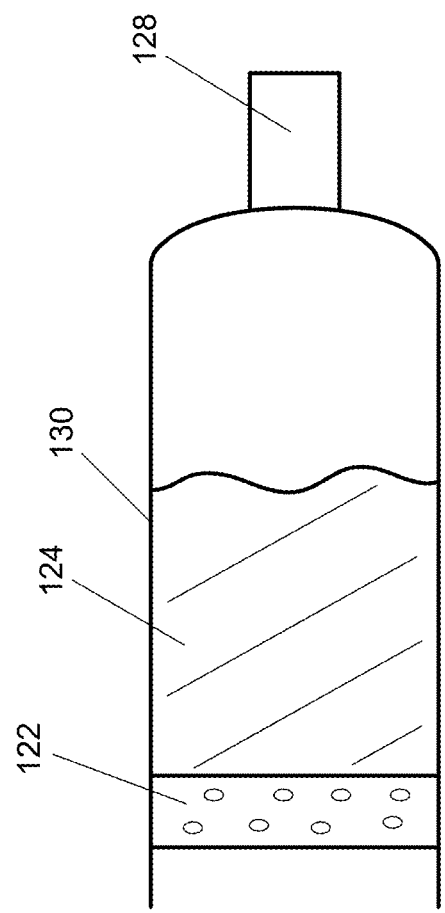
FIG. 9 shows an illustration of a diffuser and compound chamber, whereby the diffuser is cylindrical and homogeneously porous.

FIG. 9 shows one embodiment of a diffuser 122 and its relationship with the drug chamber 130. Propellant comes into to contact with the diffuser 122. The diffuser 122 converts the liquid propellant to gaseous propellant. In one aspect, it converts a majority of the liquid propellant into a gaseous propellant. In another aspect, it converts a minority of the liquid propellant into a gaseous propellant. In yet another aspect, it converts all of the liquid propellant into a gaseous propellant. In one aspect, the diffuser 122 is cylindrical in shape. In yet another aspect, the diffuser 122 is congruous in shape with the compound chamber 130.

The diffuser 122 is porous. The pores may be homogenous in size and shape. In another aspect, the pores of the diffuser 122 are heterogeneous in size and shape. In yet a further aspect, the diffuser 122 is homogenously porous. In yet a further aspect, the diffuser 122 is heterogeneously porous. As shown in FIG. 9, the diffuser 122 is cylindrical in shape and is homogenously porous, whereby the gas may pass through the pores, but the pores are impervious to the drug product 124. The gaseous propellant then contacts a drug product 124 propelling the drug product 124 through a nozzle 128 and out of the device.

Figure 10:
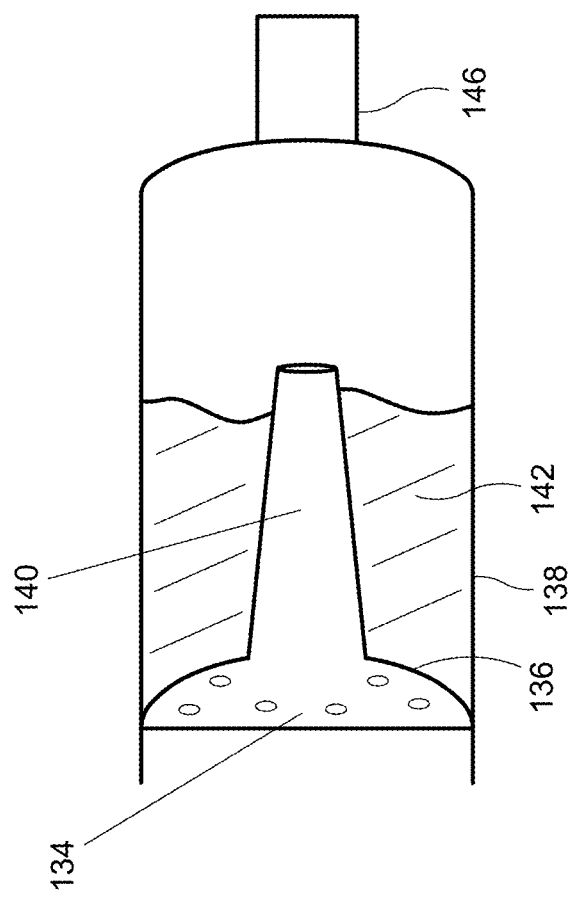
FIG. 10 shows an illustration of a diffuser and compound chamber, whereby the diffuser is cylindrical and homogeneously porous with a non-porous open tipped cone extending into the drug product.
Figure 11:
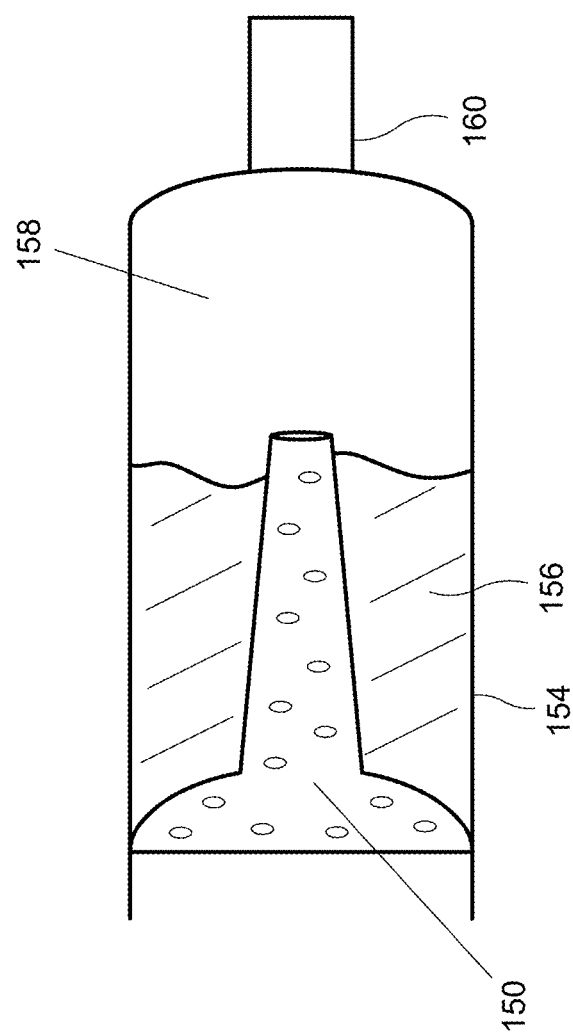
FIG. 11 shows an illustration of a diffuser and compound chamber, whereby the diffuser is cylindrical with an open tipped cone extending into the drug product and is homogeneously porous.
Figure 12:
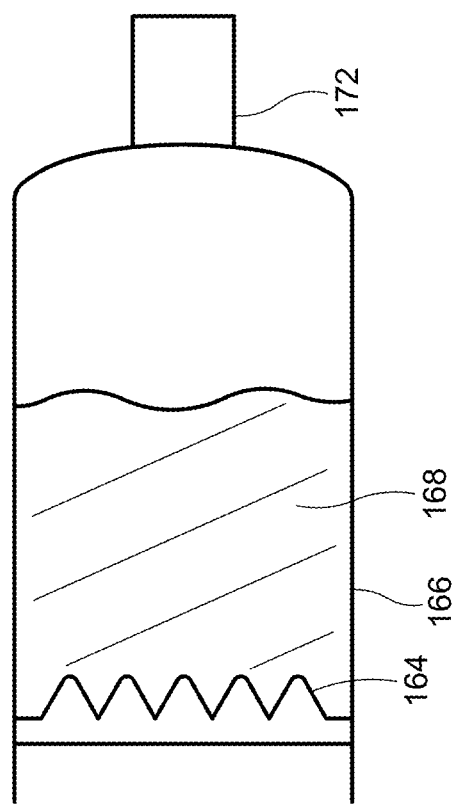
FIG. 12 shows an illustration of a diffuser and compound chamber, whereby the diffuser is cylindrical with many open tipped cones extending from it which allow gaseous propellant to enter the compound chamber.
Figure 13:
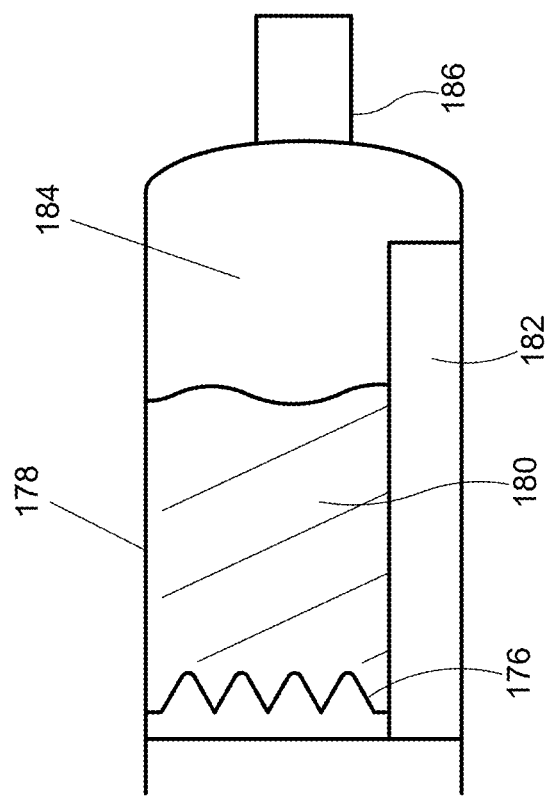
FIG. 13 shows an illustration of a diffuser and compound chamber, whereby the diffuser is cylindrical with many cones extending from it which allow gaseous propellant to enter the drug chamber. It also includes a tube which allows propellant to enter the compound chamber ahead of the drug to assist in aerosolization.
Figure 14:
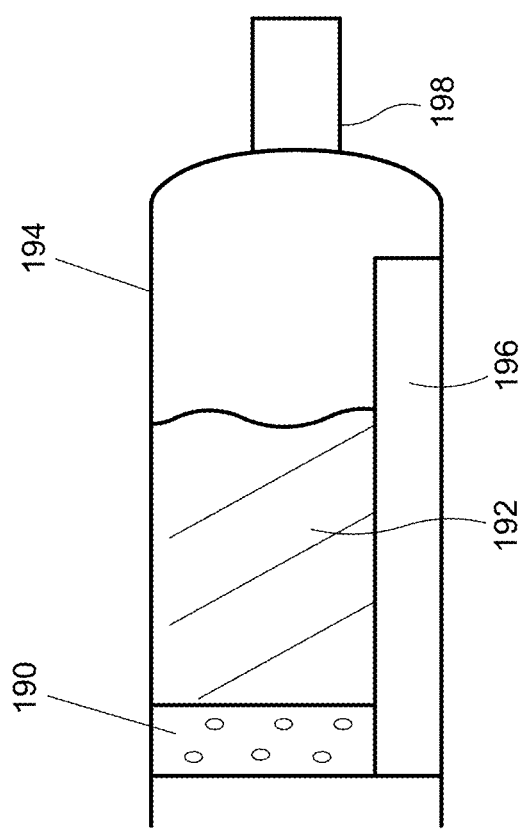
FIG. 14 shows an embodiment of a diffuser and compound chamber, whereby the diffuser is cylindrical and homogeneously porous. It also includes a tube which allows propellant to enter the compound chamber ahead of the drug to assist in aerosolization.

FIG. 10 shows is another embodiment of the diffuser 134 and its relationship with the drug chamber 138. A propellant comes into contact with the diffuser 134, propelling the drug product 142 through a nozzle 146. A portion of the gaseous propellant exiting the diffuser 134 is propelled through a diffuser extension 140, which aids in aerosolization of the drug product 142. As shown in FIG. 10, the diffuser 134 is heterogeneously porous via the diffuser extension 140.

FIG. 11 shows another embodiment of the diffuser 150 and its relationship with the drug chamber 154. Propellant comes into contact with the diffuser 150. The diffuser 150 is an extended shape or elongated shape. In one aspect, the diffuser 150 is an extended cylindrical shape. The function of the extended cylindrical shape is to increase the area of diffuser 150 in the drug chamber 154 and contact with any drug product 156 contained therein. A portion of the gaseous propellant contacts drug product 156 propelling the drug product 156 into a nozzle 160. Another portion of the gaseous propellant passes through the extended or elongated shape, aiding in aerosolization of the drug product 156. As shown in FIG. 11, the diffuser 150 is cylindrical in shape and is homogenously porous, whereby the gas may pass through the pores, but the pores are impervious to the drug product 156.

FIG. 12 shows another embodiment of the diffuser 164 and its relationship with the drug chamber 166. The propellant contacts the diffuser 164. The diffuser 164 has a plurality of conical points each with a distal hole at the tip, whereby the tips permit flow primarily of the gaseous propellant in the drug product 168. The propellant contacts the drug product 168 propelling it through the nozzle 172.

FIG. 13 shows another embodiment of the diffuser and its relationship with the drug chamber 178. The propellant contacts the diffuser member 176. The diffuser member 176 has a plurality of conical points each with a distal hole at the tip, whereby the tips permit flow of the primarily gaseous propellant in the drug product 180. A diffusion tube 182 allows propellant mixture to bypass the drug product 180 into the void space 184. The gaseous propellant exiting the diffuser member 176 contacts the drug product 180 propelling it into the void space 184 and through a nozzle 186.

The diffusion tube 182 allows for respiration to occur concurrent with use of the device. As a user uses the device, the diffusion tube 182 allows for inhalation by the user to bypass inhalation of the drug product 180 contained in the drug chamber 178. Further, the diffusion tube 182 allows for propellant to aerosolize the drug product 180 as it comes into contact with the drug product 180 in the drug chamber 178. The drug product 180 exits the device aerosolized. In another aspect absent the diffusion tube 182, the drug product 180 exits the nozzle as a liquid or partial aerosol or a combination. In one aspect, a frit or a plurality of frits (not shown) is in communication with the diffusion tube 182 and/or diffusion member 176 so as to act as a check valve.

FIG. 14 shows another embodiment of the diffuser 190 and its relationship with the drug chamber 194. The propellant contacts the diffuser 190 that is homogenously porous whereby the gas may pass through the pores, but the pores are impervious to the drug product. A diffusion tube 196 allows propellant mixture to bypass the drug product 192 into the void space 197. The gaseous propellant exiting the diffuser 190 contacts the drug product drug 192 propelling it into the void space 197 and through a nozzle 198.

The diffusion tube 196 allows for respiration to occur concurrent with use of the device. As a user uses the device, the diffusion tube 196 allows for inhalation by the user to bypass inhalation of the drug product 192 contained in the drug chamber 194. Further, the diffusion tube 196 allows for propellant to aerosolize the drug product 192 as it comes into contact with the drug product 192 in the drug chamber 194. The drug product 192 exits the device aerosolized. In another aspect absent the diffusion tube 196, the drug product 192 exits the nozzle 198 as a liquid or partial aerosol or a combination. In one aspect, a frit or a plurality of frits (not shown) is in communication with the diffusion tube 196 so as to act as a check valve.

Figure 15:
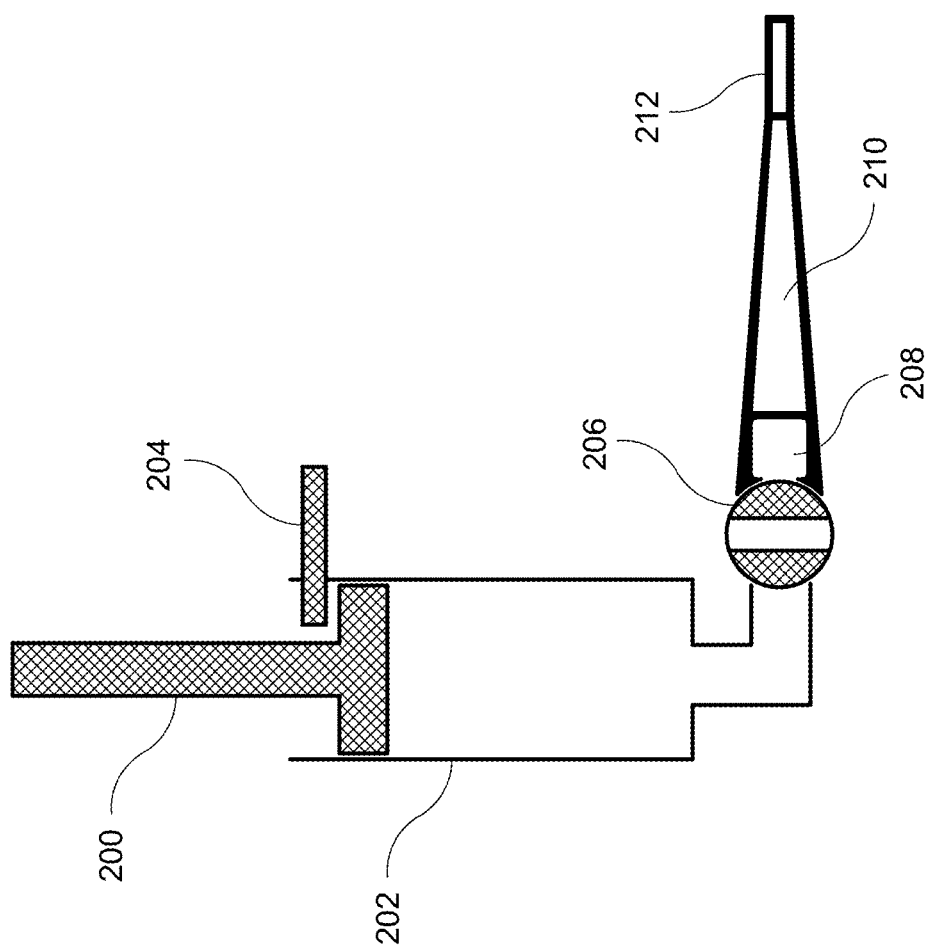

FIG. 15 shows another embodiment of the device. The manual pressure actuator allows the user to administer the device without the need of a prefilled pressurized canister or HFA canister. This device has a piston 200 which is depressed into the air compression chamber 202 resulting in a quantity of compressed air held within the air compression chamber 202. The trapped air is thus raised from ambient pressure to several times that of ambient air pressure. In one aspect, the manual pressure actuator is a syringe or syrette. The device contains a lock pin 204 that is inserted to hold the piston in the high pressure position. In addition the device contains a trigger valve 206. In an aspect, the trigger valve 206 is similar to a stopcock valve. There is a diffuser 208 in communication with the trigger valve 206 and the compound holding chamber 210. The compound is placed in the compound holding chamber 210 which is in communication with a nozzle 212. While the device is put in the high pressure state, the trigger valve 206 is placed in the load position, which blocks the high pressure air in the air compression chamber 202. When the trigger valve 206 is moved into the open position by the user, the compressed air in the air compression chamber 202 travels through the diffuser and into the compound holding chamber where it mixes with the compound. A mixture of compressed air and compound then exits the device through the nozzle 212 with a positive velocity.

Figure 16:
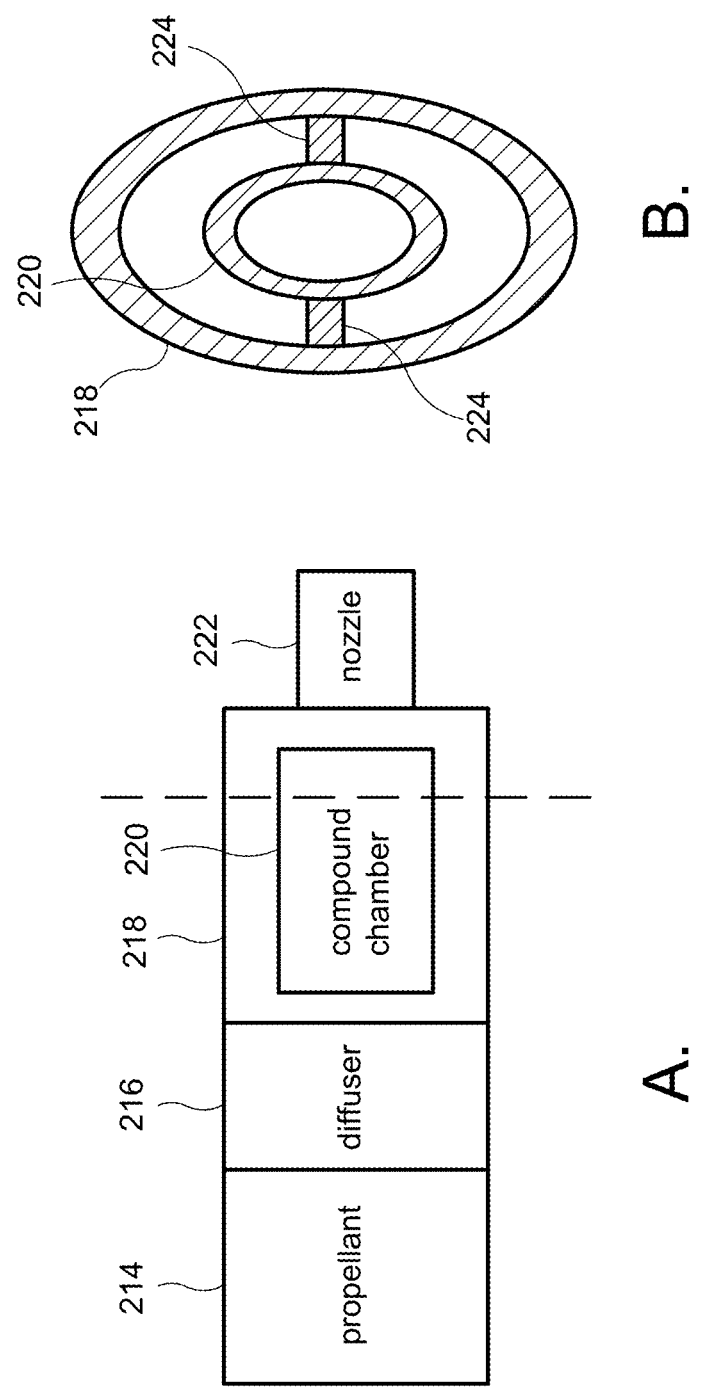

FIG. 16A shows another embodiment of the device which is suitable to deliver a compound into the nasal cavity of an animal or human. A pressurized propellant container 214 is in communication with a diffuser 216. The diffuser 216 is in communication with the interior of the housing body 218 and with the compound chamber 220. The interior of the housing body 218 is in communication with a nozzle 222. FIG. 16B is a cross section of FIG. 16A at the dashed line. FIG. 16B shows that the compound chamber 220 is connected to the housing body 218 by flanges 224. The propellant is diffused by the diffuser 216 and the flanges 224 allow the diffused propellant to travel both through the compound chamber 220 and also around the compound chamber 220. When the pressurized propellant container 214 is actuated to release an amount of propellant, the propellant travels through the diffuser 216. The diffuser disperses the propellant into the interior of the housing body 218 and into the compound chamber 220 where the propellant mixes with the compound. The propellant also travels on the outside of the compound chamber 220 and then mixes with the compound exiting the compound chamber 220. The mixture of pharmaceutical compound and propellant then exits the nozzle 222. As a user uses the device, the relationship of the compound chamber 220 with the housing 218 allows for inhalation by the user to bypass inhalation of the drug product contained in the compound chamber 220.

The device may be for pediatric or adult use. One of skill in the art can envision modifications of the device to accommodate for pediatric or adult use.

In another embodiment, the device delivers a compound through the mucosa or epithelium of the tongue, mouth, skin, or conjunctiva. In another embodiment, the method includes administering a composition of the compound on or to the tongue, on or to the skin, or on or to the conjunctiva of the subject.

In yet another embodiment, the device delivers the compound to the turbinate regions of the nasal cavity. In one aspect, the device delivers the compound primarily to the turbinate regions of the nasal cavity.

In additional embodiments, the device may be used for treatment, prevention, or palliative care. The device may be used in research or industrial purposes. The device can be used to disperse a compound which has been propelled by a propellant having been in communication with a diffuser. For example, the device may be used in agriculture to dispense an agricultural compound.

An intranasal formulation of an oxime is provided. Additionally, a method of intranasal administration of an oxime to the olfactory region is described.

Oximes can be delivered to the central nervous system (CNS) for the prevention, treatment, and palliative care of exposure to organophosphate (OP) compounds such as chemical warfare nerve agents (e.g. sarin, tabun, soman, Russian VX, etc.) or pesticides (e.g. diisopropylfluorophosphate). Oximes had traditionally been delivered, for example, intravenously. Intranasal administration of an oxime to the olfactory region allows for transport across the BBB.

Nerve agents containing organophosphorous compounds are a significant threat to the warfighter, who may be exposed in battlefield settings on land, sea, air and space. Civilian populations also face health risks associated with nerve agents during the use of commercially available pesticides, as do first responders to a terrorist attack. The current treatment regimen for nerve agent exposure includes the use of a cholinergic reactivator (pralidoxime, 2-PAM), muscarinic receptor antagonist (atropine) and an anticonvulsant (diazepam). While 2-PAM and atropine are available in multiple injection formats, (e.g. IV infusion or IM autoinjector), injection presents significant and practical challenges in the battlefields, such as the need to remove body armor, and have correct training in the use of autoinjectors. Moreover, newer oximes such as MMB4 and HI6 are difficult to formulate in current autoinjector formats. There is great need to develop practical, more effective and rapid onset systems capable of distributing anti nerve gas agents, such as oximes, capable of penetrating into the central nervous system (CNS) of subjects in battlefield and emergency situations.

The method for delivering an oxime across the blood brain barrier to a subject in need thereof includes administering to the subject a therapeutically effective dosage of an oxime, where the dosage is delivered to the upper olfactory region of the nasal cavity.

In one aspect of the method, the therapeutically effective amount of an oxime administered to the user is within the range of about 0.001 mg/kg to about 100 mg/kg.

In another aspect of the method, the therapeutically effective amount of an oxime administered to the user is within the range of about 0.01 mg/kg to about 10 mg/kg.

In yet another aspect of the method, the therapeutically effective amount of an oxime administered to the user is within the range of about 0.1 mg/kg to about 1 mg/kg. In one aspect, the mg/kg is mg of compound per kilogram of body weight. In another aspect, the dosage is a flat dosage independent of weight.

In performance of the method of delivery of an oxime intranasally to the olfactory region includes providing the device described herein for insertion into the user's nasal cavity. The device is inserted into the user's nasal cavity. At least one therapeutically effective dose of an oxime is delivered via the device. At least one therapeutically effective dose of the oxime is delivered to the olfactory region. Delivery of the oxime to the olfactory region allows for delivery of the oxime across the BBB.

Oximes such as but not limited to 2-PAM (2-pyridine aldoxime methyl chloride), MMB4, HI6, TMB4, Hlo7 are currently used to treat OP exposure but they poorly penetrate the blood-brain-barrier. Thus, the oximes, in their current form of administration, do little to treat or prevent the CNS damage caused by these compounds.

By using the using the device described herein for the method, the compound, such as the oxime, can be self-administered, or administered by a battle-buddy or civilian, with or a user without prior medical training. The device delivers compound without requiring a specific breathing pattern by the user and can be administered to an unconscious user.

Direct transport percentage (DTP %) to the brain was calculated using an oxime to determine the amount of drug in the brain that was distributed directly from the nasal cavity to the CNS. In one embodiment, the DTP was 62.6+/−9.6%. In one aspect, the DTP was greater than 64.2%. In another aspect, the DTP was at least 64.3%. In another aspect, the DTP was at least 53%. In another aspect, the DTP was greater than 53%. In another aspect, the DTP was greater than 55%. In another aspect the DTP was at least about 55%, 60%, 65%, 70%, 75%, 80%, 85%, 90%, 95%, 99%, or 100%, inclusive of endpoints. In another aspect, the DTP was at least about 40%, 45%, 505, 55%, 60%, 65%, 70%, 75%, 80%, 85%, 90%, 95%, 99% or 100%, inclusive of endpoints.

The device deposits a compound on the olfactory region. In one embodiment, the percent deposition of the compound is at least 64.2%. In one aspect, the percent deposition of the compound was greater than 64.2%. In another aspect, the percent deposition of the compound was at least 64.3%. In another aspect, the percent deposition of the compound was greater than 50%. In another aspect, the percent deposition of the compound was greater than 55%. In another aspect the percent deposition of the compound was at least about 55%, 60%, 65%, 70%, 75%, 80%, 85%, 90%, 95%, 99%, or 100%, inclusive of endpoints. In another aspect, the percent deposition of the compound was at least about 40%, 45%, 505, 55%, 60%, 65%, 70%, 75%, 80%, 85%, 90%, 95%, 99% or 100%, inclusive of endpoints.

Compounds which can be delivered by the device described include but are not limited to those for the palliative, prevention or treatment of infectious diseases, inflammatory diseases, and oncology. Compounds which can be delivered by the device include but are not limited to those for the palliative, prevention or treatment of Parkinson's disease, Alzheimer's disease, depression, stroke, epilepsy, autism, lysosomal storage disorders, fragile X syndrome, ataxis, insulin deficiency, and blindness. Compounds which can be delivered include but are not limited to deferoxamine (DFO), glucagon-like peptide-1 antagonist, cephalexin, midazolam, morphine, insulin-like growth factor-1, nerve growth factor, insulin, oximes, imaging agents including but not limited to FDL and FLT, GDP-5, and cytokines including but not limited to interleukins (i.e., IL-1, IL-2, IL-3, IL-4, IL-5, IL-6, IL-7, IL-8, IL-9 and IL-10), interferons, and tumor necrosis factor (i.e., TNF-α and TNF-β).

To overcome the deficient brain penetration associated with many orally or intravenously administered drugs, the intranasal route is a means to achieve direct drug access to the CNS. The upper region of the nasal cavity provides immediate access to the olfactory epithelium, which, by virtue of being a leaky barrier between the nose and the brain, presents a unique opportunity to deliver drugs into the brain. Drug deposited in this olfactory region results in rapid access to the brain with minimal absorption into the blood. Preclinical studies indicate a rapid transport from the nasal cavity to many regions of the brain and spinal cord at greatly enhanced concentrations compared to systemic drug delivery methods.

Intranasal administration of compounds offers several advantages over traditional surgical, intravenous or oral routes for administration across the blood brain barrier (BBB). Intranasal administration to the olfactory region avoids gastrointestinal destruction and hepatic first pass metabolism, such as destruction of drugs by liver enzymes. Intranasal administration provides ease, convenience and safety. Intranasal drug administration is generally painless and does not require sterile technique, intravenous catheters or other invasive devices, and is generally immediately and readily available for all patients.

In one embodiment of the POD device 310, the POD device 310 has a rear puncture member 315 and a front puncture member 320 and is capable of accepting a unit dose container 330. In another aspect, the front puncture member 320 may be integral with the nozzle 360. In yet another aspect as show in FIG. 36, the POD device 310 does not have a front puncture member 320. In this aspect, the POD device 310 has a nozzle 360 integral with the unit dose container 330 as shown in FIG. 36. In another aspect, the angles of the front puncture member 320 and/or the rear puncture member 315 may vary. In yet another aspect, the unit dose container 330 may be sealed by, for example but not limited to a rubber or foil seal. In an aspect, the POD device 310 may be a translational device or a rotational device. In yet another aspect, the puncture members may have one or more orifices. In yet another aspect, the POD device 310 may have a combination of one or more of the various aspects described herein.

The unit dose container 330 described herein may be manufactured using a variety of manufacturing processes including but not limited to injection molding, blow molding, or a blow-fill-seal process. Blow fill seal technology involves forming, filling, and sealing a dosage form in a continuous process in a sterile enclosed area inside a machine. Depending on the product to be contained and the manufacturing process used, the unit dose container 330 may be made of a polymer, such as polyethylene, ethyl vinyl alcohol copolymer, low-density polyethylene (LDPE), high-density polyethylene (HDPE), polypropylene (PP) or any other suitable polymer, mixture or the like that is suitable for forming the unit dose container 330.

Furthermore, while unit dose container 330 is illustrated as being substantially cylinder-shaped, the unit dose container 330 may comprise any other shape suitable for selectively dispensing a unit-dose of a compound or product. For example, the unit dose container 330 may be substantially cone-shaped, tube-shaped, rectangular-shape, polygonal, oval-shaped, or combinations of any of these. Moreover, while the end of the unit dose container 330 is shown as being substantially flat, the end may alternatively be crimped (e.g., in the case where the dispenser is formed by a blow-fill-seal process).

Figure 25:
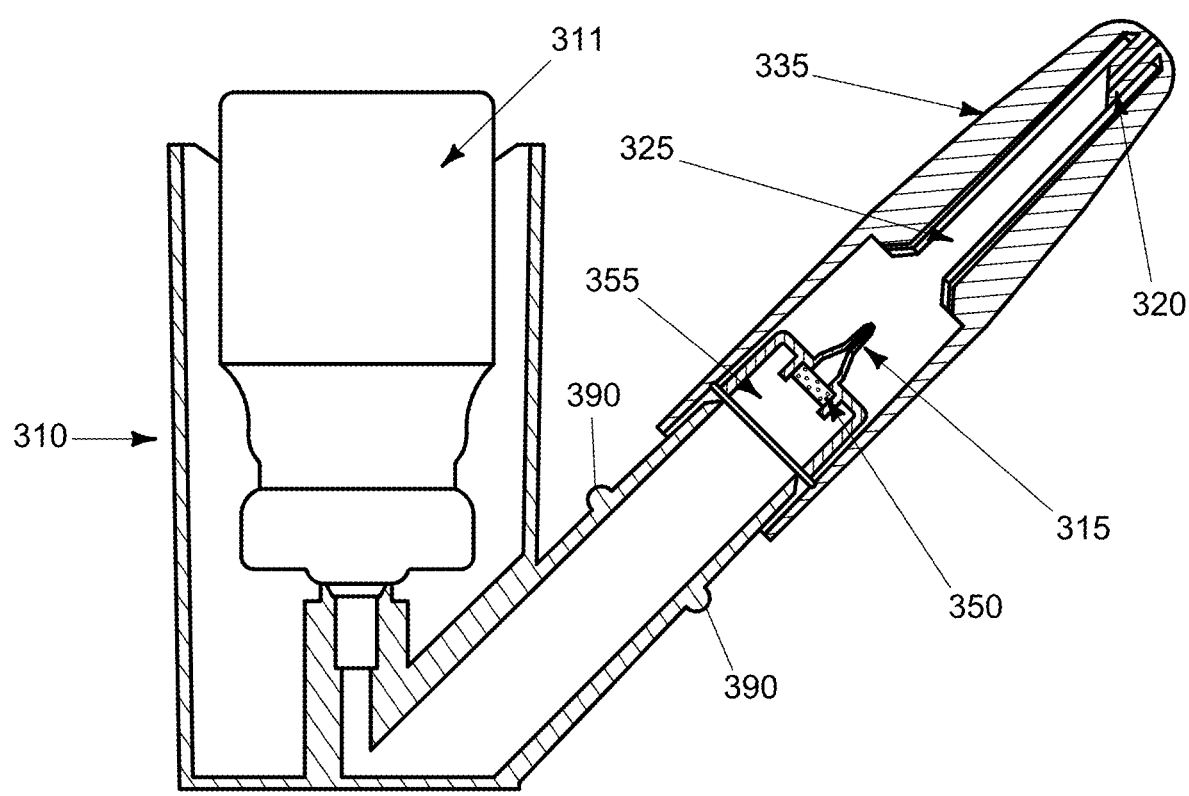

FIG. 25 illustrates one aspect of the POD device 310 having a rear puncture member 315 and a front puncture member 320 and having a container holding area capable of accepting a unit dose container 330. In one aspect, the container holding area is a hollow or a container cavity 325. These components are housed in the POD device tip 335. The POD device tip 335 is an umbrella term for the assembly of the tip body, rear puncture member 315, diffuser 350, unit dose container 330, front puncture member 320 and nozzle 360.

Figure 26:
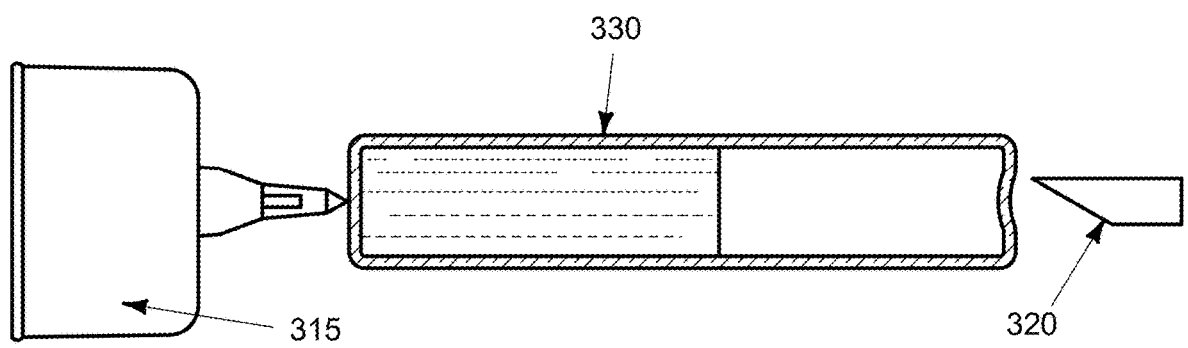

FIG. 26 illustrates a unit dose container 330. The rear puncture member 315 is located at the distal end of the POD device 310 as the POD device 310 is located when in use and inserted into a user nasal cavity; e.g. farther from the nasal cavity of the user. The front puncture member 320 is located at the proximal end of the POD device 310 as the POD device 310 is located when in use and inserted into a user nasal cavity; e.g. nearer to the nasal cavity of the user.

As illustrated in FIG. 26, in one aspect, the unit dose container 330 is cylindrically shaped with closed ends. Moreover, while the end of the unit dose container 330 is shown as being closed and substantially flat, the end may alternatively be crimped or dimpled.

Figure 30:
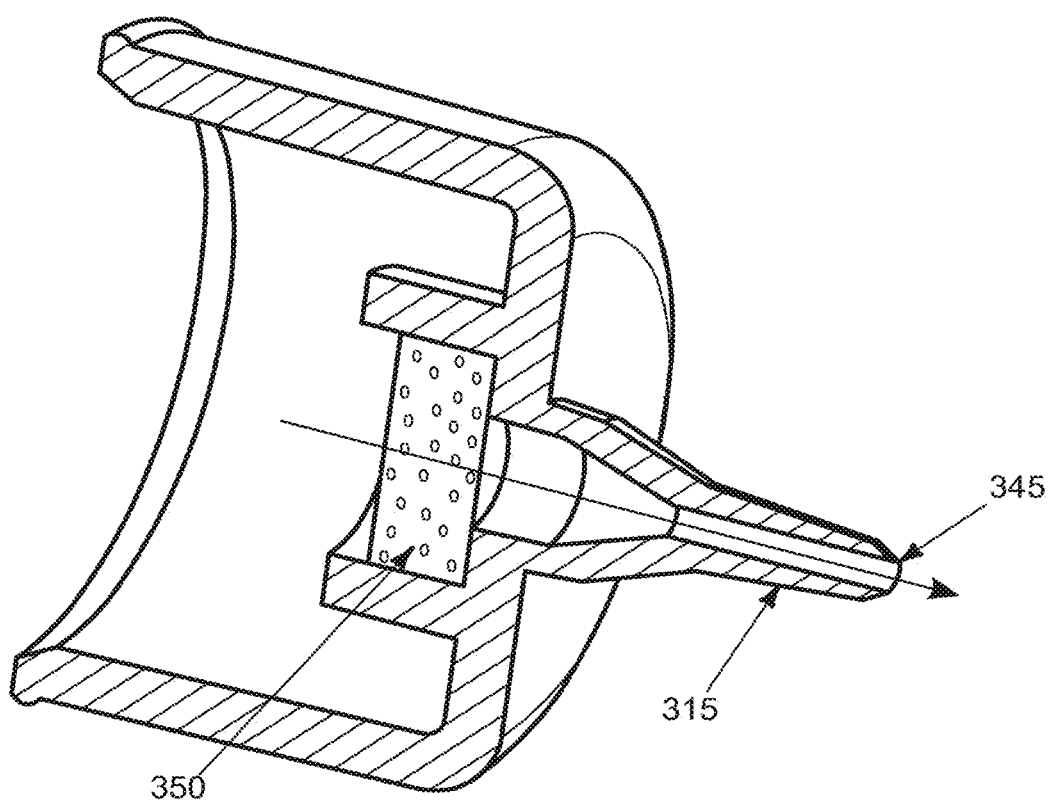
Figure 31A:
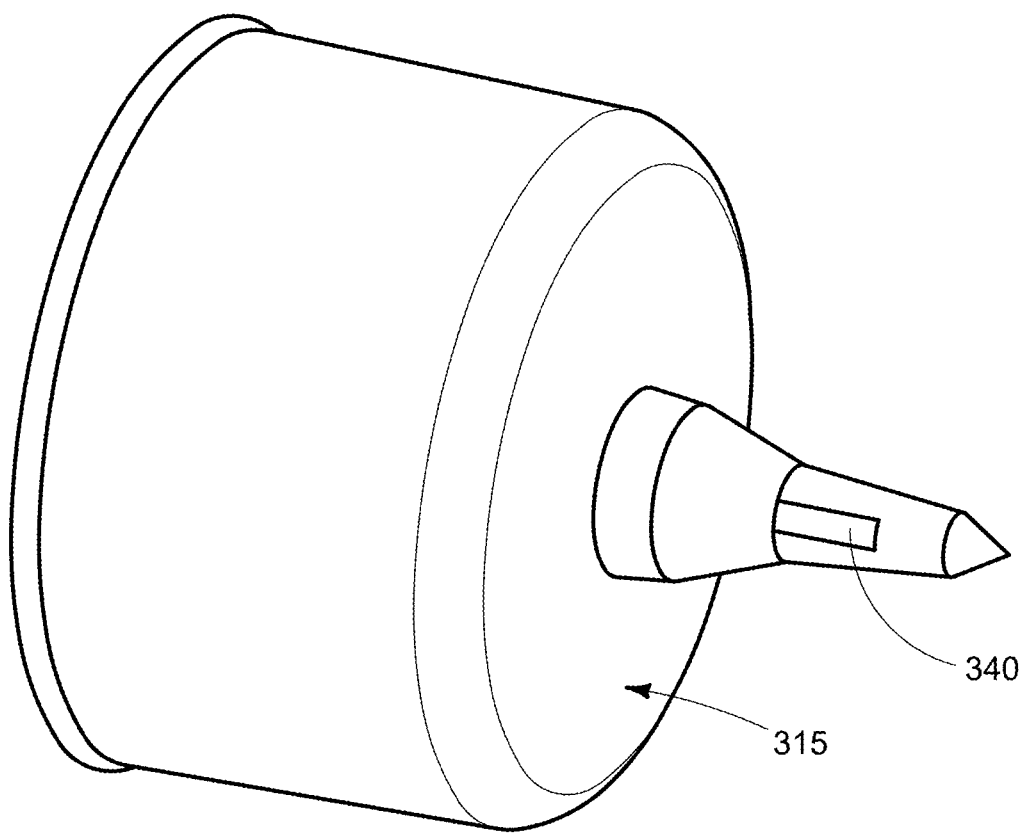
Figure 31B:
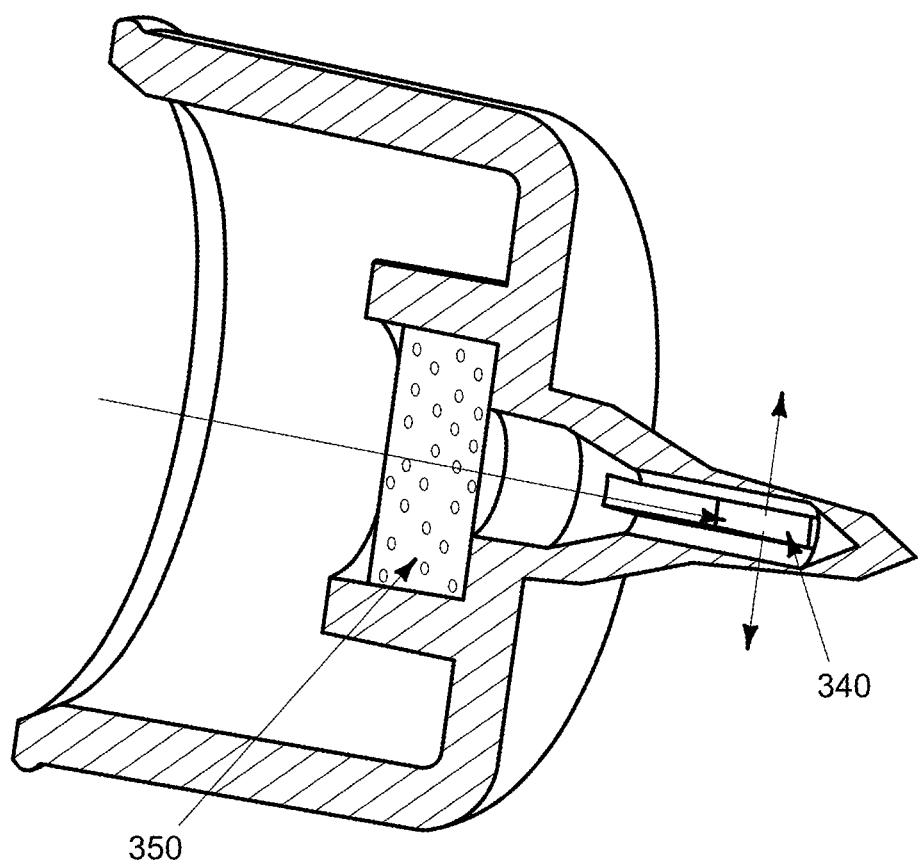

FIG. 26 shows the rear puncture member 315 and the front puncture member 320 not operationally engaged with the unit dose container 330. The rear puncture member 315 and the front puncture member 320 both allow for transport or conveyance of the propellant and/or propellant compound mixture. In further illustrations of this aspect, as illustrated in FIGS. 30 and 31b, the rear puncture member 315 has a hollow portion for delivery of the propellant or, as illustrated in FIG. 32, is constructed of a porous material. Whereas, in the aspect with a front puncture member 320, the front puncture member 320 has a hollow portion for delivery of at least the compound contained in the unit dose container 330.

Figure 27:
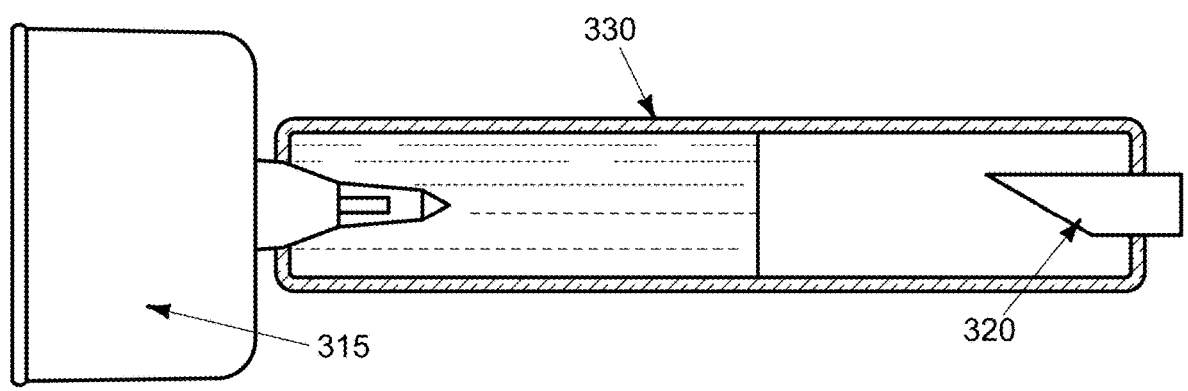

FIG. 27 shows the rear puncture member 315 and the front puncture member 320 operatively engaged with the unit dose container 330, with the rear puncture member 315 and the front puncture member 320 inserted into the unit dose container 30.

Figure 28:
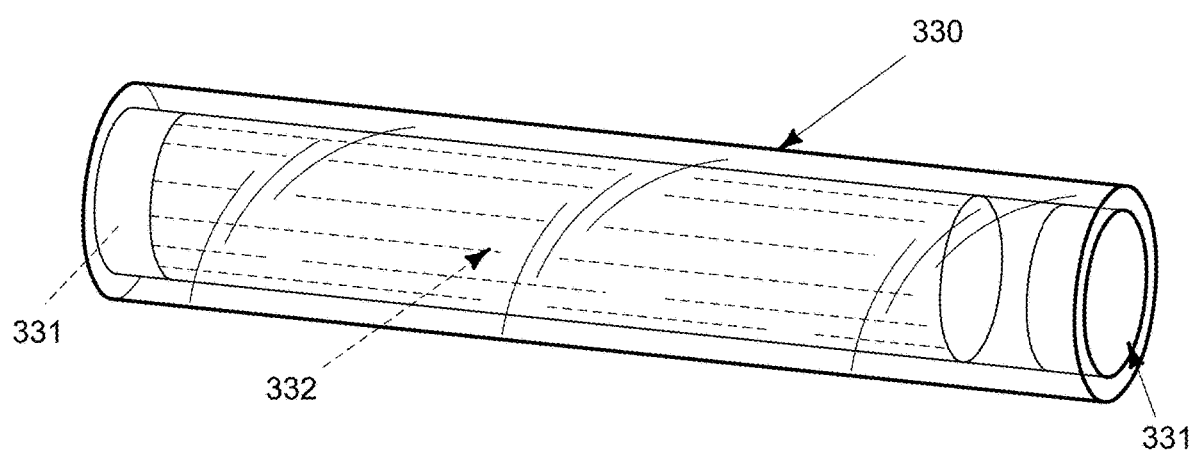

FIG. 28 illustrates the unit dose container 330. The unit dose container 330 may be manufactured from glass or a polymer, such as polyethylene, ethyl vinyl alcohol copolymer, low-density polyethylene (LDPE), high-density polyethylene (HDPE), polypropylene (PP) or any other suitable polymer, mixture or the like that is suitable for forming the unit dose container 330. In one illustration of this aspect, the unit dose container 330 is manufactured from polyethylene. In another illustration of this aspect, the unit dose container 330 is manufactured from ethyl vinyl alcohol copolymer. In yet another illustration of this aspect, the unit dose container 330 is manufactured from low-density polyethylene (LDPE). In yet another illustration of this aspect, the unit dose container 330 is manufactured from high-density polyethylene (HDPE). In another illustration of this aspect, the unit dose container 330 is manufactured from polypropylene (PP). In yet another illustration of this aspect, the unit dose container 330 is manufactured from any other suitable polymer, mixture or the like that is suitable for forming the unit dose container 330.

The unit dose container 330 described herein may be manufactured using a variety of manufacturing processes, such as injection molding, blow molding, or a blow-fill-seal process.

FIG. 28 illustrates one aspect of the unit dose container 330 where the unit dose container 330 is sealed with polymeric stoppers 331, such as but not limited to rubber. In further examples of this aspect, the unit dose container 330 may be foil sealed. The stoppers can be a combination of the above options.

As shown in FIG. 28, the unit dose container 330 has aspects of the POD device 310 compound chamber. The unit dose container 330 is capable of holding a compound 332. The unit dose container 330 is designed to be prefilled to a specific volume. The unit dose container 330 can release the entirety of the dose (single dosing).

As shown in FIGS. 29-32, the puncture materials can be rigid, semi-rigid, or porous. The puncture designs can be either through hole, side orifice, porous flow, or a combination.

Figure 29:
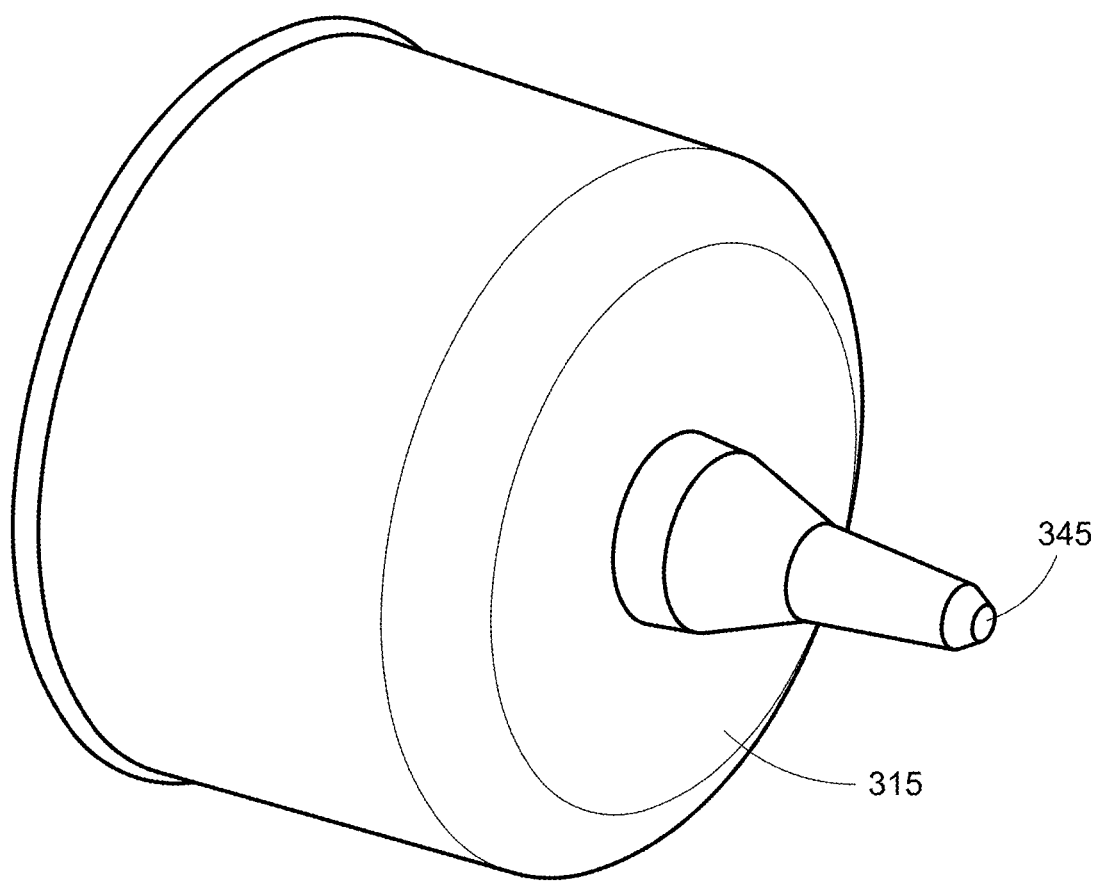

FIG. 29 illustrates a rear puncture member 315. In an example of this aspect, the rear puncture member 315 may or may not have a side orifice 340 or a plurality thereof. As shown in FIGS. 30 and 31b, the side orifice 340 assists in reducing residuals of the compound which may remain in the unit dose container 330 after actuation. The side orifice(s) 340 allow for the propellant released from the canister 311 to scour the sides of the unit dose container 330. In one example of the side orifice 340, the side orifice 340 may be substantially oval, circular, square, triangular, or rectangular in shape or combinations thereof.

As illustrated in FIG. 30, the rear puncture member 315 provides a distal opening 345. The distal opening 345 allows for a path through which the propellant journeys or is conveyed from the canister 311 as it is introduced into the unit dose container 330. As illustrated by the arrow showing the direction of travel of the propellant in FIG. 30, the propellant travels across the diffuser 350 of the POD device 310. As illustrated by the arrows showing the direction of travel of the propellant in FIG. 31b, the propellant travels across the diffuser 350 of the POD device 310 and out the side orifice(s) 340.

FIG. 32 illustrates one aspect of the rear puncture member 315 in which the rear puncture member 315 is of porous material. The arrows in FIG. 32 illustrate the direction of flow of the propellant from the canister 311 across the porous rear puncture member 315. In further illustrations of this aspect, the porous rear puncture member 315 is seated inside a solid non-porous puncture member housing 355.

FIGS. 33 and 34 show the front puncture member 320. FIGS. 33 and 34 show the front puncture member 320 engaged within the unit dose container 330. FIG. 33 shows the front puncture member 320 with an integrally molded nozzle 360. Whereas, FIG. 34 shows the front puncture member 320 with a separately molded nozzle 360. The front puncture member 320 sits within a puncture member housing 355. The front puncture member 320 provides a proximal opening 365.

In operation of the POD device 310 with a non porous rear puncture member 315 and no side orifice(s) 340, the propellant from the canister 311 is conveyed or travels from the canister 311, across the diffuser 350, follows the path of the arrow shown in FIG. 30, exits the distal opening 345 of the rear puncture member 315, enters the unit dose container 330, the compound and/or propellant travels along the path of the arrow shown in FIGS. 33 and 34, and exits the proximal opening 365 of the front puncture member 320.

In operation of the POD device 310 with a porous rear puncture member 315 and no side orifice(s) 340, the propellant from the canister 311 is conveyed or travels from the canister 311, across the diffuser 350, follows the path of the arrow shown in FIG. 32, exits the distal opening 345 of the rear puncture member 315, enters the unit dose container 330, the compound and/or propellant travels along the path of the arrow shown in FIGS. 33 and 34, and exits the proximal opening 365 of the front puncture member 320.

In operation of the POD device 310 with a non porous rear puncture member 315 and a side orifice(s) 340, the propellant from the canister 311 is conveyed or travels from the canister 311, across the diffuser 350, follows the path of the arrow shown in FIG. 31b, exits the side orifice 340 of the rear puncture member 315, enters the unit dose container 330, the compound and/or propellant travels along the path of the arrow shown in FIGS. 33 and 34, and exits the proximal opening 365 of the front puncture member 320.

As shown in FIG. 35, the geometry can be changed from straight cylinder designs. In blow fill seal in particular, the geometry is very customizable. Some of the geometry changes include a dimple 395 to center the puncture.

As shown in FIG. 36, a blow fill seal has the potential to over mold the nozzle 360 and eliminate the need for a double puncture of the unit dose container 330. It would allow for a rear puncture member 315 and removal of a front tab 370. Removal of the tab 370 provides access to the nozzle 360 through with the dose travels to be released.

As shown in FIG. 37, to center and stabilize the unit dose container 330, a rib 375, or plurality of ribs, can be added along the length of the unit dose container 330 in order to well fit the unit dose container 330 in the container cavity 325. In FIG. 37, the ribs 375 are shown in engagement with the container cavity wall 380. The rib 375 would form an interference fit and prevent sliding or movement prior to piercing or puncturing of the unit dose container 330.

FIGS. 25 and 41 illustrate two aspects of POD device 310 having a rear puncture member 315 and a front puncture member 320 and having a container cavity 325 capable of accepting a unit dose container 330. The container cavity 325 and the unit dose container 330 are cooperatively sized. FIG. 25 shows one aspect of the POD device 310 where the tip 335 engages the actuator body 385 in a translational manner. FIG. 41 shows another aspect of the POD device 310 where the tip 335 engages the actuator body 385 in a threaded manner 386.

As shown in FIG. 25, on the actuator body 385 of the POD device 310 which engages the tip 335 in a translational manner is a stop 390. The tip 335 slides onto the actuator body 385 and comes to a fixed position as it journeys over the stop 390. In FIG. 41, the tip 335 is associated with the actuator body 385 via male and female threads. In this aspect, the male threads or female threads may be cooperatively arranged to be either on the tip 335 or the actuator body 385. The tip 335 is threaded onto the actuator body 385. In both illustrations shown in FIGS. 25 and 41, the POD device 310 is not in its operational use when the tip 335 is not engaged with the actuator body 385.

FIG. 25 shows an aspect of the embodiment where the container cavity 325 does not contain a unit dose container 330. FIG. 38 shows the POD device 310 in partial engagement with the unit dose container 330. FIG. 38 shows the rear puncture member 315 in engagement with the unit dose container 330. FIG. 39 shows the rear puncture member 315 and the front puncture member 320 in engagement with the unit dose container 330.

FIG. 40 shows an exploded view of the of the translational POD device shown in FIG. 25.

Figures 42A, 42B, 42C, 42D, 42E:
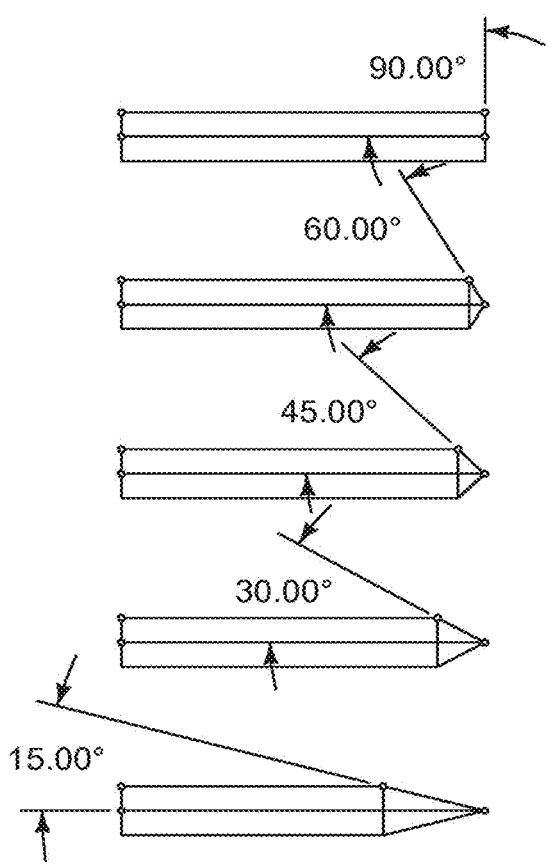

FIGS. 42a-e illustrate the various angles of puncture of the rear puncture member 315. FIG. 42a shows a 90 degree rear angle of puncture on the rear puncture member 315. FIG. 42b shows a 60 degree angle of puncture on the rear puncture member 315. FIG. 42c shows a 45 degree angle of puncture on the rear puncture member 315. FIG. 42d shows a 30 degree angle of puncture on the rear puncture member 315. FIG. 42e shows a 15 degree angle of puncture on the rear puncture member 315. In one aspect, the puncture angle is from about 15 degrees to about 90 degrees, from about 30 degrees to about 90 degrees, from about 45 degrees to about 90 degrees, from about 60 degrees to about 90 degrees, or combinations thereof.

In further illustrations of the angles of puncture shown in FIGS. 42a-e, the angles of puncture may also apply to the front puncture member 320. Although the front puncture member 320 is shown as a beveled member in the figures, the front puncture member may be shaped with angles of puncture as illustrated in FIGS. 42a-e with regards to the rear puncture member 315.

The invention is further described in the following examples, which are in not intended to limit the scope of the invention.

Example 1

An oxime drug, 2-PAM, was administered into the olfactory nasal region in rats with the device, (e.g. a Pressurized Olfactory Delivery (POD) device). The brain and plasma concentrations of 2-PAM was measured at certain time points after drug administration. The device enabled delivery of 2-PAM resulted in higher brain exposure and lower plasma exposure compared to intravenous injection.

Animal use. Rats were used for deposition, tolerability and distribution experiments. Adult male Sprague-Dawley rats (200-300 g; Harlan, Indianapolis, Ind.) were housed under a 12 hour light/dark cycle with food and water provided ad libitum. Animals were cared for in accordance with institutional guidelines, and all experiments were performed with an approved protocol from the Pacific Northwest Diabetes Institute Institutional Animal Care and Use Committee under protocol number 12610.

Statistical analysis. In most cases where two values were compared a t-test was used. When more than two groups were compared, such as comparing the powder 2-PAM POD formulation with the aqueous 2-PAM POD formulation and the IV 2-PAM, a two-way ANOVA was used with a bonferroni post test. When comparing the AUC plasma and brain values which were derived from different animals at each time point the method described in Westin et al., 2006 was used. In all cases statistical significance was defined as $p<0.05$.

Aqueous formulations of 2-PAM were made by dissolving 2-PAM in deionized water. 2-PAM was dissolved into 500 µl of water at 10 mg/ml, 100 mg/ml, 250 mg/ml, and 500 mg/ml and left in a closed microcentrifuge tube at ambient temperature (25°). These water based formulations were then visually observed at 1 hour, 24 hours, and 48 hours for any cloudiness or precipitant.

Dry powder formulation of 2-PAM was prepared by placing the 2-PAM free drug in a microcentrifuge tube and grinding the drug with a motorized pestle (Kontes, Vineland, N.J.). The 2-PAM powder was then observed under a microscope to ensure the homogeneity of the powder formulation. The 2-PAM was ground with a pestle to ensure that there were no agglomerations of 2-PAM greater than 100 µm in diameter. Such larger agglomerates could clog the 810 µm diameter POD nozzle used in the rat experiments.

Figure 17:
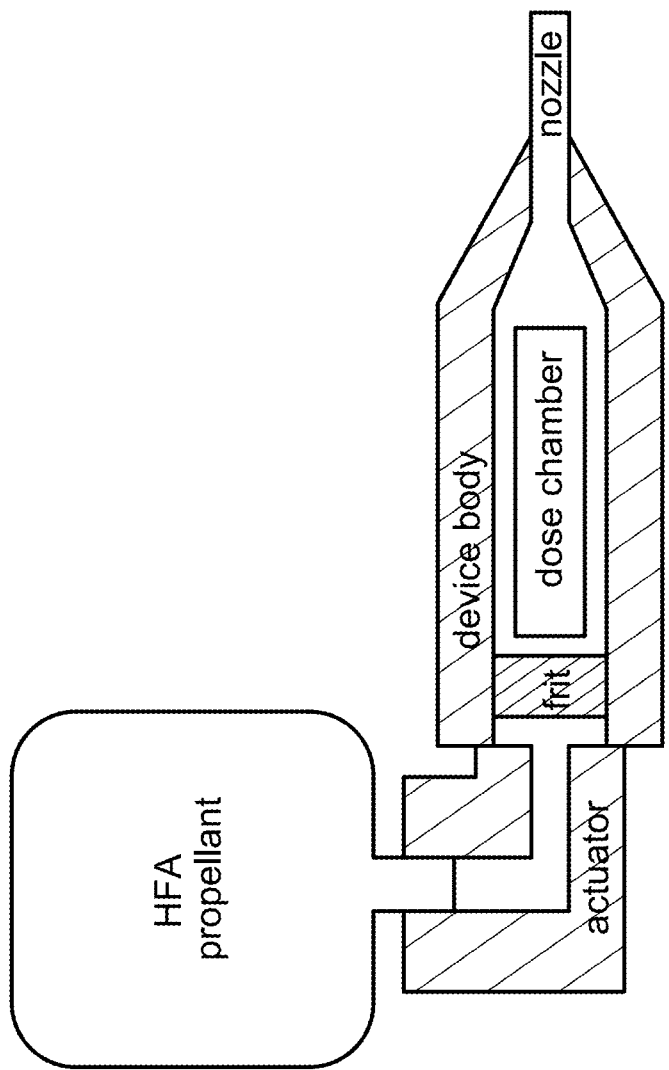
Figure 18:
Figure 18:
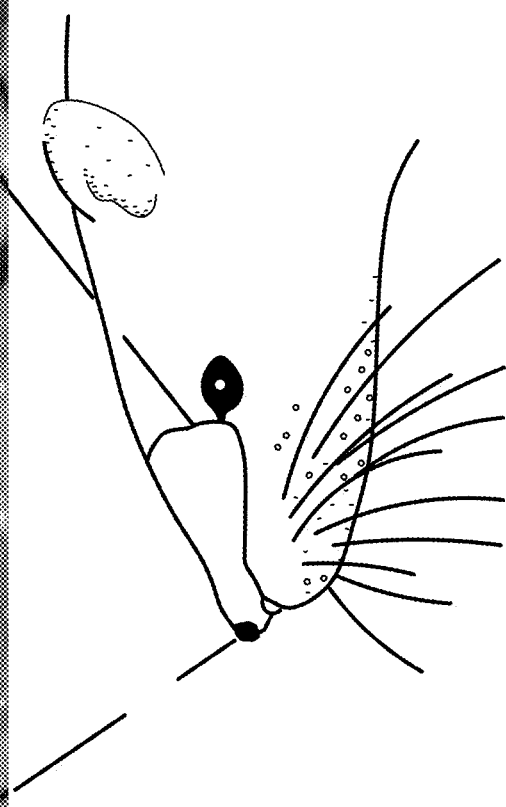
Figure 19:
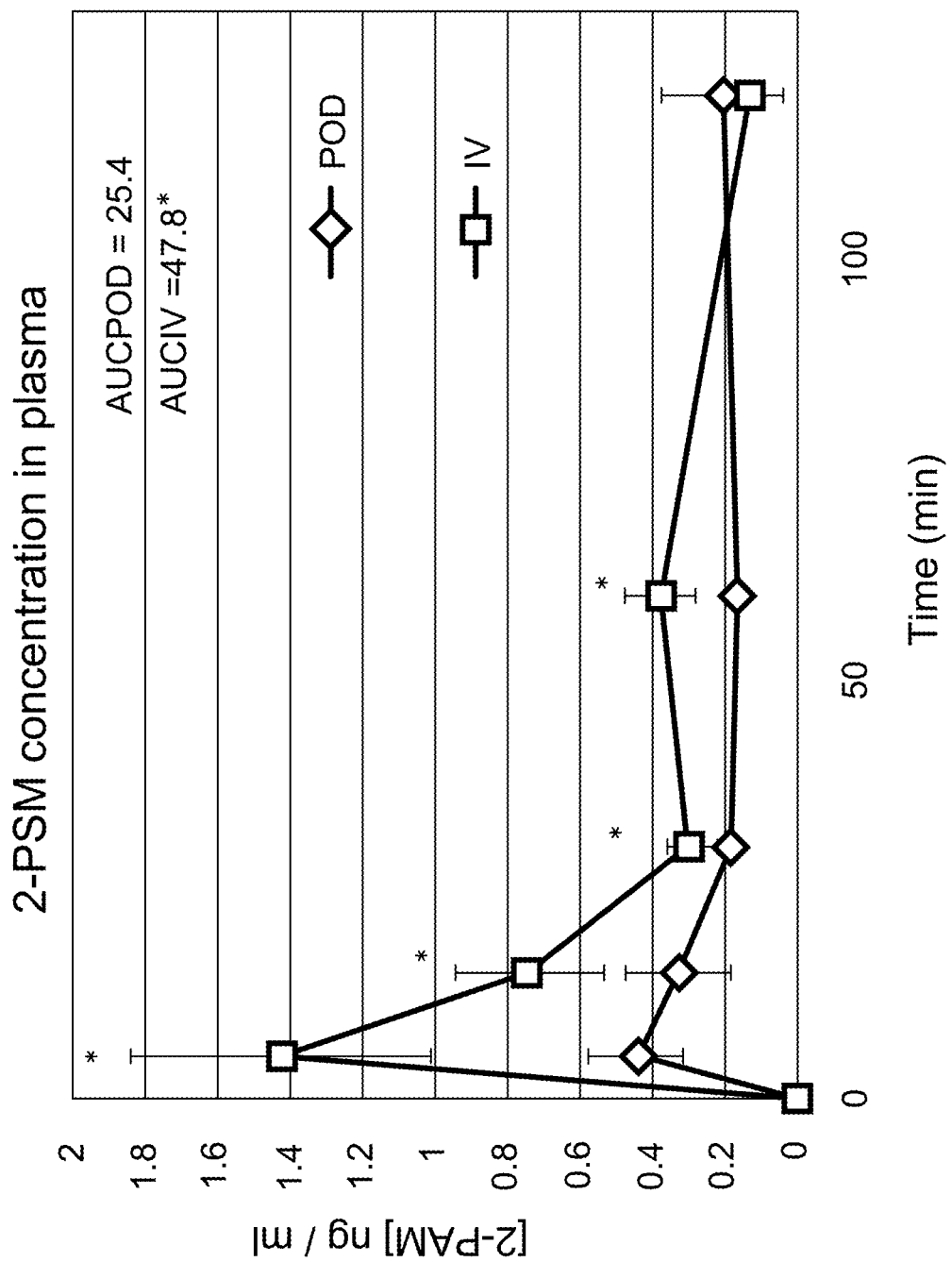

The construction of the rat use POD nasal aerosol device is illustrated in FIG. 17. A meter dose inhaler (MDI) can dispensing 25 µl hydrofluoroalkane 227 is attached to the plastic actuator. The actuator is in gas communication with a polytetrafluoroethylene frit which had a 50 μm pore size. The frit is in communication with the dose holding cylinder which is placed inside the body of the POD in order to create an aerosolized flow. On actuation the HFA propellant is converted to a gas by passing through the frit material and then it mixes with the dose and the dose and propellant mixture exits from the 23 gauge stainless steel tubing nozzle which is covered with a fluorinated ethylenepropylene liner was placed over the outside of the metal tip in order to protect the nasal epithelia from being damaged by the nozzle during use. The construction of the rat use POD device was successful and consistently delivered powder 2-PAM formulations with no measurable residual drug left in the device.

The basic operation of either POD device in rats was as follows. The animal was anesthetized with 5% isoflurane for 2 minutes to enable consistent administration. The rat was removed from the isoflurane chamber and placed in a supine position. The dose was loaded into the device and the nozzle was carefully placed 8.0 mm into the rat nasal cavity and pointed in the direction of the cribriform plate. Then the MDI can was pressed to discharge the dose into the rat nasal cavity. In addition, the dry powder dose chamber was weighed on a scale with a sensitivity of 0.1 mg (Mettler Toledo, Columbus, Ohio) before loading the dose, after the dose was placed in the dose loading chamber, and after firing to ensure that the correct dose was loaded into the device and that the complete dose was released into the rat nasal cavity.

The 2-PAM formulations were made with 0.1% coomassie blue dye in order to test nasal cavity deposition in rats. The animals were dosed using the dry power POD device as described above with a single dose of 2.5 mg dose of 2-PAM with coomassie blue. Shortly after administration was complete (<5 minutes), the animals were overdosed with 250 mg/kg pentobarbital. The nasal cavity was then bisected at the septum, the septum was removed, and the tissues were examined for dye localization. In addition the trachea and esophagus were dissected from the back of the mouth to the lungs to determine if the POD spray deposited any 2-PAM beyond the nasal cavity. This deposition study was performed with N=4 rats. The typical result of the deposition testing is shown in FIG. 18. In FIG. 18 the olfactory region of the rat nasal cavity in the upper panel is circled in white. The dark dye can be seen as being deposited primarily within this olfactory region.

A sensitive LC/MS method was established in order to determine the distribution of POD administered 2-PAM in both the plasma and the brain of rats. A fixed volume (20 μl) of 2Chlorolmethylpyridinium iodide d6 (Cerilliant, Palo Alto, Calif.) was added into each tissue and plasma sample to act as an internal standard. Tissue samples were homogenized in 3 mls of water. 60 μl of acetonitrile was added to the samples to cause protein precipitation. The samples were centrifuged for 10 minutes at 1000 g. An Agilent HPLC/MS series 1100 series B with autosampler (Agilent, Technologies, Inc., Santa Clara, Calif.) was used for quantification. The injection volume was 5 μl. The morphine samples were passed over a Phenomenex Synergi 4u PolarRP 80A (Agilent, Technologies, Inc., Santa Clara, Calif.) with a flow rate of 0.3 ml/min.

A standard curve was created on the day of analysis according to the same process described for the samples. Each standard curve was linear with a coefficient of linear regression R2>0.99. In addition, two quality control samples with a known amount of drug were processed on the day of analysis in order to ensure day to day consistency of the analytical assay.

This LC/MS method was successful and resulted in reproducible quantification of both tissue and brain samples. The 2-PAM detectable peaks were much higher than background in most cases. The sensitivity of this detection method was 0.05 μg/ml in plasma and 1.0 ng in brain tissue. This method could be used in future studies with primates or in clinical studies.

In the tissue distribution experiments, the animals were anesthetized with 5% isoflurane for two minutes. Then the animals were removed from the isoflurane induction box and placed in a supine position. The animals were then dosed with either the POD device (2.5 mg in a single 10 μl dose) or via intravenous injection (2.5 mg in 500 μl). Animals that were sacrificed 5 minutes after dosing remained under 2% isoflurane anesthesia until they were sacrificed. The animals sacrificed at the remaining time points were allowed to wake up from isoflurane anesthesia and placed back into housing. At 3 minutes before the sacrifice time the animals were again exposed to 5% isoflurane and then quickly overdosed with Beuthanasia-D (Schering—Plough Animal Health Corp, North Chicago, Ill.). Using IV 2-PAM and the aqueous POD formulation of 2-PAM, animals were sacrificed at 5, 15, 30, 60, and 120 minutes (N=6). Animals dosed with the dry powder 2-PAM POD formulation were sacrificed at 5 and 15 minutes (N=6).

Immediately after death, the animal was decapitated. Blood was collected from the trunk and placed in a microcentrifuge tube with 10 μl of 40 mM EDTA. The plasma was separated from the blood by centrifuging at 6,000 g for 10 minutes. Then the plasma was frozen until it was analyzed for 2-PAM concentration with the LC/MS method previously described. The base of the skull and the parietal bones were quickly removed from the head. The brain was removed within 2 minutes of sacrifice. The brain was placed in a microcentrifuge tube and frozen until it was analyzed for 2-PAM concentration with LC/MS.

A direct transport percentage (DTP %) to the brain was calculated in order to determine the amount of drug in the brain that was distributed directly from the nasal cavity to the CNS. The DTP % is used to estimate the amount of drug in the brain that cannot be accounted for by systemic distribution. The DTP as defined was calculated as follows:

Administration of the aqueous formulation of 2-PAM with POD resulted in lower systemic exposure and greater CNS exposure compared to an equivalent IV dose. The IV dose resulted in a typical plasma curve with the highest point at 5 minutes (FIG. 19). The POD administered 2-PAM resulted in plasma concentrations that were lower than the IV values, which is not expected given 2-PAM's limited absorption across the nasal respiratory epithelium into the blood stream. The total plasma AUC was significantly lower after POD administration compared to IV $$\frac{AUC_{brain(IV)}}{AUC_{plasma(IV)}} = \frac{B_X}{AUC_{plasma(nasal)}}$$

-continued $$DTP\ \% = \frac{AUC_{brain(nasal)} - B_X}{AUC_{brain(nasal)}} \times 100\%$$

administration.

Figure 20:
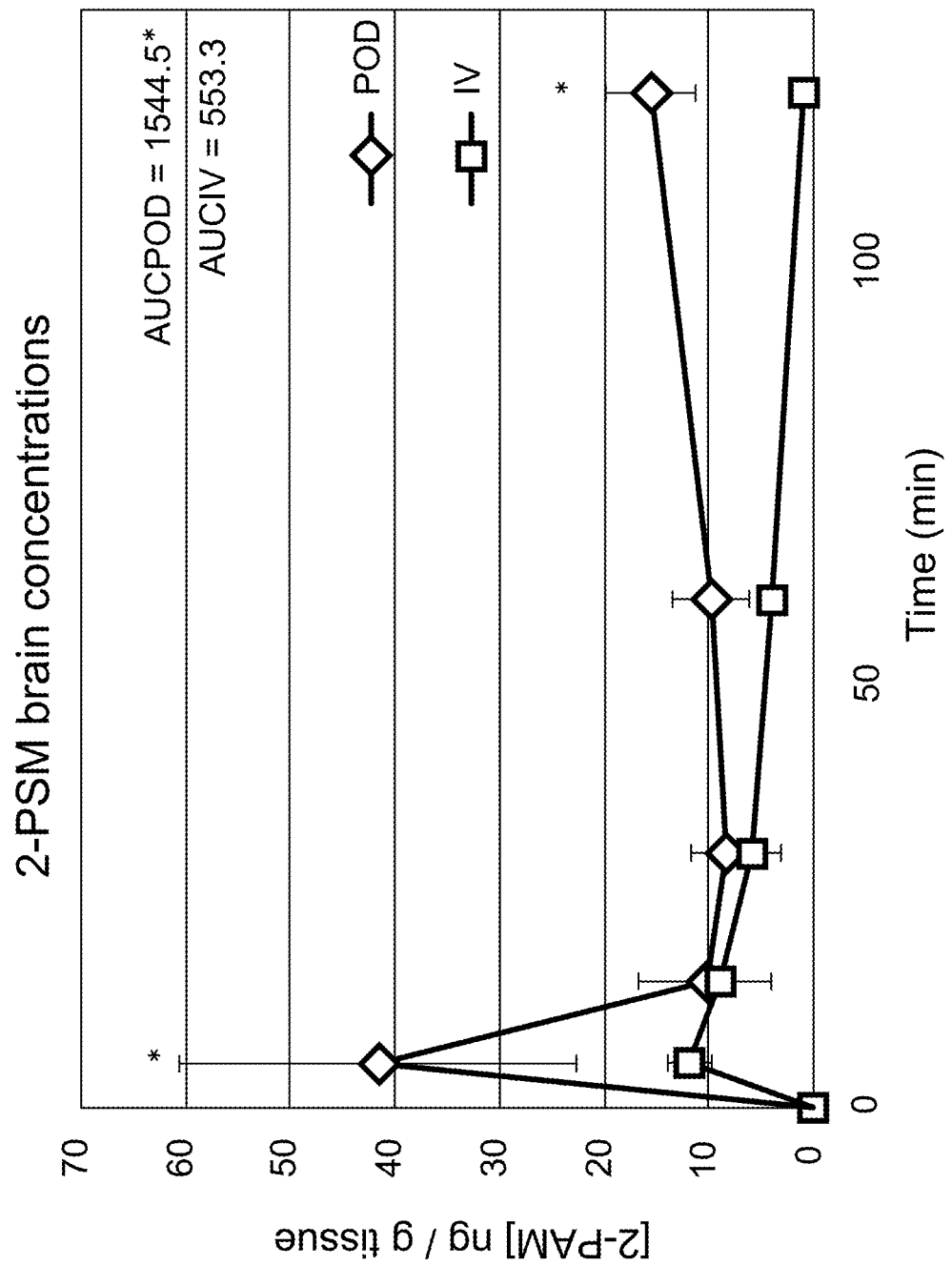

In contrast to the plasma values, the brain concentrations of 2-PAM after POD administration were significantly higher than after IV administration at both 5 and 120 minutes (FIG. 20). In addition, the total brain concentration AUC was significantly greater after POD administration compared to IV. Of interest for the application of 2-PAM as a nerve gas exposure treatment is the fact that at 5 minutes after administration, POD 2-PAM resulted in 3.5× the brain concentration compared to IV administration.

The brain-to-plasma ratios were significantly higher after POD 2-PAM compared to IV at every time point except for 30 minutes (Table 1). These increased ratios point to the fact that a portion of the drug was directly delivered to the brain from the nasal cavity, effectively bypassing the blood brain barrier. When the direct transport percentage (% DTP) was calculated it was found to be 80.9%. This % DTP can primarily be accounted for by the large brain values found 5 minutes after POD 2-PAM administration. Table 2 shows brain to plasma concentration ratios. At each time point except for 30 minutes, POD administration resulted in significantly greater brain to plasma ratios with a 15.25 fold increased brain to plasma ration after 5 minutes.

TABLE 1

| Time (min.) | POD | IV |
|---|---|---|
| 5 | 132.7* | 8.7 |
| 15 | 58.5* | 13.1 |
| 30 | 41.1 | 16.8 |
| 60 | 61.4* | 11.7 |
| 120 | 126.7* | 6.7 |

The powder formulation of 2-PAM administered via the POD device led to even greater 2-PAM concentrations in the brain (Table 2). The powder 2-PAM POD study was more limited than the aqueous formulation, but at 5 and 15 minutes after administration the powder formulation resulted in similar blood levels compared to the aqueous 2-PAM POD, but significantly higher brain concentrations.

TABLE 2

| time (min) | POD | IV | powder POD | | POD | IV | powder POD |
|---|---|---|---|---|---|---|---|
| | | | | | | | standard deviation |
| Plasma 2-PAM concentration (ng/g tissue) | | | | | | | |
| 5 | 0.44 | 1.42* | 0.46 | 5 | 0.1 | 0.4 | 0.27 |
| 15 | 0.33 | 0.73* | 0.38 | 15 | 0.1 | 0.2 | 0.11 |
| Brain 2-PAM concentration (ng/g tissue) | | | | | | | |
| 5 | 41.6 | 11.9 | 106.19* | 5 | 19.0 | 2.0 | 11.75 |
| 15 | 10.4 | 9.0 | 293.32 | 15 | 6.4 | 1.0 | 220.27 |

Table 2 shows distribution of the powder formulation of 2-PAM administered via POD. The powder formulation of POD resulted in plasma values at 5 and 15 minutes that were not significantly different than the liquid formulation of POD. However, the 2-PAM concentrations after POD administration of the powder formulation were significantly greater than either the aqueous POD 2-PAM or the IV 2-PAM. *=p<0.05

The pharmacokinetic and distribution experiments resulted in data supporting the potential of POD administered 2-PAM as a treatment for nerve gas exposure. The POD administration in both the aqueous formulation and the powder formulation resulted in high brain exposure within the first 5 minutes of administration.

Example 2

The device used in Example 2 is described in FIG. 3. The device in this example is referred to as a pressurized olfactory delivery (POD) device. In order to determine the amount of compound being delivered from the device to the olfactory region of the nasal cavity a method was developed for determining the percentage of dose deposited within key regions of a human nasal cavity model. This method relies on a quantitation by image analysis and is able to detect and quantitate deposition within 5 specified regions that describe the whole nasal model, including the upper olfactory region.

Figure 21:
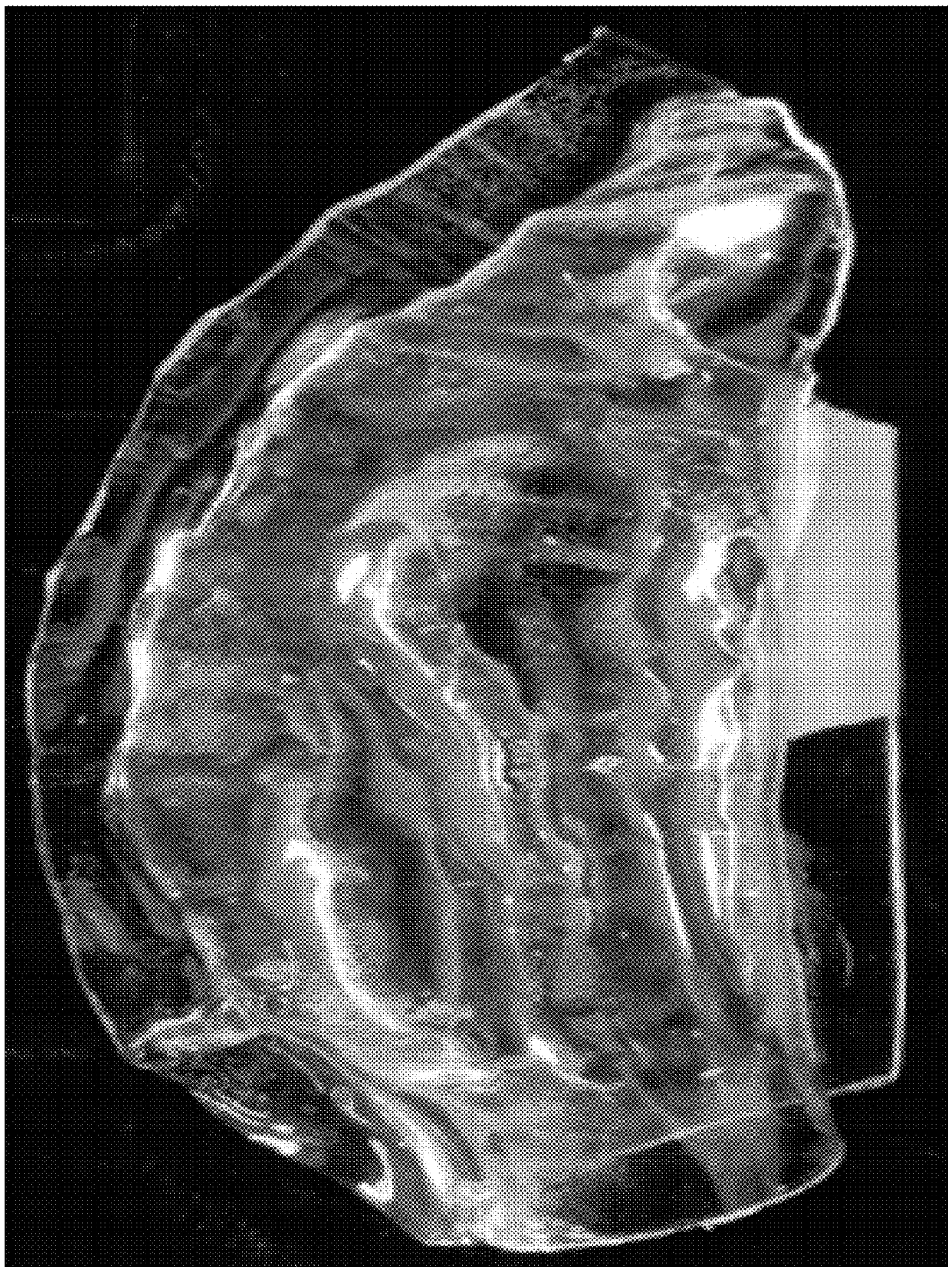

Materials: A human nasal cavity model was constructed from clear heat moldable plastic sheeting. (FIG. 21) This mold is thin-walled and is transparent to a blue light source that allows for the excitation of the indicator dye fluorescein used in the experimental doses. This human nasal cavity model was based on a computer model generated from MRI scans from multiple subjects (Liu, J Appl Physiol, 2009 March; 106(3):784-95). The model therefore represents an "average" human nasal cavity.

A stage for positioning the nasal models and aiming the POD device during targeting and actuation was designed and constructed. This stage was flexible enough in operation to allow for a wide set of aiming angles, both horizontal and vertical. By aiming the device at various angles with respect to the nasal cavity, the robustness of the device administration could be tested.

A thin walled transparent nasal model was prepared by coating the inside with a very thin layer of imitation mucus, which was simply a store bought hand sanitizer solution. The prepared model was then photographed in a custom made transilluminator/photo box as a blank reference for that particular experimental point. The model was then mounted onto the stage along with the POD device that has been loaded with a dose of 0.1 mg/mL Fluorescein/water. Immediately after POD actuation, the model was removed from the stage and held horizontally to prevent dose migrating. As soon as possible, the dosed model was placed in the transilluminator/photo box and photographed. The model was then washed under a stream of tap water and dried by shaking or forced air to be readied for another test. The two camera images were then digitally analyzed as described below to reveal deposition within the model.

Data processing of the blank and experimental images obtained was carried out with Image) software. For Image) to repeatedly compare images and perform background subtraction accurately, the digital photographs were taken with the model carefully held in the same register within the transilluminator/photo box. Image) performs three key functions: 1) the image was color processed with the RGB channel splitter. This function eliminates red and blue signals from the image, leaving primarily signal generated by the fluorescent signal from the fluorescein in the dose.

Figure 22:
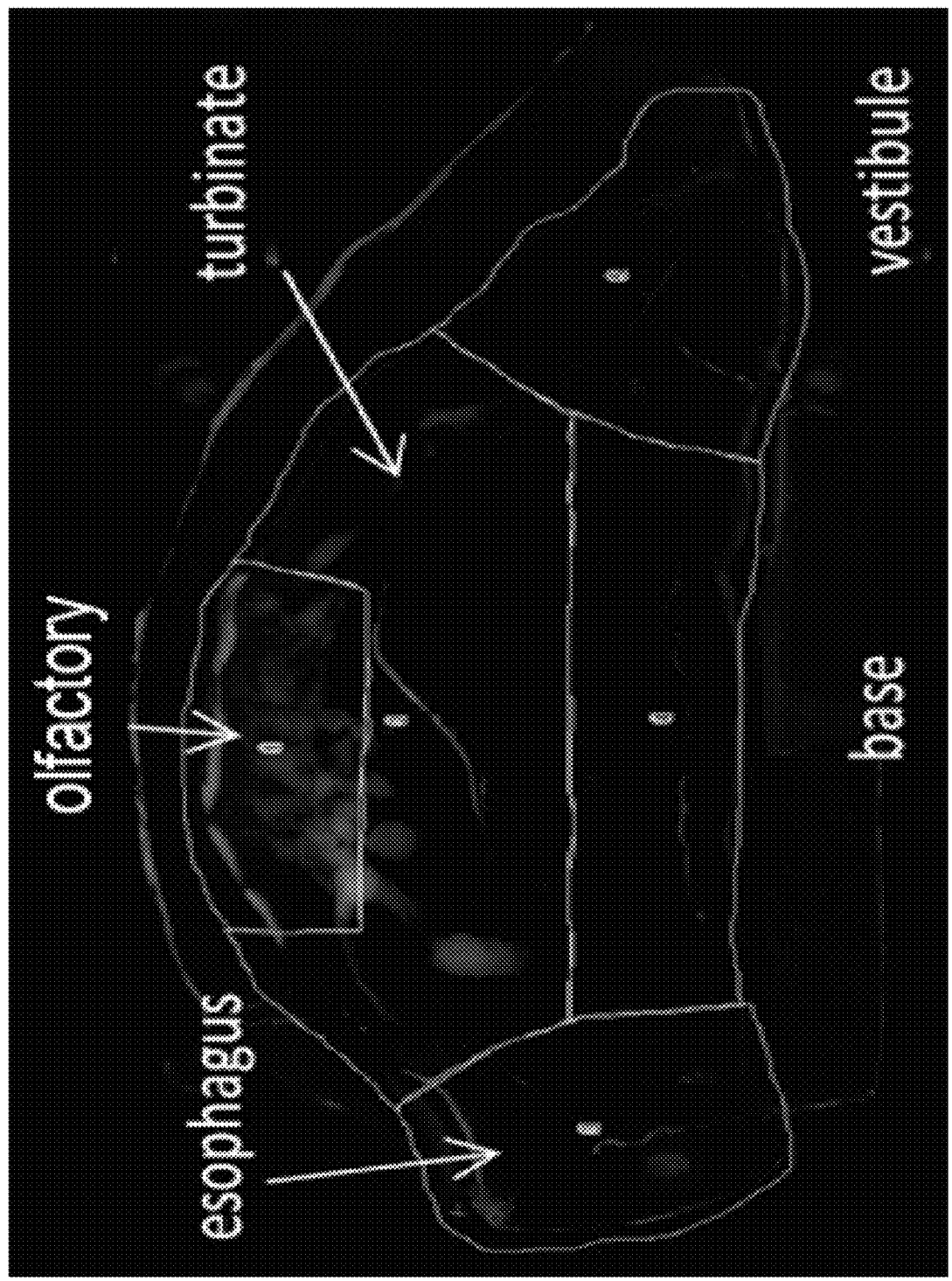
Figure 23:
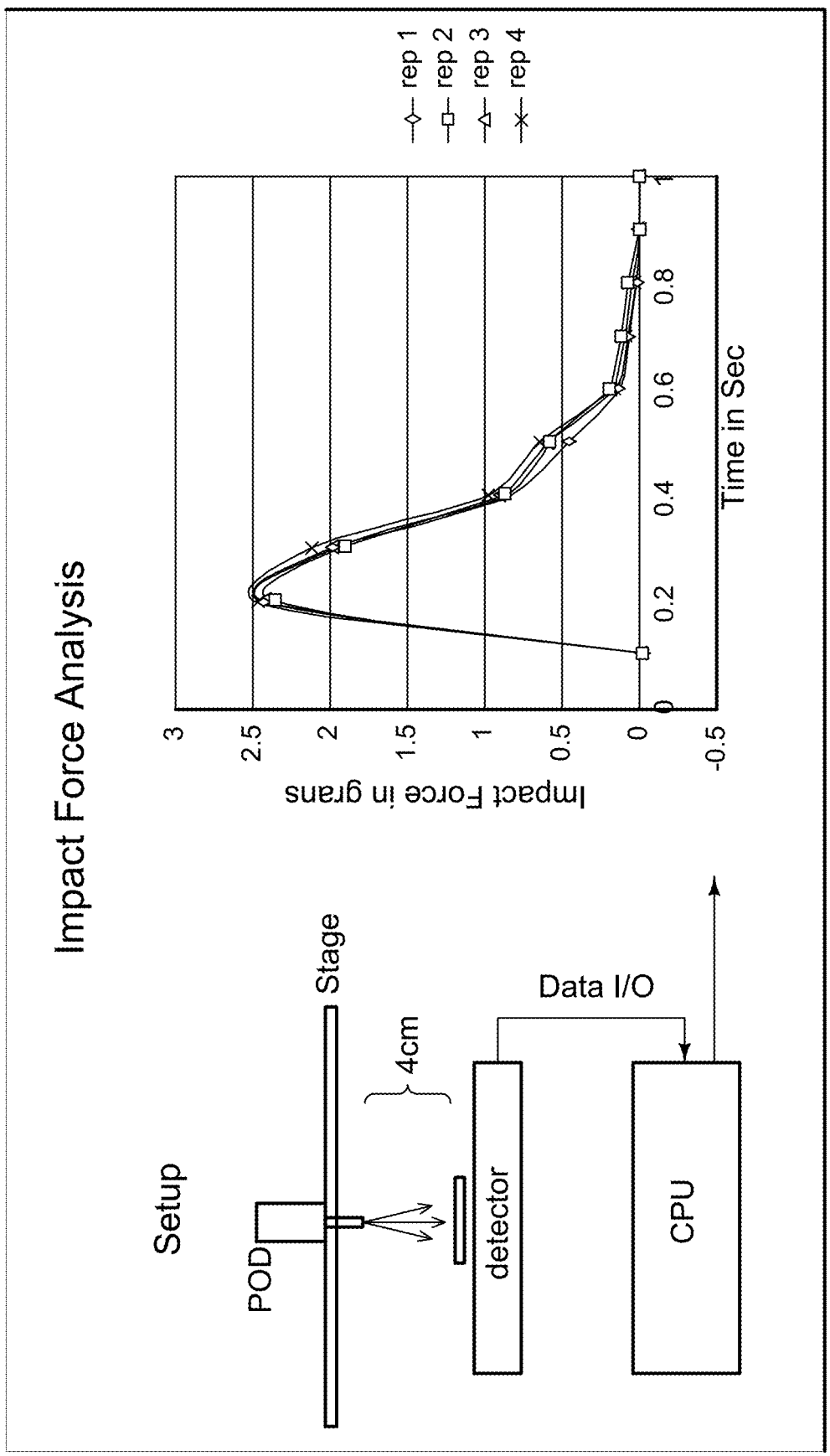

The Image) ROI manager allowed us to define five regions of interest; olfactory, turbinate, esophagus, base and vestibule which were quantitatively analyzed with each device administration. The regions are defined by the lines seen in FIG. 20 and these regions contain a specific area, in pixels that can be quantitated based on the signal intensity of the fluorescein. FIG. 22 also shows a typical spray pattern after a POD administration. The fluorescein administered into the model by the POD device can be seen as the light intensity on the dark background. It can be noted from FIG. 20 that a majority of the administered dose resides within the olfactory region of the human nasal model. Each pixel within these photos can possess a value of 0 to 255. The Measure function of ImageJ calculates the mean pixel value over each defined region of interest. The total signal recorded within a particular region of interest is therefore the product of the mean pixel value by the number of pixels measured. Of additional interest is the reported Max value. Because the photo cannot record more than 256 levels of signal, we conclude that the assay is not valid if we receive values of 255 in that column, because we cannot be sure if the actual signal is not significantly greater than 255 if it could be measured. Such a situation would have the effect of underreporting signal in that ROI because the signal is effectively clipped. For this reason, the camera exposure settings are critical to ensure that the signals recorded fall within the sensitivity range of the method yet allow for the maximal sensitivity of the method as well.

In addition, our calculations involved the subtraction of values obtained from a blank recording. This is because there is some stray light leakage and always therefore the potential for background fluorescence involving the model and the imitation mucus. Because these elements are not perfect in application, we do a background photo record each time and do a subtraction for each data point. This method offers the advantage of providing fractional deposition on more than one region of the nasal model. It also offers clear qualitative photo/visual confirmation of the quantitative results.

The results of a deposition study are shown in Table 3. Two different POD devices were used and are referred to as Tip #1 and Tip #2. Each Tip was administered into the nasal model N=3 times at either 0 degrees horizontal angle with respect to the septum or 5 degrees horizontally towards the septum. All POD administrations were administered at a vertical angle of 55 degrees with respect to the base of the nasal cavity.

TABLE 3

| Zone | Ave Distrib. | Std. Dev. | Ave Distrib. | Std. Dev. |
|---|---|---|---|---|
| | Tip #1, 0 degrees | | Tip #1, 5 degrees anterior | |
| Olfactory | 59.9 | 14.7 | 70.0 | 12.9 |
| Turbinate | 38.3 | 13.2 | 35.1 | 5.3 |
| Esophagus | −1.4 | 4.7 | −3.1 | 12.1 |
| Base | 3.6 | 4.1 | 0.7 | 2.5 |
| Vestibule | −0.4 | 4.6 | −2.7 | 2.8 |
| | Tip #2, 0 degrees | | Tip #2, 5 degrees anterior | |
| Olfactory | 58.2 | 3.9 | 61.1 | 7.3 |
| Turbinate | 49.1 | 12.1 | 38.5 | 3.6 |
| Esophagus | −4.6 | 5.2 | −0.1 | 4.6 |
| Base | −0.8 | 1.5 | 0.8 | 0.1 |
| Vestibule | −1.9 | 3.4 | −0.4 | 2.3 |

Example 3

Impaction force testing was used to compare several nozzle/dose chamber configurations with MDI drivers to several commercial nasal spray products. Impact impaction force is an ideal method to characterize plume characteristics that are important for dose delivery consistency, dose localization and dosing comfort and safety. A schematic of the experimental setup used in this example is shown in FIG. 23.

Impaction force measurements were carried out on a Mettler Toledo XS 64 with data output set at 10 per second coupled to an Apple MacBook Pro 2.2 GHz Intel Core 2 Duo processor, 4 GB 667 MHz DDR2 SDRAM via a ft. RS232 (Mettler Toledo) to USB cable (Gigaware) with supporting driver software. Data acquisition was carried out using Windmill Logger version 4.07, release 7 (Windmill Software Ltd.) in a Windows Vista virtual machine environment using Parallels Desktop 5 for Mac on the MacBook Pro. Data collected via Windmill Logger was imported directly into Microsoft Excel for graphical processing and analysis.

An impaction force stage was constructed to perform the measurements. This stage included means for accurate level and distance controls along with customized holders for the individual devices tested. Actuation was carried out manually. POD or commercial devices were aligned to impact the direct center of a 16.9 gram aluminum pan, 74 mm×80 mm. The pan was cleaned of dose/debris between each data shot. The distance from nozzle aperture to pan was 4 cm, consistent with the conclusions of Guo, et al. 2009 (Guo, J Pharm Sci., 2009, August; 98(8):2799-806.) as being within the 3 cm to 6 cm window of distances that generate the highest impaction forces and also consistent with our target distances in human nasal models. MDI triggered values obtained via valve actuation as tested was broadly insensitive from shot to shot when used as directed. The only effects seen were lower values if actuated very slowly.

Three commercial nasal spray products were tested in this Example: Rite Aid Pump Mist Nasal relief, oxymetasoline HCL 0.05%; NeilMed NasoGel For Dry Noses, Saline gel spray; and Rite Aid NoDrip Nasal Spray, pump, oxymetazoline, 0.05%.

The device used in this study is shown in FIG. 3 and is referred to as a pressurized olfactory delivery (POD) device in this Example. The POD nozzle was compared to the commercial spray pumps tested above. In this Example we tested the POD device under the same parameters as the commercial sprays using MDI canisters loaded with a 5% Ethanol, fluorescein mixed with either HFA 134a or HFA 227. The MDI valves were set to deliver a fixed volume of 50 uL.

The impaction forces measured for three commercial pump style nasal sprays were found to generate peak forces generally below 0.8 grams. These products are noted for either generating very broad spray patterns or slow moving streams of gelatinous material. The forces generated from these tested products fall well below the forces quoted by Guo et al., 2009 of 3.0 to 4.9 grams. The POD device generated impaction force measurements with peaks near 4 grams with an average of just below 3 grams of force when the more highly volatile HFA 134a was used. This force dropped to below 2 grams when HFA 227 was used instead. In either case, the impaction forces for the POD device also fell well within the range of impaction forces measured for commercial MDI device by Guo et al., 2009, which showed a maximum value of 6.5 grams.

It was found that the impaction forces measured are affected by the HFA type used and the volume of HFA dispensed by the MDI canister. Also the dose chamber and nozzle configuration have impacts on impaction forces. In no case have we measured forces greater than that measured for the one commercial product referenced in the Guo et al. paper.

Example 4

In this example the device, referred to as a pressurized olfactory delivery (POD) device, was tested to determine if the device would release a cold temperature spray. This testing involved the measurement of surface temperature changes on the target region caused by HFA POD. A schematic of the experimental setup used in this example is shown in FIG. 24.

The hydrofluoroalkane (HFA) used as a propellant in the POD device is released from the metering can as a liquid. Very quickly after release the HFA vaporizes and expands to form the pressure impulse that drives the dose through the POD nozzle. It is also a characteristic of the HFA POD that the HFA gas is expelled toward the target along with and after the dose is delivered. The expansion of the HFA causes a marked drop in temperature of the propellant gas during the firing process. In order to establish whether this temperature drop is transferred to target tissues and to what extent, we designed and performed experiments to detect and measure the surface temperature of targets during and immediately after they were impacted by the device while only releasing HFA or while releasing a mixture of HFA and liquid compound (as it would be used for administering a liquid drug product).

Materials: Kintrex infrared thermometer, model IRT0421, capable of measuring surface temperature without actually contacting the surface being tested. Temperatures are reported in degrees Fahrenheit. An actuator fitted with a HFA 134a canister designed to deliver 50 uL of propellant, Kimwipe paper wipes, petri dish, 1% agarose/water 3 tips, including a high impedance, low impedance nozzle and open configuration/absent frit.

Figure 24:
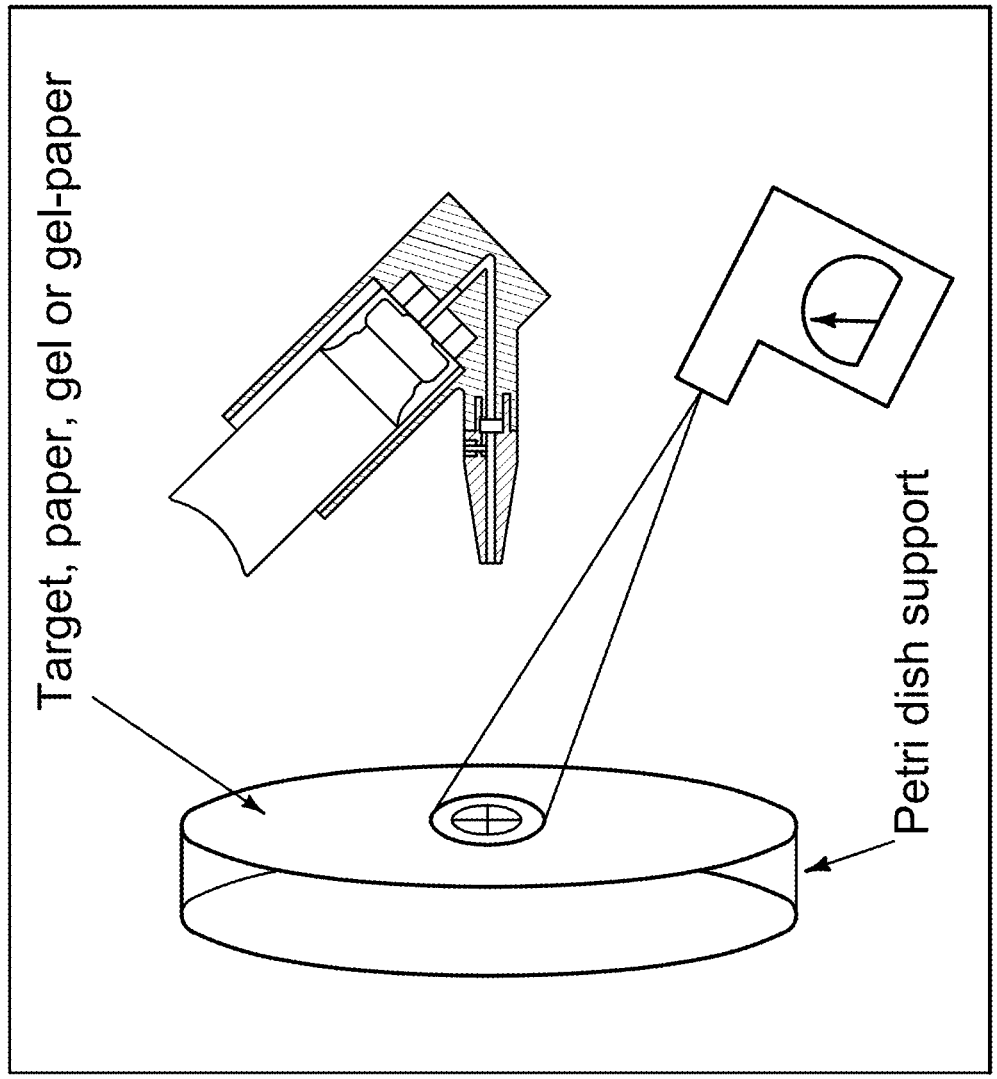

FIG. 24 illustrates the experimental setup for measuring temperature changes during the firing of the POD device under different conditions. The thermometer was positioned 4 cm from the target. At that distance the thermometer "sees" and reads from a circular spot of 0.33 cm diameter (target circle in FIG. 24).

Three tip configurations were tested. 1. A tip with a high impedance nozzle fitted. A high impedance nozzle is sufficiently restrictive to flow of HFA gas that the nozzle is the limiting feature of the POD system. It releases gas over a longer duration. 2. A tip with a low impedance nozzle fitted. In this tip, the frit, near the actuator end of the tip is actually the limiting feature of the device. It releases gas faster than the high impedance nozzle. 3. A tip that contains neither a nozzle nor frit. This tip offers essentially no restriction to HFA gas or liquid flow through the device. With these three configurations, we expected to understand how restrictions on gas flow affects the temperature of target upon firing and also define the distinct role that the Teflon frit plays in diffusing and facilitating the transition of HFA from the liquid state to the gaseous state.

We also tested the effect of target proximity to the nozzle with respect to temperature changes experienced by the target. We fired from a distance of 4 cm and 2 cm.

In addition, we fired the device at three different targets. 1) We used a very low mass target. This target was constructed of a Kimwipe tissue paper. We anticipated that a low mass target would have a very low thermal inertia and therefore would display much more change in temperature upon firing. 2) We created a mock epithelium (epithelium mimic #1) by overlaying a Kimwipe tissue paper wipe onto 1% agarose/water. This was designed so that the thermometer would react to a similar color and texture surface as the low mass target. 3) Another mock epithelium (epithelium mimic #2) made from 1% agarose/water with Kimwipe paper embedded just below the surface (less than 0.5 mm) of the agarose. This target was designed in case the thermometer would react to the paper layer just below the essentially clear agarose to see if the temperature effects were mostly superficial.

In addition, some temperature measurements were done on the epithelium mimics when a 50 μL water dose was added to the setup. Table 4 summarizes the temperature changes detected upon the firing of only hydrofluoroalkane propellant. The temperature change in degrees Fahrenheit is represented by the symbol A. We believed and confirmed that this would create the conditions for the most dramatic temperature changes. With the low mass, low thermal inertia paper target, the greatest temperature change was when no frit or nozzle was installed in the tip. The data for this condition was closely clustered near −25 F. Indeed, with this setup particulate or mist can be seen ejecting from the end of the tip, suggesting that a certain fraction of the HFA remains liquid through its transit through the actuator body and tip. Any liquid HFA that were to reach the target would then ablate on the target and could explain the dramatic temperature drops seen.

TABLE 4

| | 4 cm target | | 2 cm target | | No Frit/Nozzle | |
|---|---|---|---|---|---|---|
| | −Δ | −ΔMax | −Δ | −ΔMax | −Δ | −ΔMax |
| Low Impedance Nozzle | | | | | | |
| Low mass | 2.5 | 3.7 | 4.4 | 5.6 | 25.2 | 27.2 |
| epithelium mimic #1 | 0.5 | 1.1 | 1.1 | 1.9 | 3.9 | 4.4 |
| epithelium mimic #2 | 1.0 | 1.5 | 0.9 | 1.8 | 4.2 | 5.3 |
| High Impedance Nozzle | | | | | | |
| Low mass | 1.9 | 3.2 | 2.9 | 5.2 | 25.2 | 27.2 |
| epithelium mimic #1 | 1.2 | 3.5 | 1.2 | 1.6 | 3.9 | 4.4 |
| epithelium mimic #2 | 1.7 | 2.6 | 2.5 | 3.2 | 4.2 | 5.3 |

In contrast, all other experimental conditions resulted in far smaller temperature drops at the target. Modest drops of 3-4 F were seen with the unobstructed tip on the epithelium mimics. It is clear the thermal capacity of the target is critical in this analysis.

Inclusion of the Teflon frit and nozzle into the tip resulted in even smaller temperature drops. Against the low mass tissue target, the low impedance nozzle resulted in the greatest temperature drop, with a maximum value of 5.6 F at a distance of 2 cm. The high impedance nozzle resulted in slightly lower temperature drops. Typical values were 3 F or less.

There is a slight trend depending on tip distance to target. As would be expected, shots at closer range can result in lower temperatures at the target.

When a dose load of 50 μL water was added to the tip that included a Teflon frit and low impedance nozzle very small temperature effects were seen. The data ranged from a 0.5 F drop to a 0.2 F increase. It was determined that with the small changes seen and the difficulty of handling the liquid doses in the experimental setup that we would not be able to get reliable data with liquid doses. However we believe the data collected with the liquid doses in consistent with predicted outcomes.

The hydrofluoroalkane propellant used in the POD device will have very minimal effects on the temperature of impacted tissues. The data show the Teflon frit's function in the POD and the decrease in the temperature of the impacted site when only HFA is delivered. In addition, a typical load of 50 μL will itself likely reduce any temperature effects.

Example 5

In assaying the targeting of the human olfactory region with a drug product, 2 formulations of 2-PAM were delivered from the device into a human nasal cavity model and analyzed for olfactory deposition.

A silicon rubber human nasal cavity model was purchased from Koken Inc. (Tokyo, Japan). A trace amount (0.1%) of Coomassie blue (Sigma Aldrich, St. Louis, Mo.) was mixed into the dry powder 2-PAM. The dry powder 2-PAM and Coomassie blue were crushed to a homogenous powder with a mortar and pestle. 0.1% rhodamine B was added into the aqueous formulation (250 mg/ml) for visualization within the nasal cavity model. The dry powder formulation was sprayed into the model nasal cavity (N=10) with the device and pictures were taken to get a qualitative measure of deposition in the olfactory region. The pictures were judged as to whether a majority of the powder 2-PAM was deposited in the olfactory region.

The same was done with the aqueous formulation, and the deposition in the olfactory region was also quantified by weight for this formulation (N=10). The olfactory region of the nasal cavity model was cut from the model so that it was removable. The olfactory region was weighed before the POD spray and after the spray and the percent of dose administered to the olfactory region was calculated by weight.

The dry powder 2-PAM formulation administered into the human nasal cavity was effective in depositing of drug in the olfactory region. Qualitative examination of 10 administration attempts into the model consistently was judged to show a majority of drug (about 50% or greater) in the olfactory region. In addition to depositing drug on the olfactory region, the dry powder POD device deposited a substantial amount of the 2-PAM dose at the interface with the cribriform plate area of the model which separates the olfactory region of the nasal cavity from the brain.

The aqueous 2-PAM formulation displayed similar patterns of deposition in the human nasal cavity model as the dry powder formulation. In addition to the qualitative photos of the human nasal cavity, 62.6±9.6% of the dose was determined to deposit in the olfactory region of the nasal cavity.

Example 6

Comparison of a POD Device for a Unit Dose Container and a Clinical POD Device with Injection Port To construct a POD device for a unit dose container, a clinical POD device was bored out to accept a tube the size of the unit dose container. The tube was a proxy for example, commercially, for a blow fill sealed unit dose container. The tube for the unit dose container was sealed at the distal end by the diffuser; in this construction the diffuser was a frit. Into the hollow of the tube for the unit dose container was inserted a propellant injector in the form of a cannula, the cannula had an outer diameter smaller than the inner diameter of the hollow of the tube of the unit dose container. The cannula sealed the distal end of the tube for the unit dose container. The cannula was inserted a depth into the tube hollow so that side orifices on the cannula were located inside the tube hollow. The cannula conveyed or delivered a propellant into the tube via the side orifices. The proximal end of the tube for the unit dose container was left open to receive a nozzle. The unit dose container was not actively punctured by the propellant injector and the propellant injector cannula was inserted into the tube for the unit dose container.

The unit dose container tube in this example was filled so that: 1) dose was filled so it sat at the distal portion of the tube (e.g. dose sat near the frit), 2) dose was filled so it sat near the nozzle or proximal portion of the unit dose container and 3) dose was filled so it sat evenly spread along the entirety of the unit dose container. The POD device was actuated and residual and high speed video was collected of each deposition. Residual data was obtained by mass measurements.

| Fill condition ▼ | n ▼ | mθ (mg) ▼ | mf (mg) ▼ | mn (mg) ▼ | residual (mg) ▼ | residual (%) ▼ | dose (mg) ▼ |
|---|---|---|---|---|---|---|---|
| 1 | 1 | 1943.6 | 2043.9 | 1962.4 | 18.8 | 19% | 100.3 |
| 1 | 2 | 1944.8 | 2046 | 1962.5 | 17.7 | 17% | 101.7 |
| 1 | 3 | 1942.9 | 2043.7 | | | | 100.8 |
| 2 | 1 | 1944.8 | 2045.4 | | | | 100.6 |
| 2 | 2 | 1945.3 | 2046.5 | 1953.5 | 8.2 | 8% | 101.2 |
| 2 | 3 | 1946.1 | 2045.8 | 1951.6 | 5.5 | 5% | 100.7 |
| 3 | 1 | 1944.8 | 2043.5 | 1964.9 | 20.1 | 20% | 98.7 |
| 3 | 2 | 1946.9 | 2047.3 | 1965.3 | 18.4 | 18% | 100.4 |
| 3 | 3 | 1948.1 | 2048.5 | 1957.3 | 9.2 | 9% | 100.4 |

Example 7

Puncture Design

Puncture members were tested for puncturing the distal, proximal, or both ends of the unit dose container. In this example, the puncture member is shaped like a cylinder. In this example where the puncture member is shaped like a cylinder, the outer diameter of the cylinder is 0.0625 cm at the distal base, non puncturing end of the puncture member. The proximal end of the puncture member is located immediate to the unit dose container when assembled with the POD device. From a center line thru the center plane of each cylinder, at the proximal end, five different angles of taper at the proximal end of the device were tested. The angles of taper, with respect to a center plane, are: 90 degrees, 60 degrees, 45 degrees, 30 degrees and 15 degrees as shown in FIG. 42(*a*), (*b*), (*c*), (*d*), and (*e*). In this example, the puncture members are made of aluminum, however, any suitable material such but not limited to as PVC, PEP, PP, ABS and COC may be utilized.

To test the puncture members, capsules containing a liquid or a powder was used in this example. The capsules used were a dry powder inhaler (DPI) capsule and a gel capsule. The capsules were held in a capsule holder and an Instron Puncture Tester, 5900 series model, from Instron, Norwood, Mass., USA was used to puncture.

Gel Capsules

Gel capsules were punctured at the rate of 1 ipm, 10 ipm, and 20 ipm (inch per minute). Of the punctures performed, the 15 degree puncture provided for the lowest maximum force to puncture the capsule.

| Specimen | Puncture | Rate | Fracture Characteristic |
|---|---|---|---|
| 1 | 90 | 1 | No fracture, compression |
| 2 | 90 | 10 | No fracture, compression |

| Specimen | Puncture | Rate | Fracture Characteristic |
|---|---|---|---|
| 3 | 90 | 20 | No fracture, compression |
| 4 | 60 | 1 | No fracture, compression |
| 5 | 60 | 10 | No fracture, compression |
| 6 | 60 | 20 | No fracture, compression |
| 7 | 45 | 1 | No fracture, compression |
| 8 | 45 | 10 | No fracture, compression |
| 9 | 45 | 20 | No fracture, compression |
| 10 | 30 | 1 | Small puncture, little compression |
| 11 | 30 | 10 | Small puncture, lots of compression |
| 12 | 30 | 20 | Small puncture, little compression |
| 13 | 15 | 1 | Very small puncture, no compression |
| 14 | 15 | 10 | Fractional puncture, no compression |
| 15 | 15 | 20 | Fractional puncture, no compression |

FIG. 43(*a*), (*b*), (*c*), (*d*) and (*e*) show a progression of decrease in extension from a puncture with an angle of 90 degrees to a puncture with an angle of 15 degrees. The puncture with an angle of 15 degrees showed consistently the least extension; see FIG. 43(*a*), (*b*), (*c*), (*d*) and (*e*).

DPI Capsule

The experiment described immediately above in this Example 7 was conducted also with DPI capsules.

| Specimen | Puncture | Rate | Fracture Characteristic |
|---|---|---|---|
| 16 | 90 | 1 | Significant compression |
| 17 | 90 | 10 | Significant compression |
| 18 | 90 | 20 | Significant compression |
| 19 | 60 | 1 | Significant deformation |
| 20 | 60 | 10 | Significant deformation |
| 21 | 60 | 20 | Significant deformation |
| 22 | 45 | 1 | Some compression then clean puncture |
| 23 | 45 | 10 | Small indents, then puncture (fracture) |
| 24 | 45 | 20 | Small indents, then puncture (fracture) |
| 25 | 30 | 1 | Small indents, then puncture |
| 26 | 30 | 10 | Small indents, then puncture (some fracture) |
| 27 | 30 | 20 | Little indent, functional puncture |
| 28 | 15 | 1 | Very little indent, slight fracturing |
| 29 | 15 | 10 | Very little indent, slight fracturing |
| 30 | 15 | 20 | Very little indent, slight fracturing |

With the dry powder inhaler capsule, from the table immediately above it is apparent that a 30 degree angle of the puncture provided puncture without fracturing of the dry powder inhaler capsule. FIGS. 44 (*a*), (*b*), (*c*), (*d*), and (*e*) show the extension over the dry powder inhaler. At 30 degree angle with a DPI capsule results in acceptable puncture with the least force to puncture and punctured with the least extension/displacement.

We determined in both the gel and dry powder capsule each can accommodate user variations in the amount of force per square inch that the user can apply. Angle of puncture has an impact. The sharper the puncture angle, the less maximum puncture force and the smallest required displacement to puncture the capsules.

BFS Film

BFS film of 6 mm thickness was tested using an Instron Puncture Tester, 5900 series model, from Instron, Norwood, Mass., USA using the five puncture devices shown in FIGS. 42 (*a*), (*b*), (*c*), (*d*), and (*e*) and described in this example.

| Specimen | number | Puncture | Rate | Characteristic |
|---|---|---|---|---|
| 1 | 1 | 90 | 1 | Despite the blunt puncture, the deformation region was limited to the cross sectional area |
| 2 | 2 | 90 | 1 | |
| 3 | 3 | 90 | 1 | |
| 4 | 1 | 90 | 10 | Identical to the 1 ipm rate puncture |
| 5 | 2 | 90 | 10 | |
| 6 | 3 | 90 | 10 | |
| 7 | 1 | 90 | 20 | Identical to the 1 ipm and 10 ipm puncture rates |
| 8 | 2 | 90 | 20 | |
| 9 | 3 | 90 | 20 | |
| 10 | 1 | 60 | 1 | Slower initial ramp than the 90 degree |
| 11 | 2 | 60 | 1 | |
| 12 | 3 | 60 | 1 | |
| 13 | 1 | 60 | 10 | Similar initial ramp to 1 ipm but longer tail |
| 14 | 2 | 60 | 10 | |
| 15 | 3 | 60 | 10 | |
| 16 | 1 | 60 | 20 | Very similar puncture to 10 ipm profile |
| 17 | 2 | 60 | 20 | |
| 18 | 3 | 60 | 20 | |
| 19 | 1 | 45 | 1 | Lower force but longer tail than 60 degree puncture |
| 20 | 2 | 45 | 1 | |
| 21 | 3 | 45 | 1 | |
| 22 | 1 | 45 | 10 | Identical to 1 ipm |
| 23 | 2 | 45 | 10 | |
| 24 | 3 | 45 | 10 | |
| 25 | 1 | 45 | 20 | Very similar to 1 ipm and 10 ipm |
| 26 | 2 | 45 | 20 | |
| 27 | 3 | 45 | 20 | |
| 28 | 1 | 30 | 1 | Significantly less tail, lower force, and less abrupt puncture than 45 degree |
| 29 | 2 | 30 | 1 | |
| 30 | 3 | 30 | 1 | |
| 31 | 1 | 30 | 10 | Very similar to 1 ipm |
| 32 | 2 | 30 | 10 | |
| 33 | 3 | 30 | 10 | |
| 34 | 1 | 30 | 20 | |

-continued

| Specimen number | Puncture | Rate | Characteristic |
|---|---|---|---|
| 35 | 2 | 30 | 20 | |
| 36 | 3 | 30 | 20 | |
| 37 | 1 | 15 | 1 | Much lower force profile |
| 38 | 2 | 15 | 1 | |
| 39 | 3 | 15 | 1 | |
| 40 | 1 | 15 | 10 | Similar to 1 ipm |
| 41 | 2 | 15 | 10 | |
| 42 | 3 | 15 | 10 | |
| 43 | 1 | 15 | 20 | Similar to 1 and 10 ipm |
| 44 | 2 | 15 | 20 | |
| 45 | 3 | 15 | 20 | |

FIG. 45 shows a correlation that the steeper angle puncture reduced the maximum puncture force.

Example 8

Determination of Puncture and Residuals of Various Puncture Devices

Distal Puncture

Various puncture members were constructed and tested for their ability to puncture a unit dose container and to measure the amount of residual drug remaining in the container. Pass criteria for the puncture member was no more than 10% residual.

The following rear puncture members were made; each puncture member is essentially cylindrically shaped and has an opening its proximal end, where proximal end is the end closest to the nozzle, except in one illustration of this Example where the rear puncture member is sealed or closed at the proximal end:

A puncture member having an outer diameter of 1.651 mm; an inner diameter of 1.194 mm; and a wall thickness of 0.229 mm (comparable to 16 gauge on the Birmingham Wire Gauge); (A-16)

A puncture member having an outer diameter of 0.8192 mm; an inner diameter of 0.514 mm; and a wall thickness of 0.1524 mm (comparable to a 21 gauge on the Birmingham Wire Gauge); (B-21)

A puncture member having an outer diameter of 0.8192 mm; an inner diameter of 0.514 mm; and a wall thickness of 0.1524 mm (comparable to a 21 gauge on the Birmingham Wire Gauge); closed end to the puncture member and a single orifice located on a lateral of the puncture member; (C-21)

A puncture member having an outer diameter of 0.5144 mm; an inner diameter of 0.260; and a wall thickness of 0.1270 mm (comparable to a 25 gauge on the Birmingham Wire Gauge); (D-25)

A puncture member made of three cylinders each having an outer diameter of 0.3112 mm; an inner diameter of 0.159 mm; and a wall thickness of 0.0726 mm (comparable to a 30 gauge on the Birmingham Wire Gauge). The three cylinders for the puncture member were arranged so that the three channels were parallel to each other on the long axis and each at the point of an isosceles triangle in the plane of puncture; (E-30) and A puncture member having an outer diameter of 0.8192 mm; an inner diameter of 0.514 mm; and a wall thickness of 0.1524 mm (comparable to a 21 gauge on the Birmingham Wire Gauge); closed end to the puncture member and a two orifice located on a lateral of the puncture member; the two orifices located 180 degrees apart (F-21).

A unit dose container was made of flexible tubing (e.g. Tygon tubing) of approximately 4 mm outer diameter and 27 mm length. The distal end of the tubing was sealed (by, for example, using a rubber stopper). The surrogate unit dose is filled with liquid; in this instance with 20 microgram/ml fluorescein. The unit dose container was punctured by one of the puncture members, video was taken of the dose release, and measurements were made of residual drug. The following table shows the results of the residuals remaining.

| | Average weight 100 ul of fluoroscein solution 98.3 | | | | | |
|---|---|---|---|---|---|---|
| Puncture Unit | empty weight (mg) | full weight (mg) | post weight (mg) | ul loaded | residual (ul) | residual (ul) |
| A-16 | 1698.3 | 1796.2 | 1704.8 | 100 | 8.6 | 6.3895 |
| A-16 | 1697.9 | 1796.2 | 1705.1 | 100 | 8.9 | 7.0776 |
| A-16 | 1702 | 1800.4 | 1711.8 | 100 | 11.4 | 9.6334 |
| B-21 | 1689.6 | 1788.5 | 1695.4 | 98.9 | 5.8 | 5.7014 |
| B-21 | 1689.2 | 1787.5 | 1694.4 | 98.3 | 5.2 | 5.1116 |
| B-21 | 1688.9 | 1787.1 | 1694.2 | 98.2 | 5.3 | 5.2099 |
| C-21 | 1687 | 1785.5 | 1691.2 | 98.5 | 4.2 | 4.1286 |
| C-21 | 1687.3 | 1785.5 | 1690.2 | 98.2 | 2.9 | 2.8507 |
| C-21 | 1689.3 | 1787.9 | 1694.1 | 98.6 | 4.8 | 4.7184 |
| D-25 | 1710.6 | 1787.5 | 1724 | 76.9 | 13.4 | 13.1722 |
| D-25 | 1689.4 | 1789.1 | 1702.8 | 99.7 | 13.4 | 13.1722 |
| D-25 | 1688.8 | 1787.5 | 1700 | 98.7 | 11.2 | 11.0096 |
| E-30 | 1686.8 | 1795.1 | 1707.3 | 108.3 | 20.5 | 20.1515 |
| E-30 | 1697.5 | 1792.3 | 1704.9 | 94.8 | 7.4 | 7.2742 |
| E-30 | 1696.7 | 1795 | 1706.4 | 98.3 | 9.7 | 9.5351 |
| F-21 | 1693.3 | 1790.1 | 1697.2 | 96.8 | 3.9 | 3.8337 |
| F-21 | 1693.5 | 1792.1 | 1699.6 | 98.6 | 6.1 | 5.9963 |
| F-21 | 1693.3 | 1791.9 | 1699.3 | 98.6 | 6 | 5.898 |

Minimal drug residuals were obtained with the C-21 and F-21 puncture devices, as shown in FIG. 46. Interestingly, B-21, a puncture member without a lateral orifice, had similar residual drug as C-21 and F-21, puncture members with lateral orifices. The lateral orifices seem to correlate with reduced drug residual. Whereas, decrease in the size of the puncture mechanism does not correlate with a decrease in residual drug. C-21 seems to provide for the least residual drug with residual drug being consistently under 5 microliters.

Proximal Puncture

Following the testing of the distal puncture member for residual drug, a POD device was constructed for acceptance of a distal C-21 puncture member and a proximal puncture member of two varieties:

An outer diameter of 1.270 mm; an inner diameter of 0.838 mm; and a wall thickness of 0.216 mm; ((comparable to a 18 gauge on the Birmingham Wire Gauge); T-18A) and An outer diameter of 1.270 mm; an inner diameter of 0.838 mm; and a wall thickness of 0.216 mm; closed tip to the puncture device and a single orifice located on a lateral of the puncture device (T-18B).

The end of the proximal puncture member that would come into contact with the unit dose container to puncture it was beveled.

The same method as in Example 8, Distal Puncture, above was used, with C-21 puncturing the distal end and either T-18A or T-18B puncturing the proximal end of the unit dose container. Results are shown in the table below:

| Results | Average Residual microliter | Standard deviation |
|---------|----------------------------|--------------------|
| T-18A   | 3.23                       | 0.99               |
| T-18B   | 6.43                       | 2.01               |

T-18A, without an orifice located on the lateral of the unit dose, decreased the residual.

Overall, for the distal and proximal puncture, having the gas exit perpendicular to the central axis of the dose holding chamber led to decreased residuals.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

We claim:

1. A device for delivering a compound to an olfactory region of a nasal cavity comprising:
   a housing body, the housing body configured to hold a canister configured to contain a propellant,
   a tip configured to removably couple to the housing body of the device, the tip comprising:
      a container cavity configured to receive a unit dose container, the unit dose container configured to contain the compound,
      a diffuser positioned across an opening of the container cavity, the diffuser configured to be in communication with the canister such that propellant exiting the canister travels through the diffuser,
      a nozzle in communication with the container cavity, and
   a puncture member that is configured to, upon coupling the tip to the housing body, puncture an end of the unit dose container such that the unit dose container is in communication with the diffuser, and following contact with the diffuser, the diffused propellant contacts the compound contained in the unit dose container,
   wherein the device is capable of delivering the compound to the olfactory region of the nasal cavity.

2. The device of claim 1, further comprising an additional puncture member, wherein the additional puncture member comprises a front puncture member positioned on the tip.

3. The device of claim 1 wherein the puncture member has an angle of puncture between 15 degrees and 90 degrees, inclusive.

4. The device of claim 1 wherein the puncture member further comprises a side orifice.

5. The device of claim 1 wherein the compound is an intranasal formulation.

6. The device of claim 1 wherein the end of the unit dose container further includes a rubber stopper or a foil seal or combinations thereof.

7. The device of claim 1 wherein the end of the unit dose container includes a puncture area.

8. The device of claim 7 wherein the puncture area is a dimple.

9. The device of claim 1 wherein the puncture member is composed of metal or a polymer or combinations thereof.

10. The device of claim 1 wherein the unit dose container is composed of a polymer or glass.

11. The device of claim 10 where the polymer is polyethylene, ethyl vinyl alcohol copolymer, low-density polyethylene, high-density polyethylene, or polypropylene.

12. The device of claim 1 wherein the unit dose container is cylinder-shaped, cone-shaped, tube-shaped, rectangular-shape, polygonal, hexagonal, or oval-shaped.

13. The device of claim 1 wherein the unit dose container is formed by injection molding, blow molding, injection blow molding, or a blow-fill-seal process.

14. The device of claim 1 wherein the diffuser is a frit.

15. The device of claim 1 further comprising a connection channel having a first end and a second end, where the first end is coupled to the canister and the second end is coupled to the diffuser, wherein a diameter of the diffuser across the opening of the container cavity is greater than a diameter of the connection channel.

16. The device of claim 1, wherein the puncture member comprises a rear puncture member positioned on the housing body, the device further comprising a front puncture member positioned on the tip, wherein each puncture member is configured to puncture a respective end of the unit dose container.

17. The device of claim 1 wherein the puncture member comprises a hollow channel for delivery of the propellant into the unit dose container.

18. The device of claim 1 wherein the puncture member is composed of a porous material for delivery of the propellant into the unit dose container.

19. The device of claim 1 wherein the tip is configured to translate relative to the housing body.

20. The device of claim 1 wherein the tip and the housing body each have respective threaded interfaces that are configured to mate.

* * * * *

UNITED STATES PATENT AND TRADEMARK OFFICE
CERTIFICATE OF CORRECTION

PATENT NO. : 10,537,692 B2
APPLICATION NO. : 14/787455
DATED : January 21, 2020
INVENTOR(S) : Hoekmnan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 749 days.

Signed and Sealed this
Twenty-fourth Day of November, 2020

Andrei Iancu
*Director of the United States Patent and Trademark Office*